(12) United States Patent
Steeg et al.

(10) Patent No.: US 11,001,142 B2
(45) Date of Patent: *May 11, 2021

(54) SYSTEM FOR NON-INVASIVE MEASUREMENT OF AN ANALYTE IN A VEHICLE DRIVER

(71) Applicant: Automotive Coalition for Traffic Safety, Inc., Washington, DC (US)

(72) Inventors: Benjamin Ver Steeg, Washington, DC (US); Trent Ridder, Odenton, MD (US); Len Cech, Brighton, MI (US); Joseph Kae Krause, Northville, MI (US)

(73) Assignee: Automotive Coalition For Traffic Safety, Inc., Sterling, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/161,857

(22) Filed: Oct. 16, 2018

(65) Prior Publication Data

US 2019/0275886 A1    Sep. 12, 2019

Related U.S. Application Data

(63) Continuation of application No. 15/090,809, filed on Apr. 5, 2016, now Pat. No. 10,099,554, which is a
(Continued)

(51) Int. Cl.
*A61B 5/00* (2006.01)
*A61B 5/18* (2006.01)
(Continued)

(52) U.S. Cl.
CPC ............ *B60K 28/06* (2013.01); *A61B 5/0075* (2013.01); *A61B 5/1455* (2013.01);
(Continued)

(58) Field of Classification Search
CPC . A61B 5/1455; A61B 5/14546; A61B 5/6826; G08B 21/02; G06F 21/32
See application file for complete search history.

(56) References Cited

U.S. PATENT DOCUMENTS

| | | | |
|---|---|---|---|
| 3,283,563 A | 11/1966 | Turner et al. | |
| 3,301,482 A | 1/1967 | Bullen | |

(Continued)

FOREIGN PATENT DOCUMENTS

| | | |
|---|---|---|
| CN | 1586944 | 3/2005 |
| CN | 101194270 | 6/2008 |

(Continued)

OTHER PUBLICATIONS

International Search Report PCT/US2014/044350 dated Oct. 10, 2014.

(Continued)

*Primary Examiner* — Eric F Winakur
(74) *Attorney, Agent, or Firm* — Pandiscio & Pandiscio

(57) ABSTRACT

A system for non-invasively measuring an analyte in a vehicle driver and controlling a vehicle based on a measurement of the analyte. At least one solid-state light source is configured to emit different wavelengths of light. A sample device is configured to introduce the light emitted by the at least one solid-state light source into tissue of the vehicle driver. One or more optical detectors are configured to detect a portion of the light that is not absorbed by the tissue of the vehicle driver. A controller is configured to calculate a measurement of the analyte in the tissue of the vehicle driver based on the light detected by the one or more optical detectors, determine whether the measurement of the analyte in the tissue of the vehicle driver exceeds a pre-determined value, and provide a signal to a device configured to control the vehicle.

24 Claims, 35 Drawing Sheets

Related U.S. Application Data continuation of application No. 13/596,827, filed on Aug. 28, 2012, now abandoned.

(60) Provisional application No. 61/528,658, filed on Aug. 29, 2011.

(51) Int. Cl.

| | | |
|---|---|---|
| *A61B 5/1455* | (2006.01) | |
| *A61B 5/145* | (2006.01) | |
| *B60W 40/08* | (2012.01) | |
| *G01N 21/3563* | (2014.01) | |
| *A61B 5/1477* | (2006.01) | |
| *B60K 28/06* | (2006.01) | |
| *G01N 21/27* | (2006.01) | |

(52) U.S. Cl.
CPC ........ *A61B 5/1477* (2013.01); *A61B 5/14546* (2013.01); *A61B 5/18* (2013.01); *A61B 5/4845* (2013.01); *B60W 40/08* (2013.01); *G01N 21/27* (2013.01); *G01N 21/3563* (2013.01); *B60W 2040/0836* (2013.01); *G01N 2201/062* (2013.01); *G01N 2201/0612* (2013.01); *G01N 2201/08* (2013.01); *G01N 2201/12* (2013.01)

(56) References Cited

U.S. PATENT DOCUMENTS

| | | |
|---|---|---|
| 3,792,351 A | 2/1974 | Ireland |
| 3,897,659 A | 8/1975 | Henry |
| 4,090,078 A | 5/1978 | Heim |
| 4,290,052 A | 9/1981 | Eichelberger et al. |
| 4,535,620 A | 8/1985 | Cunningham |
| 4,678,057 A | 7/1987 | Elfman et al. |
| 4,749,553 A | 6/1988 | Lopez et al. |
| 4,843,377 A | 6/1989 | Fuller et al. |
| 4,868,545 A | 9/1989 | Jones |
| 4,916,435 A | 4/1990 | Fuller |
| 4,975,581 A | 12/1990 | Robinson et al. |
| 5,006,315 A | 4/1991 | Maroulis et al. |
| 5,303,575 A | 4/1994 | Brown et al. |
| 5,325,442 A | 6/1994 | Knapp |
| 5,426,415 A | 6/1995 | Prachar et al. |
| 5,544,276 A | 8/1996 | Loux et al. |
| 5,652,398 A | 7/1997 | Johnson |
| 5,655,530 A | 8/1997 | Messerschmidt |
| 5,746,973 A | 5/1998 | Naraghi |
| 5,823,951 A | 10/1998 | Messerschmidt |
| 5,830,112 A | 11/1998 | Wang et al. |
| 5,843,377 A | 12/1998 | Fandel et al. |
| 5,877,345 A | 3/1999 | Bauer, Jr. et al. |
| 5,955,886 A | 9/1999 | Cohen et al. |
| 6,038,242 A | 3/2000 | Yamamoto et al. |
| 6,129,680 A | 10/2000 | Mottram |
| 6,152,876 A | 11/2000 | Robinson et al. |
| 6,157,041 A | 12/2000 | Thomas et al. |
| 6,229,908 B1 * | 5/2001 | Edmonds, III ..... A61B 5/14546 340/5.2 |
| 6,240,306 B1 | 5/2001 | Rohrscheib et al. |
| 6,266,353 B1 | 7/2001 | Freitas et al. |
| 6,441,388 B1 | 8/2002 | Thomas et al. |
| 6,528,809 B1 | 3/2003 | Thomas et al. |
| 6,622,032 B1 | 9/2003 | Robinson et al. |
| 6,684,099 B2 | 1/2004 | Ridder et al. |
| 6,794,988 B1 | 9/2004 | Weiss et al. |
| 6,862,091 B2 | 3/2005 | Johnson |
| 6,983,176 B2 | 1/2006 | Gardner et al. |
| 7,016,713 B2 | 3/2006 | Gardner et al. |
| 7,092,832 B2 | 8/2006 | Brown |
| 7,098,037 B2 | 8/2006 | Haas et al. |
| 7,173,524 B2 | 2/2007 | Ponziani |
| 7,202,091 B2 | 4/2007 | Jones et al. |
| 7,239,227 B1 | 7/2007 | Gupta et al. |
| 7,386,152 B2 | 6/2008 | Rowe et al. |
| 7,446,878 B2 | 11/2008 | Ridder et al. |
| 7,616,123 B2 * | 11/2009 | Ridder ............... A61B 5/14546 340/573.1 |
| 7,764,982 B2 * | 7/2010 | Dalke ................ A61B 5/14552 600/310 |
| 7,848,605 B2 | 12/2010 | Ridder et al. |
| 7,890,158 B2 | 2/2011 | Rowe et al. |
| 8,095,193 B2 * | 1/2012 | Ridder ............... A61B 5/14532 600/310 |
| 8,174,394 B2 * | 5/2012 | Ridder ................ A61B 5/1455 340/573.1 |
| 8,306,595 B2 | 11/2012 | Osaki et al. |
| 8,469,134 B2 | 6/2013 | Osaki et al. |
| 8,479,864 B2 | 7/2013 | White et al. |
| 8,605,959 B2 | 12/2013 | Kangas et al. |
| 8,773,390 B1 | 7/2014 | Clark et al. |
| 8,977,002 B2 | 3/2015 | Mercier et al. |
| 8,977,023 B2 | 3/2015 | Buckland |
| 9,163,718 B2 | 10/2015 | Nelson et al. |
| 9,459,221 B2 | 10/2016 | Matsumoto et al. |
| 9,636,457 B2 | 5/2017 | Newberry et al. |
| 9,642,538 B2 | 5/2017 | Newberry |
| 9,642,578 B2 | 5/2017 | Newberry |
| 9,671,954 B1 | 6/2017 | Jaugilas et al. |
| 10,040,349 B2 | 8/2018 | DeVries et al. |
| 10,099,554 B2 * | 10/2018 | Steeg .................. A61B 5/1455 |
| 10,452,257 B2 | 10/2019 | Kim et al. |
| 2003/0039299 A1 | 2/2003 | Horovitz et al. |
| 2003/0048000 A1 | 3/2003 | Harter et al. |
| 2003/0085284 A1 | 5/2003 | Bremer et al. |
| 2003/0204290 A1 | 10/2003 | Sadler et al. |
| 2004/0081339 A1 | 4/2004 | Benkley, III |
| 2004/0155752 A1 | 8/2004 | Radke |
| 2004/0204868 A1 | 10/2004 | Maynard et al. |
| 2004/0260194 A1 | 12/2004 | Bayer et al. |
| 2005/0241871 A1 | 11/2005 | Stewart et al. |
| 2006/0153740 A1 | 7/2006 | Sultan et al. |
| 2006/0167349 A1 | 7/2006 | Gardner et al. |
| 2006/0206034 A1 | 9/2006 | Stock et al. |
| 2006/0210120 A1 | 9/2006 | Rowe et al. |
| 2006/0253711 A1 | 11/2006 | Kallmann |
| 2006/0285076 A1 | 12/2006 | Takeda et al. |
| 2007/0080951 A1 | 4/2007 | Maruyama et al. |
| 2007/0142720 A1 | 6/2007 | Ridder et al. |
| 2007/0144812 A1 | 6/2007 | Stewart et al. |
| 2007/0245801 A1 | 10/2007 | Stock |
| 2008/0006077 A1 | 1/2008 | Crabtree et al. |
| 2008/0045806 A1 | 2/2008 | Keppler |
| 2008/0061238 A1 | 3/2008 | Hok et al. |
| 2008/0107309 A1 | 5/2008 | Cerni |
| 2008/0115981 A1 | 5/2008 | Bechtel |
| 2008/0171947 A1 | 7/2008 | Ruffert |
| 2008/0187015 A1 | 8/2008 | Yoshikawa et al. |
| 2008/0246735 A1 | 10/2008 | Reynolds et al. |
| 2008/0252412 A1 | 10/2008 | Larsson et al. |
| 2008/0319286 A1 | 12/2008 | Ridder et al. |
| 2009/0003764 A1 | 1/2009 | Ridder et al. |
| 2009/0007634 A1 | 1/2009 | Mitchell |
| 2009/0248260 A1 | 10/2009 | Flanagan |
| 2010/0010325 A1 * | 1/2010 | Ridder ............... A61B 5/14546 600/310 |
| 2010/0028210 A1 | 2/2010 | Ozaki et al. |
| 2010/0031718 A1 | 2/2010 | Heil |
| 2010/0036592 A1 | 2/2010 | Osaki et al. |
| 2010/0097198 A1 | 4/2010 | Suzuki |
| 2010/0188232 A1 | 7/2010 | Lambert et al. |
| 2010/0207895 A1 | 8/2010 | Joung et al. |
| 2010/0252737 A1 | 10/2010 | Fournel et al. |
| 2010/0327167 A1 | 12/2010 | Koop et al. |
| 2011/0178420 A1 | 7/2011 | Ridder et al. |
| 2011/0205038 A1 | 8/2011 | Drouin et al. |
| 2011/0283770 A1 | 11/2011 | Hok |
| 2011/0309932 A1 | 12/2011 | Arringdale et al. |
| 2012/0050231 A1 | 3/2012 | Westhues et al. |
| 2012/0078473 A1 | 3/2012 | Ridder et al. |
| 2013/0110311 A1 | 5/2013 | Ver Steeg et al. |
| 2013/0179780 A1 | 7/2013 | Ooka |
| 2014/0002237 A1 | 1/2014 | Infante et al. |
| 2014/0098304 A1 | 4/2014 | Kim et al. |

(56) References Cited

U.S. PATENT DOCUMENTS

| | | |
|---|---|---|
| 2014/0156149 A1 | 6/2014 | Feit |
| 2014/0184957 A1 | 7/2014 | Satou et al. |
| 2014/0260537 A1 | 9/2014 | Nash et al. |
| 2014/0318293 A1 | 10/2014 | Nelson et al. |
| 2015/0066238 A1 | 3/2015 | Todd et al. |
| 2015/0169063 A1 | 6/2015 | Goto |
| 2015/0219620 A1 | 8/2015 | Hok et al. |
| 2015/0233897 A1 | 8/2015 | Hok et al. |
| 2015/0331508 A1 | 11/2015 | Nho et al. |
| 2016/0224184 A1 | 8/2016 | Nordback |
| 2017/0050518 A1 | 2/2017 | Steeg et al. |
| 2017/0103327 A1 | 4/2017 | Penilla et al. |
| 2017/0336903 A1 | 11/2017 | Rivaud et al. |
| 2019/0135199 A1 | 5/2019 | Galan Garcia et al. |

FOREIGN PATENT DOCUMENTS

| | | |
|---|---|---|
| CN | 101548496 | 9/2009 |
| DE | 19811872 | 8/1999 |
| DE | 19938064 | 8/2000 |
| DE | 10157907 | 6/2003 |
| EP | 0593386 | 4/1994 |
| EP | 0791899 | 8/1997 |
| EP | 1688741 | 8/2006 |
| GB | 2431470 | 4/2007 |
| GB | 2442980 | 4/2008 |
| JP | 61-181440 | 8/1986 |
| JP | H08-222795 | 8/1996 |
| JP | 10-309268 | 11/1998 |
| JP | 2001-057440 | 2/2001 |
| JP | 2001-266133 | 9/2001 |
| JP | 2002-116141 | 4/2002 |
| JP | 2003-272463 | 9/2003 |
| JP | 2004-086866 | 3/2004 |
| JP | 2004-117104 | 4/2004 |
| JP | 2005-227553 | 8/2005 |
| JP | 2005-323892 | 11/2005 |
| JP | 2006-027198 | 2/2006 |
| JP | 2006-352009 | 12/2006 |
| JP | 2008-177473 | 7/2008 |
| JP | 2008-203598 | 9/2008 |
| JP | 2008-203774 | 9/2008 |
| JP | 2008-253455 | 10/2008 |
| JP | 2008-291710 | 12/2008 |
| JP | 2008-302915 | 12/2008 |
| JP | 2008-308037 | 12/2008 |
| JP | 2009-526707 | 7/2009 |
| JP | 2010-036799 | 2/2010 |
| JP | 2011-501121 | 1/2011 |
| JP | 2011-104112 | 6/2011 |
| JP | 2012-198648 | 10/2012 |
| WO | WO 97/000443 | 1/1997 |
| WO | WO 01/67144 | 9/2001 |
| WO | WO 2004/090786 | 10/2004 |
| WO | WO 2006/050513 | 11/2006 |
| WO | WO 2008/134135 | 6/2008 |
| WO | WO 2008/118205 | 10/2008 |
| WO | WO 2010/085716 | 7/2010 |
| WO | WO 2012/064252 | 5/2012 |
| WO | WO 2013/033099 | 3/2013 |

OTHER PUBLICATIONS

Extended European Search Report EP 13 83 0956 dated Jul. 13, 2015.
Extended European Search Report EP 13 83 1692 dated Jul. 13, 2015.
Giebel, Brian M., Thesis and Dissertation, "Advancement and Application of Gas Chromatography Isotope Ratio Mass Spectrometry Techniques for Atmospheric Trace Gas Analysis," Published 2011, 252 total pages.
International Search Report PCT/SE2013/ 050990 dated Feb. 3, 2014.
International Search Report PCT/SE2013/050991 dated Feb. 3, 2014.
International Search Report PCT/USS2012/052673 dated Jan. 31, 2013.
Talbert, Bruce, et al., "A Study of Regulators for Delivering Gases Containing Low Concentrations of Hydrogen Sulfide," LCGC North America. 22(6):562, 564, 567-568 (2004).
Written Opinion of the International Searching Authority PCT/US2012/052673 dated Jan. 31, 2013.
Written Opinion oflhe International Searching Authority PCT/US2014/044350 dated Oct. 10, 2014.

* cited by examiner

SYSTEM FOR NON-INVASIVE MEASUREMENT OF AN ANALYTE IN A VEHICLE DRIVER

REFERENCE TO PENDING PRIOR PATENT APPLICATIONS

This patent application is a continuation of pending prior U.S. patent application Ser. No. 15/090,809, filed Apr. 5, 2016 by Automotive Coalition for Traffic Safety, Inc. for SYSTEM FOR NON-INVASIVE MEASUREMENT OF AN ANALYTE IN A VEHICLE DRIVER, which patent application in turn is a continuation of prior U.S. patent application Ser. No. 13/596,827, filed Aug. 28, 2012 by Benjamin Ver Steeg et al. for SYSTEM FOR NONINVASIVE MEASUREMENT OF AN ANALYTE IN A VEHICLE DRIVER, which in turn claims benefit of prior U.S. Provisional Patent Application Ser. No. 61/528,658, filed Aug. 29, 2011 by Benjamin Ver Steeg et al. for SYSTEM FOR NONINVASIVE DETERMINATION OF ALCOHOL IN TISSUE.

The three (3) above-identified patent applications are hereby incorporated herein by reference.

BACKGROUND

The present application generally relates to a system and methods for non-invasively measuring an analyte in a vehicle driver. More specifically, the application relates to a measurement quantitative spectroscopy system for measuring the presence or concentration of an analyte, for example, alcohol, alcohol byproducts, alcohol adducts, or substances of abuse, utilizing non-invasive techniques in combination with multivariate analysis.

Current practice for alcohol measurements is based upon either blood measurements or breath testing. Blood measurements define the gold standard for determining alcohol intoxication levels. However, blood measurements require either a venous or capillary sample and involve significant handling precautions in order to minimize health risks. Once extracted, the blood sample must be properly labeled and transported to a clinical laboratory or other suitable location where a clinical gas chromatograph is typically used to measure the blood alcohol level. Due to the invasiveness of the procedure and the amount of sample handling involved, blood alcohol measurements are usually limited to critical situations such as for traffic accidents, violations where the suspect requests this type of test, and accidents where injuries are involved.

Because it is less invasive, breath testing is more commonly encountered in the field. In breath testing, the subject must expire air into the instrument for a sufficient time and volume to achieve a stable breath flow that originates from the alveoli deep within the lungs. The device then measures the alcohol content in the air, which is related to blood alcohol through a breath-blood partition coefficient. The blood-breath partition coefficient used in the United States is 2100 (implied units of mg EtOH/dL blood per mg EtOH/dL air) and varies between 1900 and 2400 in other nations. The variability in the partition coefficient is due to the fact that it is highly subject dependent. In other words, each subject will have a partition coefficient in the 1900 to 2400 range that depends on his or her physiology. Since knowledge of each subject's partition coefficient is unavailable in field applications, each nation assumes a single partition coefficient value that is globally applied to all measurements. In the U.S., defendants in DUI cases often use the globally applied partition coefficient as an argument to impede prosecution.

Breath measurements have additional limitations. First, the presence of "mouth alcohol" can falsely elevate the breath alcohol measurement. This necessitates a 15-minute waiting period prior to making a measurement in order to ensure that no mouth alcohol is present. For a similar reason, a 15 minute delay is required for individuals who are observed to burp or vomit. A delay of 10 minutes or more is often required between breath measurements to allow the instrument to return to equilibrium with the ambient air and zero alcohol levels. In addition, the accuracy of breath alcohol measurements is sensitive to numerous physiological and environmental factors.

Multiple government agencies, and society in general, seek non-invasive alternatives to blood and breath alcohol measurements. Quantitative spectroscopy offers the potential for a completely non-invasive alcohol measurement that is not sensitive to the limitations of the current measurement methodologies. While non-invasive determination of biological attributes by quantitative spectroscopy has been found to be highly desirable, it has been very difficult to accomplish. Attributes of interest include, as examples, analyte presence, analyte concentration (e.g., alcohol concentration), direction of change of an analyte concentration, rate of change of an analyte concentration, disease presence (e.g., alcoholism), disease state, and combinations and subsets thereof. Non-invasive measurements via quantitative spectroscopy are desirable because they are painless, do not require a fluid draw from the body, carry little risk of contamination or infection, do not generate any hazardous waste, and can have short measurement times.

Several systems have been proposed for the non-invasive determination of attributes of biological tissue. These systems have included technologies incorporating polarimetry, mid-infrared spectroscopy, Raman spectroscopy, Kromoscopy, fluorescence spectroscopy, nuclear magnetic resonance spectroscopy, radio-frequency spectroscopy, ultrasound, transdermal measurements, photo-acoustic spectroscopy, and near-infrared spectroscopy. However, these systems have not replaced direct and invasive measurements.

As an example, Robinson et al. in U.S. Pat. No. 4,975,581 disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as alcohol, but also can be any chemical or physical property of the sample. The method of Robinson et al. involves a two-step process that includes both calibration and prediction steps.

In the calibration step, the infrared light is coupled to calibration samples of known characteristic values so that there is attenuation of at least several wavelengths of the infrared radiation as a function of the various components and analytes comprising the sample with known characteristic value. The infrared light is coupled to the sample by passing the light through the sample or by reflecting the light off the sample. Absorption of the infrared light by the sample causes intensity variations of the light that are a function of the wavelength of the light. The resulting intensity variations at a minimum of several wavelengths are measured for the set of calibration samples of known characteristic values. Original or transformed intensity variations are then empirically related to the known characteristics of the calibration samples using multivariate algorithms to obtain a multivariate calibration model. The model preferably accounts for subject variability, instrument variability, and environment variability.

In the prediction step, the infrared light is coupled to a sample of unknown characteristic value, and a multivariate calibration model is applied to the original or transformed intensity variations of the appropriate wavelengths of light measured from this unknown sample. The result of the prediction step is the estimated value of the characteristic of the unknown sample. The disclosure of Robinson et al. is incorporated herein by reference.

A further method of building a calibration model and using such model for prediction of analytes and/or attributes of tissue is disclosed in commonly assigned U.S. Pat. No. 6,157,041 to Thomas et al., entitled "Method and Apparatus for Tailoring Spectrographic Calibration Models," the disclosure of which is incorporated herein by reference.

In U.S. Pat. No. 5,830,112, Robinson describes a general method of robust sampling of tissue for non-invasive analyte measurement. The sampling method utilizes a tissue-sampling accessory that is pathlength optimized by spectral region for measuring an analyte such as alcohol. The patent discloses several types of spectrometers for measuring the spectrum of the tissue from 400 to 2500 nm, including acousto-optical tunable filters, discrete wavelength spectrometers, filters, grating spectrometers and FTIR spectrometers. The disclosure of Robinson is incorporated herein by reference.

Although there has been substantial work conducted in attempting to produce commercially viable non-invasive near-infrared spectroscopy-based systems for determination of biological attributes, no such device is presently available. It is believed that prior art systems discussed above have failed for one or more reasons to fully meet the challenges imposed by the spectral characteristics of tissue which make the design of a non-invasive measurement system a formidable task. Thus, there is a substantial need for a commercially viable device which incorporates subsystems and methods with sufficient accuracy and precision to make clinically relevant determinations of biological attributes in human tissue.

SUMMARY

One embodiment of the invention relates to a system for non-invasively measuring an analyte in a vehicle driver and controlling a vehicle based on a measurement of the analyte. The system includes at least one solid-state light source, a sample device, one or more optical detectors and a controller. The at least one solid-state light source is configured to emit different wavelengths of light. The sample device is configured to introduce the light emitted by the at least one solid-state light source into tissue of the vehicle driver. The one or more optical detectors are configured to detect a portion of the light that is not absorbed by the tissue of the vehicle driver. The controller is configured to calculate a measurement of the analyte in the tissue of the vehicle driver based on the light detected by the one or more optical detectors, determine whether the measurement of the analyte in the tissue of the vehicle driver exceeds a pre-determined value, and provide a signal to a device configured to control the vehicle.

Another embodiment of the invention relates to a method for non-invasively measuring an analyte in a vehicle driver and controlling a vehicle based on a measurement of the analyte. A sample device introduces different wavelengths of light emitted by at least one solid-state light source into tissue of the vehicle driver. One or more optical detectors detect a portion of the light that is not absorbed by the tissue of the vehicle driver. A controller calculates a measurement of the analyte in the tissue of the vehicle driver based on the light detected by the one or more optical detectors. The controller determines whether the measurement of the analyte in the tissue of the vehicle driver exceeds a pre-determined value and controls the vehicle based on the measurement of the analyte in the tissue of the vehicle driver.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The accompanying drawings, which are incorporated in and constitute a part of this specification, illustrate preferred embodiments of the invention and together with the description serve to explain principles of the invention. No attempt is made to show structural details of the present disclosure in more detail than may be necessary for a fundamental understanding of the present disclosure and the various ways in which it may be practiced.

DETAILED DESCRIPTION

Figure 1:
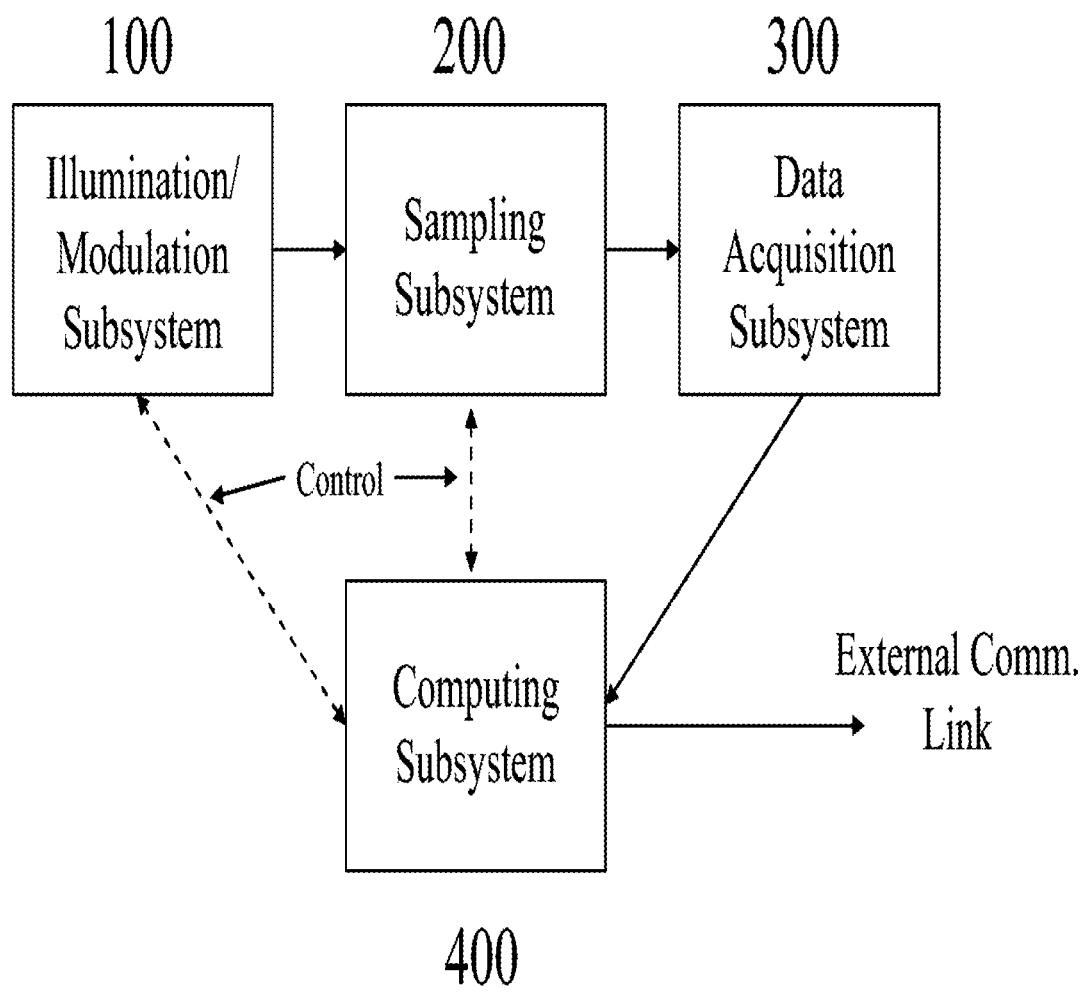
FIG. 1 is a schematic depiction of a non-invasive spectrometer system incorporating the disclosed subsystems.

Before turning to the figures, which illustrate the exemplary embodiments in detail, it should be understood that the present disclosure is not limited to the details or methodology set forth in the description or illustrated in the figures. It should also be understood that the terminology is for the purpose of description only and should not be regarded as limiting. An effort has been made to use the same or like reference numbers throughout the drawings to refer to the same or like parts.

For the purposes of the present application, the term "analyte concentration" generally refers to the concentration of an analyte, such as alcohol. The term "analyte property" includes analyte concentration and other properties, such as the presence or absence of the analyte or the direction or rate of change of the analyte concentration, or a biometric, which can be measured in conjunction with or instead of the analyte concentration. While the disclosure generally references alcohol as the "analyte" of interest, other analytes, including but not limited to substances of abuse, alcohol biomarkers, and alcohol byproducts, are also intended to be covered by the systems and methods disclosed in the present application. The term "alcohol" is used as an example analyte of interest; the term is intended to include ethanol, methanol, ethyl glycol or any other chemical commonly referred to as alcohol. For the purposes of this application, the term "alcohol byproducts" includes the adducts and byproducts of the metabolism of alcohol by the body including, but not limited to, acetone, acetaldehyde, and acetic acid. The term "alcohol biomarkers" includes, but is not limited to, Gamma Glutamyl Transferase (GGT), Aspartate Amino Transferase (AST), Alanine Amino Transferase (ALT), Mean Corpuscular Volume (MCV), Carbohydrate-Deficient Transferrin (CDT), Ethyl Glucuronide (EtG), Ethyl Sulfate (EtS), and Phosphatidyl Ethanol (PEth). The term "substances of abuse" refers to, but is not limited to, THC (Tetrahydrocannabinol or marijuana), cocaine, M-AMP (methamphetamine), OPI (morphine and heroin), OxyContin, Oxycodone, and PCP (phencyclidine). The term "biometric" refers to an analyte or biological characteristic that can be used to identify or verify the identity of a specific person or subject. The present application discloses systems and methods that address the need for analyte measurements of samples utilizing spectroscopy where the term "sample" generally refers to biological tissue. The term "subject" generally refers to a person from whom a sample measurement was acquired.

The terms "solid-state light source" or "semiconductor light source" refer to all sources of light, whether spectrally narrow (e.g. a laser) or broad (e.g. an LED) that are based upon semiconductors which include, but are not limited to, light emitting diodes (LED's), vertical cavity surface emitting lasers (VCSEL's), horizontal cavity surface emitting lasers (HCSEL's), quantum cascade lasers, quantum dot lasers, diode lasers, or other semiconductor diodes or lasers. The term "diode laser" refers to any laser where the active medium is based on a semiconductor which include, but are not limited to, double heterostructure lasers, quantum well lasers, quantum cascade lasers, separate confinement heterostructure lasers, distributed feedback (DFB) lasers, VCSEL's, VECSEL's, HCSEL's, external-cavity diode lasers, Fabry-Perot lasers. Furthermore, plasma light sources and organic LED's, while not strictly based on semiconductors, are also contemplated in the embodiments of the present invention and are thus included under the solid-state light source and semiconductor light source definitions for the purposes of this application.

For the purposes of this application the term "dispersive spectrometer" indicates a spectrometer based upon any device, component, or group of components that spatially separate one or more wavelengths of light from other wavelengths. Examples include, but are not limited to, spectrometers that use one or more diffraction gratings, prisms, holographic gratings. For the purposes of this application the term "interferometric/modulating spectrometer" indicates a class of spectrometers based upon the optical modulation of different wavelengths of light to different frequencies in time or selectively transmits or reflects certain wavelengths of light based upon the properties of light interference. Examples include, but are not limited to, Fourier transform interferometers, Sagnac interferometers, mock interferometers, Michelson interferometers, one or more etalons, or acousto-optical tunable filters (AOTF's). One skilled in the art recognizes that spectrometers based on combinations of dispersive and interferometric/modulating properties, such as those based on lamellar gratings, are also contemplated as being used with the systems and methods disclosed in the present application.

The present application discloses the use of "signals" in some of the examples as absorbance or other spectroscopic measurements. Signals can comprise any measurement obtained concerning the spectroscopic measurement of a sample or change in a sample, e.g., absorbance, reflectance, intensity of light returned, fluorescence, transmission, Raman spectra, or various combinations of measurements, at one or more wavelengths. Some embodiments make use of one or more models, where such a model can be anything that relates a signal to the desired property. Some examples of models include those derived from multivariate analysis methods, such as partial least squares regression (PLS), linear regression, multiple linear regression (MLR), classical least squares regression (CLS), neural networks, discriminant analysis, principal components analysis (PCA), principal components regression (PCR), discriminant analysis, neural networks, cluster analysis, and K-nearest neighbors. Single or multi-wavelength models based on the Beer-Lambert law are special cases of classical least squares and are thus included in the term multivariate analysis for the purposes of the present application.

For the purposes of the application, the term "about" applies to all numeric values, whether or not explicitly indicated. The term "about" generally refers to a range of numbers that one of skill in the art would consider equivalent to the recited value (i.e., having the same function or result). In some instances, the term "about" can include numbers that are rounded to the nearest significant figure.

Spectroscopic measurement systems typically require some means for resolving and measuring different wavelengths of light in order to obtain a spectrum. Some common approaches achieve the desired spectrum include dispersive (e.g. grating and prism based) spectrometers and interferometric (e.g. Michelson, Sagnac, or other interferometer) spectrometers. Noninvasive measurement systems that incorporate such approaches are often limited by the expensive nature of dispersive and interferometric devices as well as their inherent size, fragility, and sensitivity to environmental effects. The present application discloses systems and methods that can provide an alternative approach for resolving and recording the intensities of different wavelengths using solid-state light sources such as light emitting diodes (LED's), vertical cavity surface emitting lasers (VCSEL's), horizontal cavity surface emitting lasers (VCSEL's), diode lasers, quantum cascade lasers, or other solid-state light sources.

Referring generally to the figures, the disclosed system overcomes the challenges posed by the spectral characteristics of tissue by incorporating a design that includes, in some embodiments, optimized subsystems. The design contends with the complexities of the tissue spectrum, high signal-to-noise ratio and photometric accuracy requirements, tissue sampling errors, calibration maintenance problems, calibration transfer problems plus a host of other issues. The subsystems can include an illumination/modulation subsystem, a tissue sampling subsystem, a data acquisition subsystem, a computing subsystem, and a calibration subsystem.

An apparatus and method for non-invasive determination of attributes of human tissue by quantitative near infrared spectroscopy is disclosed herein. The system includes subsystems optimized to contend with the complexities of the tissue spectrum, high signal-to-noise ratio and photometric accuracy requirements, tissue sampling errors, calibration maintenance problems, and calibration transfer problems. The subsystems include an illumination/modulation subsystem, a tissue sampling subsystem, a data acquisition subsystem, and a computing subsystem.

The present application further discloses apparatus and methods that allow for implementation and integration of each of these subsystems in order to maximize the net attribute signal-to-noise ratio. The net attribute signal is the portion of the near-infrared spectrum that is specific for the attribute of interest because it is orthogonal to all other sources of spectral variance. The orthogonal nature of the net attribute signal makes it perpendicular to the space defined by any interfering species and as a result, the net attribute signal is uncorrelated to these sources of variance. The net attribute signal-to-noise ratio is directly related to the accuracy and precision for non-invasive determination of the attribute by quantitative near-infrared spectroscopy.

The present application discloses the use of near-infrared radiation for analysis. Radiation in the wavelength range of 1.0 to 2.5 microns (or wavenumber range of 10,000 to 4,000 $cm^{-1}$) can be suitable for making some non-invasive measurements because such radiation has acceptable specificity for a number of analytes, including alcohol, along with tissue optical penetration depths of up to several millimeters with acceptable absorbance characteristics. In the 1.0 to 2.5 micron spectral region, the large number of optically active substances that make up the tissue complicate the measurement of any given substance due to the overlapped nature of their absorbance spectra. Multivariate analysis techniques can be used to resolve these overlapped spectra such that accurate measurements of the substance of interest can be achieved. Multivariate analysis techniques, however, can require that multivariate calibrations remain robust over time (calibration maintenance) and be applicable to multiple instruments (calibration transfer). Other wavelength regions, such as the visible and infrared, can also be suitable for the disclosed systems and methods.

The present application discloses a multidisciplinary approach to the design of a spectroscopic instrument that incorporates an understanding of the instrument subsystems, tissue physiology, multivariate analysis, near-infrared spectroscopy and overall system operation. Further, the interactions between the subsystems have been analyzed so that the behavior and requirements for the entire non-invasive measurement device are well understood and result in a design for a commercial instrument that will make non-invasive measurements with sufficient accuracy and precision at a price and size that is commercially viable.

The present application also discloses systems and methods for use with the unique sensing requirements for a transportation systems including but not limited to motorcycles, automobiles, trucks, ships, trains and aircraft; where the system must operate over a wide range of temperature, atmospheric pressure, altitudes, humidity, mechanical orientation, ambient lighting and environmental constituent (e.g. salt, sand, dust, smoke) environments. The disclosed system may operate over a full range of potential users distinguishable through differences in weight, stature, age, ethnicity, gender, health, fitness level and other human distinguishing factors. The disclosed system may remain functional over a full vehicle life and maintain diagnostics and telltales indicating required maintenance or serviceable unit replacement. The disclosed system can provide a human machine interface which provides visual, haptic, audible feedback to inform the system user of a correct and incorrect measurement. The system provides diagnostics and user feedback indicating proper and improper measurements including detection of intentional and un-intentional system tampering or measurement spoofing. The system can maintain operational modes which can be enabled/disabled based on administrative controls (e.g. passwords). The system can provide one or more communication and/or power interfaces to external transportation enabling or human machine interface systems using one or more existing or developed communication protocols to receive data and/or power required for system operation or to enable, disable or modify the operation of the external systems. The system can support the capability to allow for measurement accuracy and precision verification or calibration during manufacturing, installation and/or service through a prosthetic reference device.

The subsystems of the non-invasive monitor are highly optimized to provide reproducible and, preferably, uniform radiance of the tissue, low tissue sampling error, depth targeting of the tissue layers that contain the property of interest, efficient collection of diffuse reflectance spectra from the tissue, high optical throughput, high photometric accuracy, large dynamic range, excellent thermal stability, effective calibration maintenance, effective calibration transfer, built-in quality control, and ease-of-use.

Referring now to FIG. 1, a non-invasive monitor that is able to achieve acceptable levels of accuracy and precision for analyte property measurements is depicted in schematic view. The overall systems can be viewed for discussion purposes as comprising five subsystems; those skilled in the art will appreciate other subdivisions of the functionality disclosed. The subsystems include an illumination/modulation subsystem 100, a tissue sampling subsystem 200, a data acquisition subsystem 300, a processing subsystem 400, and a calibration subsystem (not illustrated).

Figure 2:
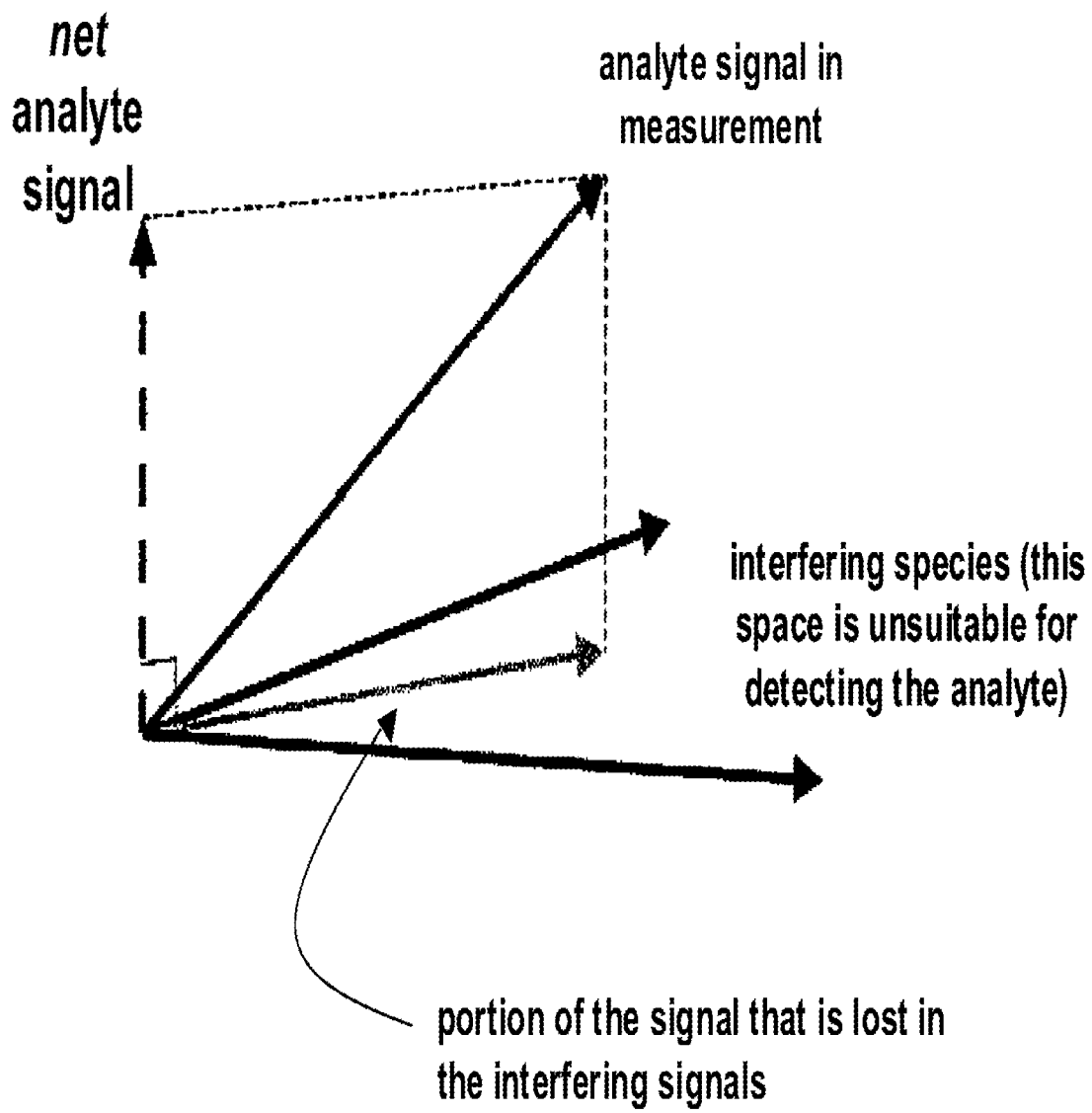
FIG. 2 is a graphical depiction of the concept of net attribute signal in a three-component system.

The subsystems can be designed and integrated in order to achieve a desirable net attribute signal-to-noise ratio. The net attribute signal is the portion of the near-infrared spectrum that is specific for the attribute of interest because it is orthogonal to other sources of spectral variance. FIG. 2 is a graphical representation of the net attribute signal in a three dimensional system. The net attribute signal-to-noise ratio is directly related to the accuracy and precision of the non-invasive attribute determination by quantitative near-infrared spectroscopy.

The subsystems provide reproducible and preferably spatially uniform radiance of the tissue, low tissue sampling error, depth targeting of appropriate layers of the tissue, efficient collection of diffuse reflectance spectra from the tissue, high optical throughput, high photometric accuracy, large dynamic range, excellent thermal stability, effective calibration maintenance, effective calibration transfer, built-in quality control and ease-of-use. Each of the subsystems is discussed below in more detail.

Illumination/Modulation Subsystem

The illumination/modulation subsystem 100 generates the light used to interrogate the sample (e.g. skin tissue of a human). In classical spectroscopy using dispersive or interferometric spectrometers, the spectrum of a polychromatic light source (or light emitted from a sample of interest) is measured either by dispersing the different wavelengths of light spatially (e.g. using a prism or a diffraction grating) or by modulating different wavelengths of light to different frequencies (e.g. using a Michelson interferometer). In these cases, a spectrometer (a subsystem distinct from the light source) is required to perform the function of "encoding" different wavelengths either spatially or in time such that each can be measured substantially independently of other wavelengths. While dispersive and interferometric spectrometers are known in the art and can adequately serve their function in some environments and applications, they can be limited by their cost, size, fragility, signal to noise ratio (SNR), and complexity in other applications and environments.

An advantage of solid-state light sources incorporated in the disclosed systems is that the sources can be independently modulated in intensity. Thus, multiple solid-state light sources that emit different wavelengths of light can be used with each solid-state light source modulated at a different frequency or collectively modulated according to a predefined scheme such as those defined by a Hadamard or similar approach. The independently modulated solid-state light sources can be optically combined into a single beam and introduced to the sample. A portion of the light can be collected from the sample and measured by a single photodetector. The result is the effective combination of the solid-state light source and the spectrometer into a single illumination/modulation subsystem that can offer significant benefits in size, cost, energy consumption, and overall system stability since the spectrometer, as an independent subsystem, is eliminated from the measurement system. Furthermore, as all wavelengths are independently modulated and can be combined into a single beam, a single element photodetector (rather than an array of photodetectors) is suitable to detect all analytical light. This can represent a significant reduction in system complexity and cost relative to systems and embodiments with multiple photodetector elements.

Several parameters of systems for measuring analyte properties incorporating solid-state light sources must be considered including, but not limited to, the number of solid-state light sources required to perform the desired measurement, the emission profile of the solid-state light sources (e.g. spectral width, intensity), solid-state light source stability and control, and their optical combination. As each solid-state light source is a discrete element, it can be advantageous to combine the output of multiple solid-state light sources into a single beam such that they are consistently introduced and collected from the sample.

Furthermore, the modulation scheme for the solid-state light sources must also be considered as some types of sources can be amenable to sinusoidal modulations in intensity where others can be amenable to being switched on and off or square wave modulated. In the case of sinusoidal modulation, multiple solid-state light sources can be modulated at different frequencies based on the electronics design of the system. The light emitted by the multiple sources can be optically combined, for example using a light pipe or other homogenizer, introduced and collected from the sample of interest, and then measured by a single detector. The resulting signal can be converted into an intensity versus wavelength spectrum via a Fourier, or similar, transform.

Alternatively, some solid-state light sources are switched between the on and off state or square wave modulated which are amenable to a Hadamard transform approach. However, in some embodiments, rather than a traditional Hadamard mask that blocks or passes different wavelengths at different times during a measurement, the Hadamard scheme can be implemented in electronics as solid-state light sources can be cycled at high frequencies. A Hadamard or similar transform can be used to determine the intensity versus wavelength spectrum. One skilled in the art recognizes that there are alternatives to Hadamard encoding approaches that are equally suitable to the present invention.

In one embodiment, a 47 wavelength Hadamard encoding scheme is utilized and depicted as a matrix of binary numbers. Each row corresponds to one state of the Hadamard scheme and each column corresponds to a wavelength in the measurement system. For each state, a value of "1" indicates that wavelength (e.g. laser diode) is on for that state while a value of "0" indicates that wavelength is off for that state. Each measurement of each state corresponds to one scan. The light emitted by the Illumination/Modulation Subsystem 100 is delivered to the sample by the Sampling Subsystem 200. A portion of that light is collected, detected, digitized, and recorded by the photodetector in the Data Acquisition Subsystem 300. The next state in the Hadamard scheme (e.g. a different set of wavelengths is on for that state) is then measured and recorded. This proceeds until all Hadamard states have been measured (referred to as a "Hadamard Cycle" herein). Once a Hadamard cycle has been completed, the intensity versus wavelength spectrum is determined by calculating the dot product of the recorded intensity versus state data and the matrix inverse of the Hadamard scheme. While the example of Hadamard encoding described above is comprised of 47 wavelengths, one skilled in the art recognizes that Hadamard schemes with other numbers of wavelengths are equally suitable for the present invention.

Another advantage of solid-state light sources is that many types (e.g. Laser diodes and VCSEL's) emit a narrow range of wavelengths (which in part determines the effective resolution of the measurement). Consequently, shaping or narrowing the emission profile of solid-state light sources with optical filters or other approaches is not required as they are already sufficiently narrow. This can be advantageous due to decreased system complexity and cost. Furthermore, the emission wavelengths of some solid-state light sources, such as diode lasers and VCSEL's, are tunable over a range of wavelengths via either the supplied drive current, drive voltage, or by changing the temperature of the solid-state light source. The advantage of this approach is that if a given measurement requires a specific number of wavelengths, the system can achieve the requirement with fewer discrete solid-state light sources by tuning them over their feasible ranges. For example, if measurement of a noninvasive property required twenty wavelengths, ten discrete diode lasers or VCSEL's might be used with each of the ten being tuned to two different wavelengths during the course of a measurement. In this type of scheme, a Fourier or Hadamard approach remains appropriate by changing the modulation frequency for each tuning point of a solid-state light source or by combining the modulation scheme with a scanning scheme. Furthermore, if the wavelength of emission for a given laser drifts or changes over time, the tuning properties of the diode laser allow it to be returned to its target wavelength of emission by changing its drive current/voltage, temperature, or a combination thereof.

Analyte properties can be measured at a variety of wavelengths spanning the ultraviolet and infrared regions of the electromagnetic spectrum. For in vivo measurements in skin, such as alcohol or substances of abuse, the near infrared (NIR) region of 1,000 nm to 2,500 nm region can be important due to the sensitivity and specificity of the spectroscopic signals for the analyte of interest as well as other chemical species (e.g. water) that are present in human skin. Furthermore, the absorptivities of the analytes are low enough that the near infrared light can penetrate a few millimeters into the skin where the analytes of interest reside. The 2,000 nm to 2,500 nm wavelength range can be of particular utility as it contains combination bands rather than the weaker, less distinct overtones encountered in the 1,000 to 2,000 nm portion of the NIR.

In addition to the commonly available LED's, VCSEL's, and diode lasers in the visible region of the spectrum, there are solid-state light sources available with emission wavelengths throughout the NIR region (1,000 to 2,500 nm). These solid-state light sources are suitable for the disclosed analyte and biometric property measurement systems. Some examples of available NIR solid-state light sources that are VCSEL's produced by Vertilas GmbH, and the VCSEL's, quantum cascade lasers, laser diodes available from Laser Components GmbH, or lasers and diodes available from Roithner Laser, Sacher Lasertechnik, NanoPlus, Mitsubishi, Epitex, Dora Texas Corporation, Microsensor Tech, SciTech Instruments, Laser 2000, Redwave Labs, and Deep Red Tech. These examples are included for demonstrative purposes and are not intended to be limiting of the types of solid-state light sources suitable for use with the present invention.

A microcontroller cab be used to control each solid-state light source in an embodiment of the illumination/modulation subsystem 100. The microcontroller can be programmed to include the defined states in the Hadamard or other encoding scheme (e.g. the individual solid-state light sources are turned off and on according to the set of states defined by the scheme). The microcontroller can then cycle through each of the states with a predetermined measurement time at each state. There is no restriction that the measurement time of each state must be equal. In addition to "off" and "on" control of each solid-state light source, the microcontroller can also provide global (across all solid-state light sources) and individual set points for solid-state light source temperature and drive current/voltage. Such embodiments enable controlled wavelength tuning and/or improved stability of the illumination/modulation subsystem 100. One skilled in the art recognizes alternatives to microcontrollers are available that serve the substantially the same function as the described microcontroller embodiments.

Measurement Resolution and Resolution Enhancement

In a dispersive spectrometer the effective resolution of a spectroscopic measurement is often determined by the width of an aperture in the system. The resolution limiting aperture is often the width of the entrance slit. At the focal plane where light within the spectrometer is detected, multiple images of the slit are formed, with different wavelengths located at different spatial locations on the focal plane. Thus, the ability to detect one wavelength independent of its neighbors is dependent on the width of the slit. Narrower widths allow better resolution between wavelengths at the expense of the amount of light that can be passed through the spectrometer. Consequently, resolution and signal to noise ratio generally trade against each other. Interferometric spectrometers have a similar trade between resolution and signal to noise ratio. In the case of a Michelson interferometer the resolution of the spectrum is in part determined by the distance over which a moving mirror is translated with longer distances resulting in greater resolution. The consequence is that the greater the distance, the more time is required to complete a scan.

In the case of the measurement systems, the resolution of the spectrum is determined by the spectral width of each of the discrete solid-state light sources (whether a different solid-state light source, one tuned to multiple wavelengths, or a combination thereof). For measurements of analyte properties requiring high resolution, a diode laser or other suitable solid state laser can be used. The widths of the laser's emission can be very narrow, which translates into high resolution. In measurement applications where moderate to low resolution are required, LED's can be suitable as they typically have wider emission profiles (the output intensity is distributed across a wider range of wavelengths) than solid state laser alternatives.

The effective resolution of solid-state light sources can be enhanced through the use, or combination of, different types of optical filters. The spectral width of a solid-state light source can be narrowed or attenuated using one or more optical filters in order to achieve higher resolution (e.g. a tighter range of emitted wavelengths). Examples of optical filters that are contemplated in embodiments of the present invention include, but are not limited to: linearly variable filters (LVF's), dielectric stacks, distributed Bragg gratings, photonic crystal lattice filters, polymer films, absorption filters, reflection filters, etalons, dispersive elements such as prisms and gratings, and quantum dot filters.

Another means for improving the resolution of measurements obtained from embodiments of the present invention is deconvolution. Deconvolution, and other similar approaches, can be used to isolate the signal difference that is present between two or more overlapping broad solid-state light sources. For example, two solid-state light sources with partially overlapping emission profiles can be incorporated into a measurement system. A measurement can be acquired from a sample and a spectrum generated (via a Hadamard, Fourier transform, or other suitable transform). With knowledge of the emission profiles of the solid-state light sources, the profiles can be deconvolved from the spectrum in order to enhance the resolution of the spectrum.

Stabilization and Control of Solid-State Light Source Wavelength and Intensity

The peak emission wavelength of solid-state light sources, particularly lasers, can be influenced by changing the thermal state or electrical properties (e.g. drive current or voltage) of the solid-state light source. In the case of semiconductor lasers, changing the thermal state and electrical properties alters the optical properties or physical dimensions of the lattice structure of the semiconductor. The result is a change in the cavity spacing within the device, which alters the peak wavelength emitted. Since solid-state light sources exhibit these effects, when they are used in spectroscopic measurement systems the stability of the peak wavelength of emission and its associated intensity can be important parameters. Consequently, during a measurement control of both the thermal state and electrical properties of each solid-state light source can be advantageous in terms of overall system robustness and performance. Furthermore, the change in optical properties caused by thermal state and electrical conditions can be leveraged to allow a single solid-state light source to be tuned to multiple peak wavelength locations. This can result in analyte property measurement systems that can measure more wavelength locations than the number of discrete solid-state light sources which can reduce system cost and complexity.

Temperature stabilization can be achieved using multiple approaches. In some embodiments, a solid-state light source or solid-state light sources can be stabilized by raising the temperature above (or cooling below) ambient conditions with no additional control of the temperature. In other embodiments, the solid-state light source or solid-state light sources can be actively controlled to a set temperature (either cooled or heated) using a control loop. For example, a temperature loop circuit suitable for an embodiment of the present invention may include a TE-Cooled VCSEL Package including a thermo-electric cooler and a precision thermistor. The precision thermistor may be connected to a Wheatstone bridge, which may be connected to a current drive circuit configured to drive the thermo-electric cooler.

Figure 3:
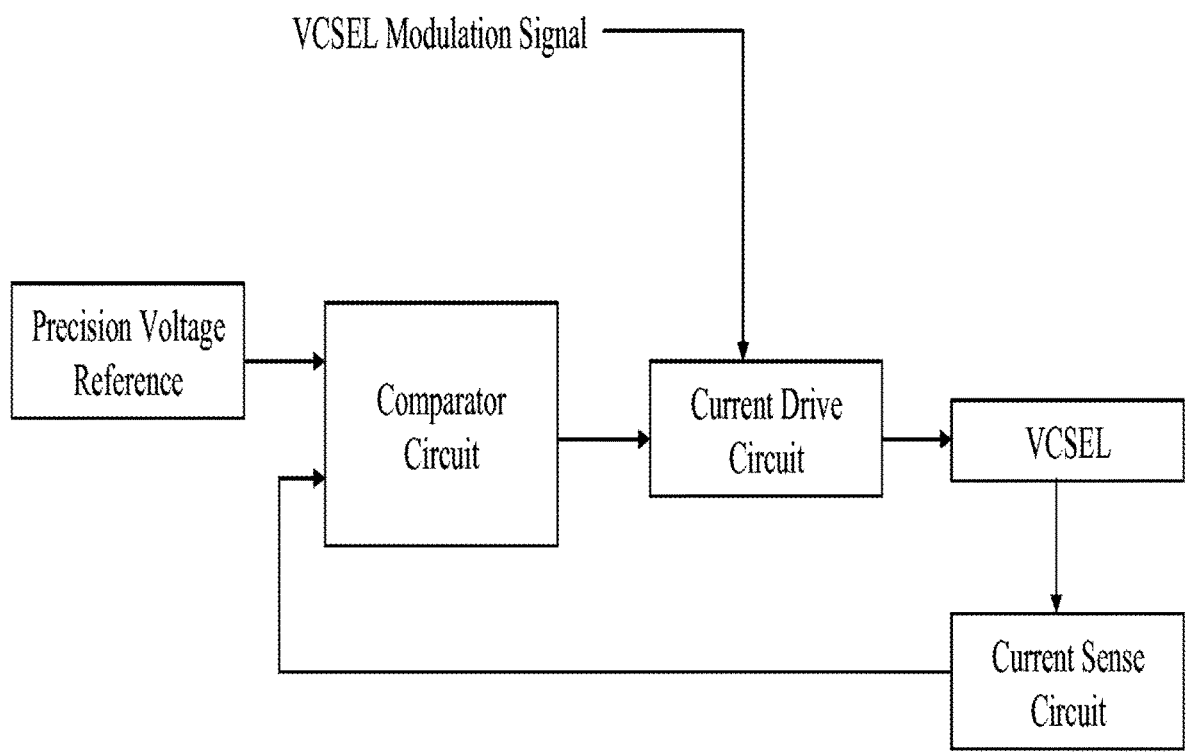
FIG. 3 is an embodiment of an electronic circuit designed to control the drive current of a solid-state light source including means for turning the light source on and off.
Figure 4:
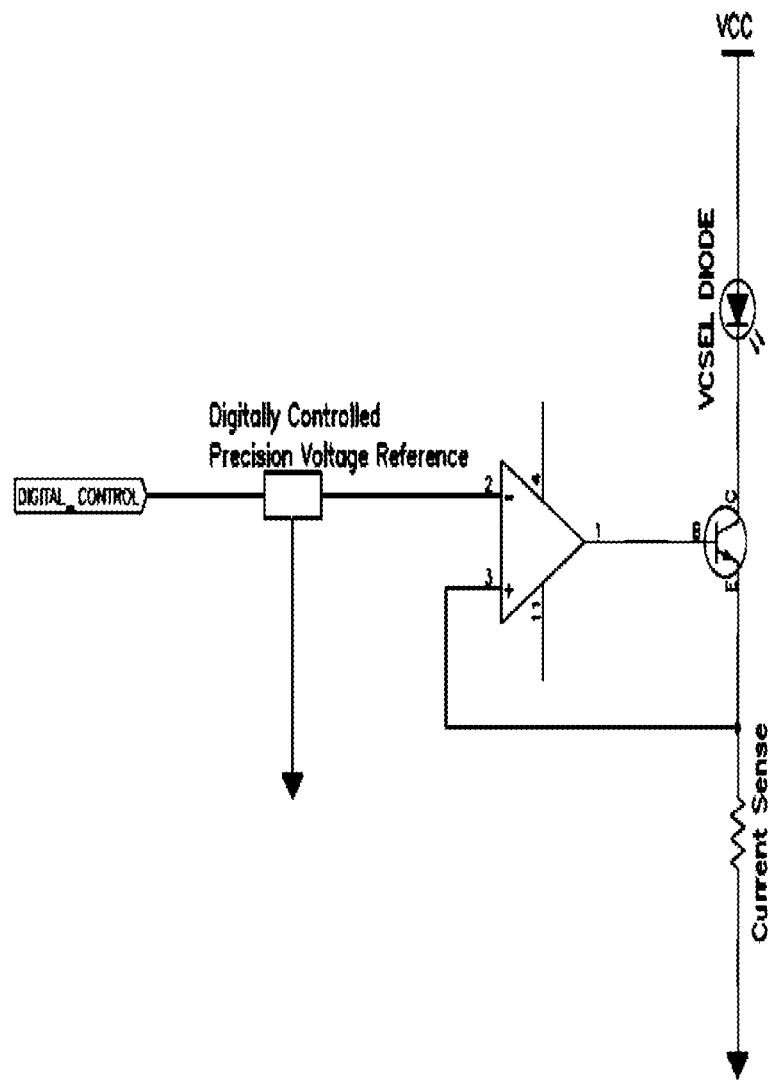
FIG. 4 is an embodiment of an electronic circuit designed to control the drive current of a solid-state light source including means for turning the light source on and off and altering the desired drive current.

The electrical properties of solid-state light sources also influence the emission profile (e.g. wavelength locations of emission) of solid-state light sources. It can be advantageous to stabilize the current and/or voltage supplied to the solid-state light source or solid-state light sources. For example, the peak emission of VCSEL's and many diode lasers depend on drive current. For embodiments where the stability of the peak wavelength is important, the stability of the drive current becomes an important figure of merit. In such cases, an electronic circuit can be designed to supply a stable drive current to the VCSEL or diode laser. The complexity and cost of the circuit can depend on the required stability of the drive current. FIG. 3 shows a current drive circuit suitable for use with an embodiment of the present invention. One skilled in the art recognizes that alternative embodiments of current control circuits are known in the art and can also be suitable for the present invention. Furthermore, some solid-state light sources require control of the drive voltage, rather than drive current; one skilled in the art recognizes that electronics circuits designed to control voltage rather than current are readily available.

In some embodiments, a single solid-state light source, such as a VCSEL or diode laser, is tuned to multiple wavelengths during the course of a measurement. In order to achieve the tuning of the solid-state light sources, the circuit shown in FIG. 3 can be modified to include the control of the temperature set point and current, respectively. In some embodiments, either tuning temperature or drive current/voltage can be sufficient to realize the desired tuning of the peak emission wavelength. In other embodiments, control of both the temperature and drive current/voltage can be required to achieve the desired tuning range.

Furthermore, optical means for measuring and stabilizing the peak emission wavelength can also be incorporated into the systems described in connection with embodiments of the present invention. A Fabry-Perot etalon can be used to provide a relative wavelength standard. The free spectral range and finesse of the etalon can be specified to provide an optical pass band that allows active measurement and control of the VCSEL or diode laser peak wavelength. An example embodiment of this etalon uses a thermally stabilized, flat fused-silica plate with partially mirrored surfaces. For systems where each VCSEL or diode laser is required to provide multiple wavelengths, the free spectral range of the etalon can be chosen such that its transmission peaks coincide with the desired wavelength spacing for tuning. One skilled in the art will recognize that there are many optical configurations and electronic control circuits that are viable for this application. An alternate wavelength encoding scheme uses a dispersive grating and a secondary array detector to encode the VCSEL or diode laser wavelength into a spatial location on the array. For either the dispersive or the etalon based schemes, a secondary optical detector that has less stringent performance requirements than the main optical detector can be used. Active control can reduce the stability requirements of the VCSEL temperature and current control circuits by allowing real time correction for any drift.

Figure 5:
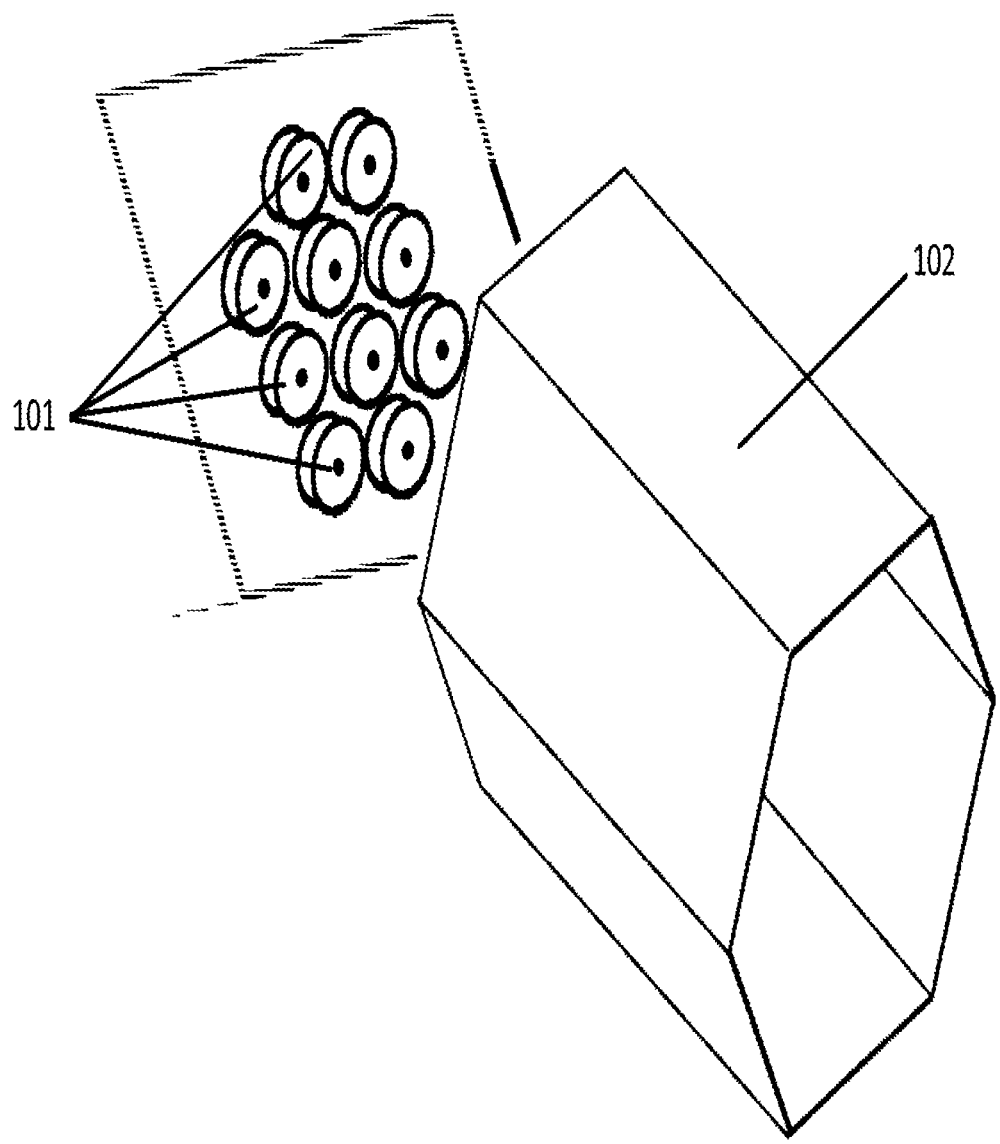
FIG. 5 is an embodiment of the Illumination/Modulation Subsystem comprising multiple individual solid-state light sources arranged in an array whose outputs are introduced to a hexagonal cross section internally reflective light homogenizer.

Embodiments and Approaches for Multi-Wavelength Illumination/Modulation Subsystems FIG. 5 shows an example embodiment of the Illumination; Modulation subsystem 100 where 10 individual solid-state light sources 101 are arranged in a planar array. In some embodiments of FIG. 5, the solid-state light sources 101 are individually housed in their own packages such as TO-9, TO-56, or other standard packages. These packages can be sealed with transmissive windows or unsealed. In other embodiments, the solid-state light sources 101 can be placed onto a common carrier and the resulting assembly placed into a housing. The housing can be sealed or unsealed. The temperature of each solid-state light source 101 can be controlled independently, where each solid-state light source 101 has its own means for controlling temperature, or collectively using a single means for controlling temperature.

The light emitted by the solid-state light sources 101 is collected and homogenized by the homogenizer 102 (FIG. 5) and delivered to the input of the Sampling Subsystem 200. In some embodiments of the present invention, the packing density (how close the individual solid-state light sources 101 can be placed to each other) is disadvantageous and limits the number of solid-state light sources 101 that can be used. In such embodiments, a means for condensing the light emitted by the solid-state light sources 101 into a smaller area can be advantageous. Means for efficient condensing of the light and coupling to the Sampling Subsystem 200 are discussed in subsequent paragraphs.

Figure 6:
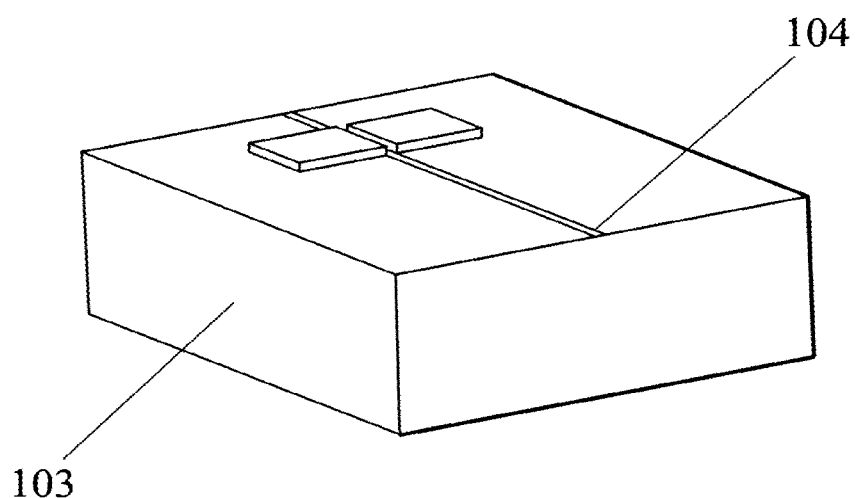
FIG. 6 is an embodiment of a single laser emitter in a semiconductor chip.

In some embodiments, an alternative to the planar array of individual solid-state light sources is employed. An example of an individual solid-state light source 101, a laser diode, is shown in FIG. 6 and is comprised of the semiconductor chip 103 and a laser emission aperture 104.

Figure 7:
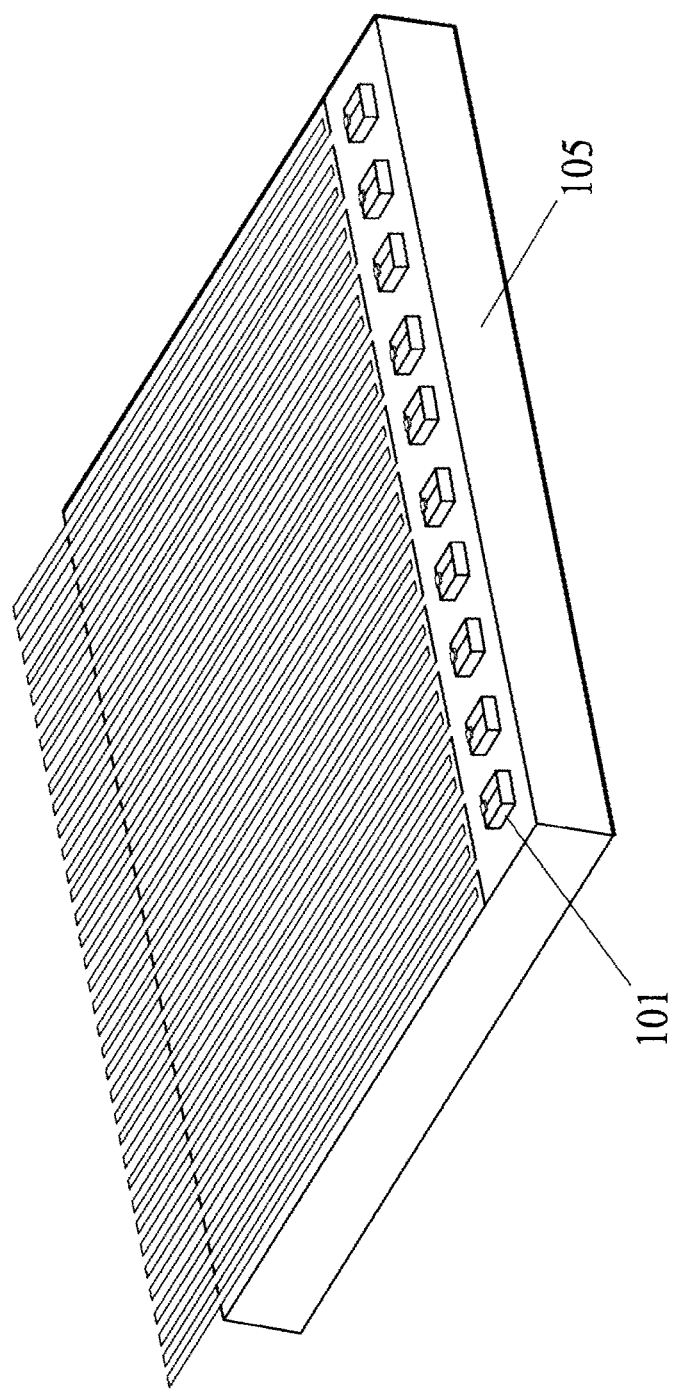
FIG. 7 is an embodiment of the Illumination/Modulation Subsystem where multiple laser emitters are mounted to a common carrier.

In another embodiment, a cumulative number of individual solid-state light sources 101 are divided into one or more groups. Each solid-state light source 101 within the one or more groups is mounted onto a common carrier 105 (one carrier per group) with a predefined spacing between the other solid-state light sources 101. This approach is referred to as a light source "carrier" 104 and is depicted in FIG. 7. The carrier 105 may be formed, for example, from ceramic. In this embodiment, different wavelengths can come from different sources, for example, different wafers that are diced into laser chips. Multiple laser chips may form a solid-state light source 101. This allows multiple wavelengths to be accommodated by combining lasers from several sources (wafers, different vendors, etc.). The advantages of this approach are a fewer number of solid-state light source assemblies and a known relationship of solid-state light source locations relative to each other. This in turn allows the potential for a reduced number of temperature controlled packages relative to controlling individual solid-state light sources. Furthermore, as the solid-state light sources within the package are in fixed and known locations relative to each other, more efficient light coupling approaches are enabled.

In other embodiments, multiple solid-state light sources are located within the same physical semiconductor in order to further reduce the number of parts in the illumination/modulation subsystem 100. In such embodiments, the solid-state light sources 101 within a semiconductor can be the same wavelength, different wavelengths, or a combination thereof. When the solid-state light sources 101 are laser diodes or other solid state lasers, these embodiments are referred to as "laser bars" 106. Similar to the carrier embodiments, an advantage of the laser bar 106 is the very well characterized and specified locations of each solid-state light source 101. Overall, the laser bar 106 results in a significant reduction in the number of individual semiconductors, the total number of system components, and therefore subsystem complexity and cost.

Figure 8:
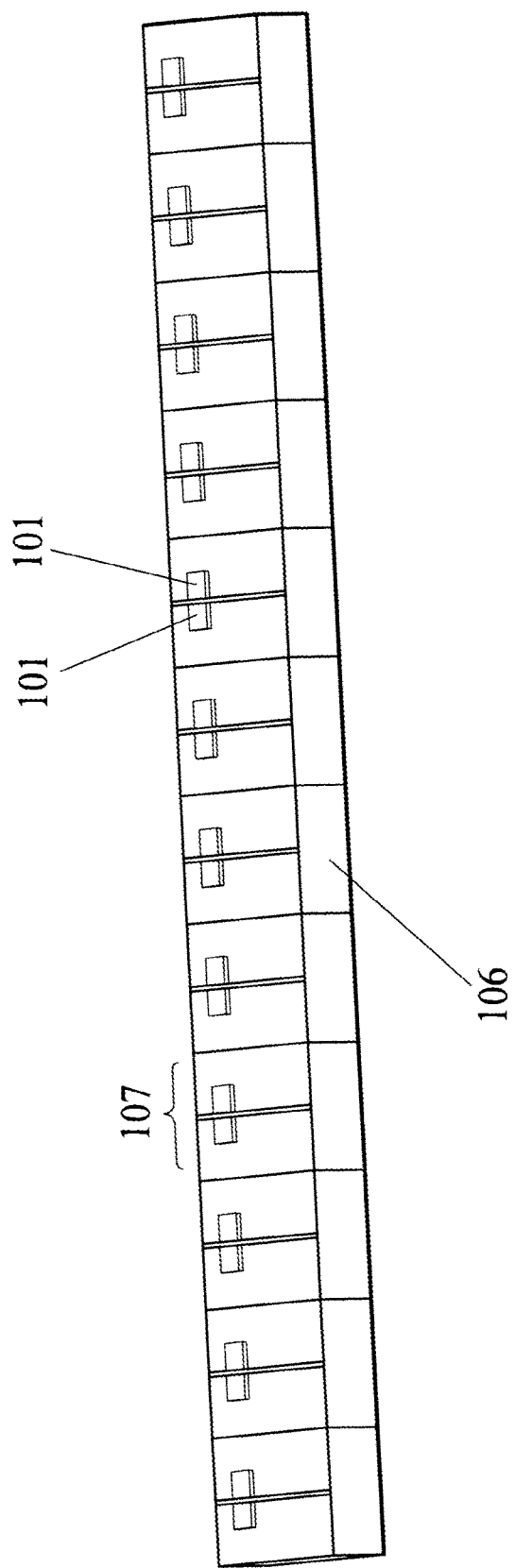
FIG. 8 is an embodiment of the Illumination/Modulation Subsystem that depicts a laser bar comprised of a single semiconductor chip that contains 24 emitters (12 different wavelengths, 2 emitters per wavelength).

Multiple solid-state light sources 101 of the same wavelength can be used to increase optical power at that wavelength. In some embodiments, solid-state light sources 101 of the same wavelength are adjacent to, and very near each other in order to allow efficient light coupling. FIG. 8 shows a laser bar 106 comprised of 12 groups of 2 laser diodes (24 total laser emitters). The two lasers forming a pair 107 have a common wavelength and each pair 107 has a different wavelength than the other pairs (12 distinct wavelengths across the bar 106 in this embodiment). Each pair 107 is spaced 480 microns from adjacent pairs 107 and the spacing between the two emitters 101 of a pair 107 is 5 microns. In embodiments employing DFB diode lasers, the different wavelengths are achieved using a single semiconductor chip by applying gratings with different pitches to each pair 107. The emission of DFB lasers is generally single mode, which is advantageous in some embodiments. One skilled in the art recognizes the large number of permutations of total solid-state light sources 101 and their wavelengths of emission that are encompassed by the carrier 105 and bar embodiments 106. The embodiments disclosed herein are not intended to be limiting to the scope of the present invention.

In some embodiments, dedicated thermoelectric coolers for each emitter can be cost and size prohibitive and a single global cooler or temperature control may not provide sufficient local temperature control. In such cases, local temperature control within a semiconductor can be achieved using a local heating provision near the solid-state light source. An embodiment of the heating provision is a local resistor near the solid-state light source what allows applied current to be converted into local heat. This approach allows a single temperature control provision to apply the majority of the heating/cooling load while the local provisions allow fine tuning for each solid-state light source. This allows both a higher degree of stability as well as the ability to tune emission wavelengths of each laser by changing the local temperature.

Strategies for Efficient Coupling of Solid-State Light Sources to the Sampling Subsystem Whether the solid-state light sources of an embodiment reside in individual packages or are grouped onto a smaller number of carriers or bars, the density of the solid-state light source emission apertures is not ideal as there is always a finite distance between neighboring solid-state light sources. This spacing can, for example, be driven by the sizes of the individual solid-state light source packages as well as the need to allow for a finite spacing to dissipate heat. In some embodiments of the present invention, the density of the emission apertures is not a concern and the output of the individual solid-state light sources can be collected, combined, and homogenized using a light homogenizer whose cross section is sufficiently large to encompass all solid-state light source emission apertures in the Illumination/Modulation Subsystem 100. However, in this case the photon flux at the output of the light homogenizer is lower than ideal as the light from the solid-state light sources has been substantially uniformly distributed across the entire area of the cross section. This corresponds to a reduction in the etendue of the system, which can be disadvantageous in some embodiments.

Figure 9:
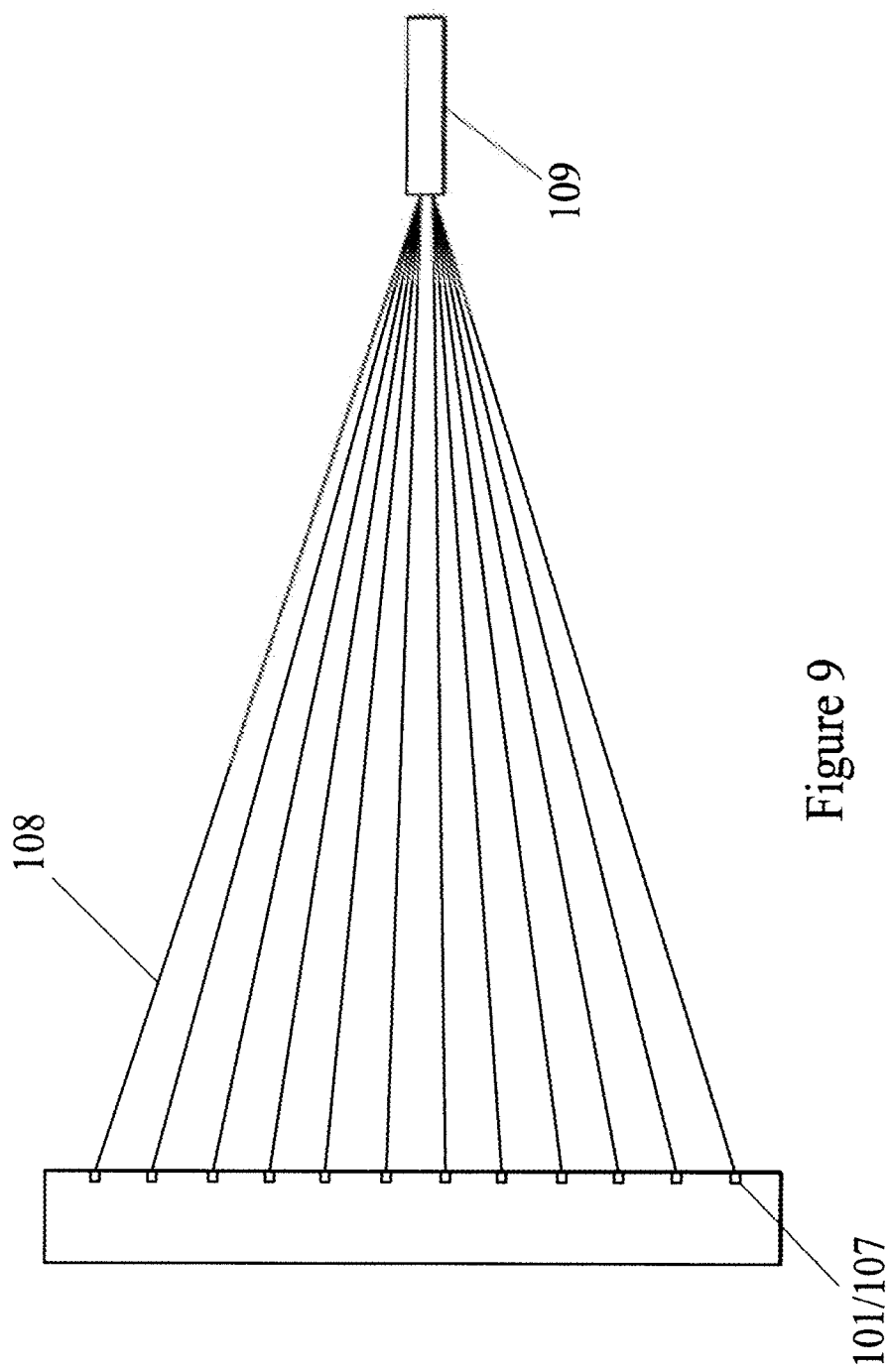
FIG. 9 is a schematic view of an embodiment of a fiber optic coupler that collects light emitted from each pair of emitters in the laser bar embodiment shown in FIG. 8 and combines the individual optical fibers into an output bundle or cable.

In embodiments where the reduction in etendue should be minimized, there are multiple strategies for more efficiently combining the outputs of the individual solid-state light source emission apertures. Several of the embodiments of the present invention incorporate optical fibers 108 as a means for collecting light from a solid-state light source 101 or a pair of solid-state light sources 107 and combining it with the light collected from the other solid-state light sources 101 or pairs of solid-state light sources 107 in the system (see FIG. 9). A plurality of individual optical fibers 108 may be bundled into a cable 109. In one embodiment, illustrated in FIG. 13, a fiber 108 collects light from each of the twelve solid-state light sources 101 or pairs of solid-state light sources 107. The twelve fibers 108 can be bundled into a cable 109. The emission apertures of many solid-state light sources can be on the order of a few microns in diameter. Some of the embodiments of the present invention can use large core multi-mode optical fiber (in contrast to small core, single mode fibers often used in telecommunications). The large fiber diameter relative to the small diameter of the emission aperture allows for an optical fiber to collect the light from an emission aperture with an alignment tolerance of tens of microns in all dimensions. Depending on the spacing of emission apertures and the size of the optical fiber 108, light from more than one aperture can be collected by a given optical fiber (see FIG. 9).

The advantage of such an approach is that it allows the outputs of any number of solid-state light sources to be combined by using an equivalent or smaller number of optical fibers. The opposing ends of the optical fibers can then be combined into a bundle. In some embodiments, the bundle is a circular hex-pack. For a given number of fibers of a given diameter, this configuration represents the smallest cross-sectional area and thus maintains the greatest photon flux and etendue. Furthermore, the optical fibers allow linear or other geometric arrangements of solid-state light sources (e.g. such as laser bars) to be fabricated while retaining the ability to combine their outputs into a small area aperture which allows for efficient coupling of the collected light to the Sampling Subsystem 200. A laser bar assembly may comprise a laser bar 106, ceramic carrier 105 with electrical contacts, an optical fiber coupler (not illustrated), a copper micro bench (not illustrated), and a thermo electric cooler (not illustrated). The assembly can be housed in a hermetically sealed package such as an industry standard butterfly package. In some embodiments, a light homogenizer can be placed at the output of the bundle of optical fibers in order to spatially and/or angularly homogenize the outputs of the individual optical fibers. In such embodiments, the cross sectional area can be matched to the area of the bundle of optical fibers in order to minimize any reduction in photon flux and etendue. In some embodiments, the arrangement of optical fibers at the output bundle can be matched to the cross section of the light homogenizer (e.g. square, hexagonal, etc.).

Figure 10:
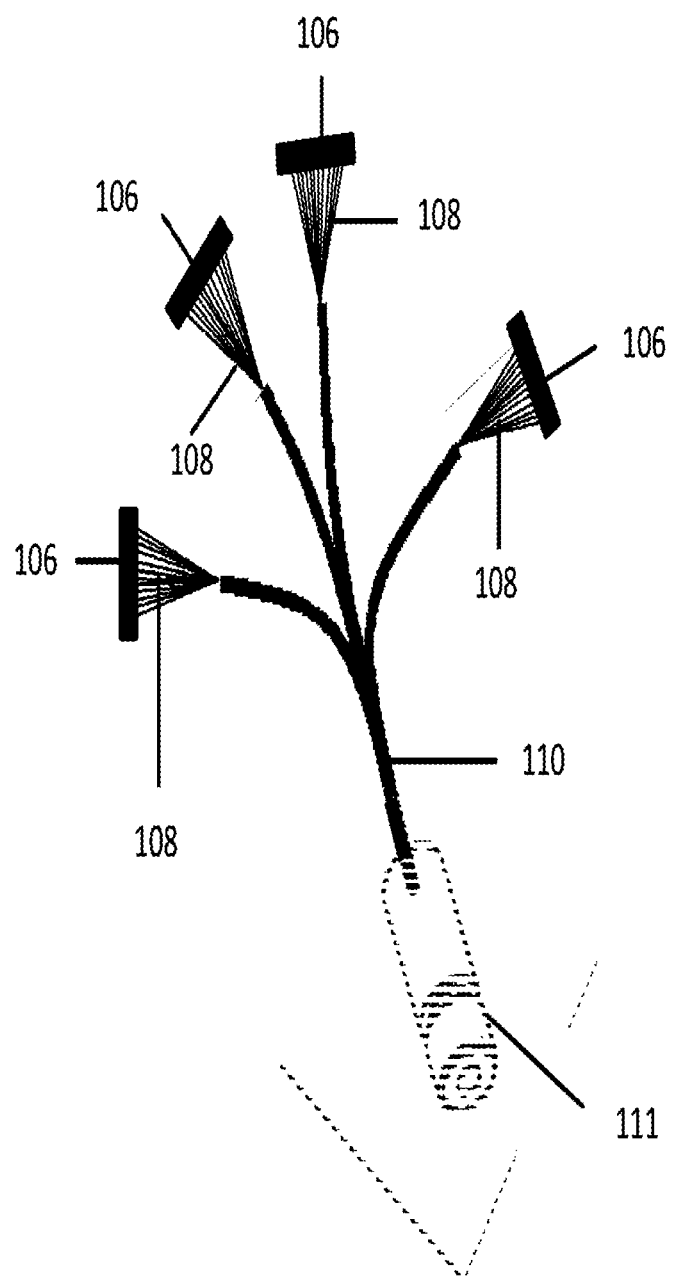
FIG. 10 is an embodiment that combines the outputs of 4 different fiber couplers into a single output aperture/bundle, where each couple is connected to a different laser bar.

Fiber optic coupling approaches also allow multiple assemblies with solid-state light source apertures to be combined into a single output aperture. For example, FIG. 10 shows 4 laser bars 106, each with 12 pairs of laser emitters 107 (see FIG. 8). A multimode optical fiber 110 is used to collect the light from each emitter pair 107 (48 total fibers 108). The opposing ends of the 48 fibers 108 are then combined into a circular hex pack output ferrule 111.

Figure 11:
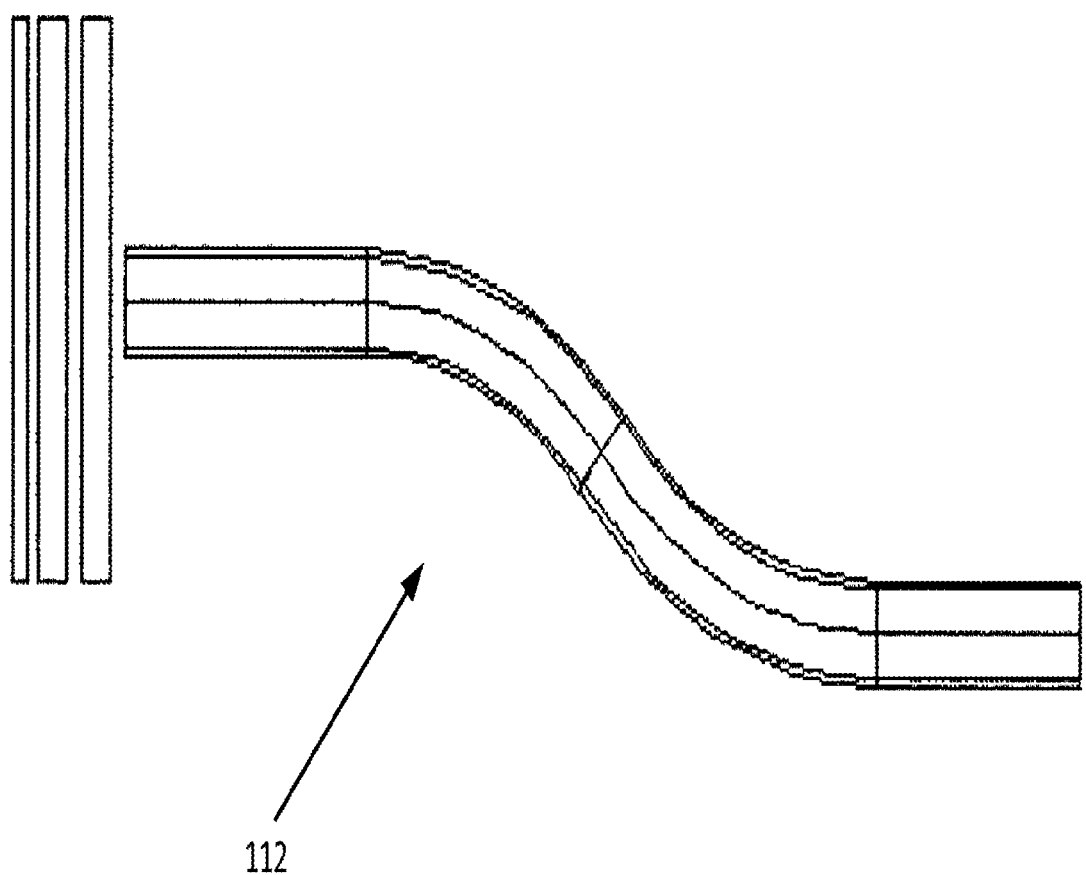
FIG. 11 is an example embodiment of a light homogenizer suitable for homogenizing the light from the illumination/modulation subsystem's output aperture/bundle.

Methods and Apparatuses for Homogenization of Illumination/Modulation Subsystem Output Light homogenizers 112 such as optical diffusers, light pipes, and other scramblers can be incorporated into some embodiments of the illumination/modulation subsystem 100 in order to provide reproducible and, preferably, uniform radiance at the input of the tissue sampling subsystem 200. FIG. 11 shows an example light homogenizer 112 comprising a ground glass diffuser and hexagonal cross section light pipe with 2 opposing bends. Uniform radiance can ensure good photometric accuracy and even illumination of the tissue. Uniform radiance can also reduce errors associated with manufacturing differences between solid-state light sources. Uniform radiance can be utilized in various embodiments of the present invention for achieving accurate and precise measurements. See, e.g., U.S. Pat. No. 6,684,099, incorporated herein by reference.

A ground glass plate is an example of an optical diffuser. The ground surface of the plate effectively scrambles the angle of the radiation emanating from the solid-state light source and its transfer optics. A light pipe can be used to homogenize the intensity of the radiation such that it is spatially uniform at the output of the light pipe. In addition, light pipes with a double bend will scramble the angles of the radiation. For creation of uniform spatial intensity and angular distribution, the cross section of the light pipe should not be circular. Square, hexagonal and octagonal cross sections are effective scrambling geometries. The output of the light pipe can directly couple to the input of the tissue sampler or can be used in conjunction with additional transfer optics before the light is sent to the tissue sampler. See, e.g., U.S. patent application Ser. No. 09/832,586, "Illumination Device and Method for Spectroscopic Analysis," incorporated herein by reference.

Sampling Subsystem

Figure 12:
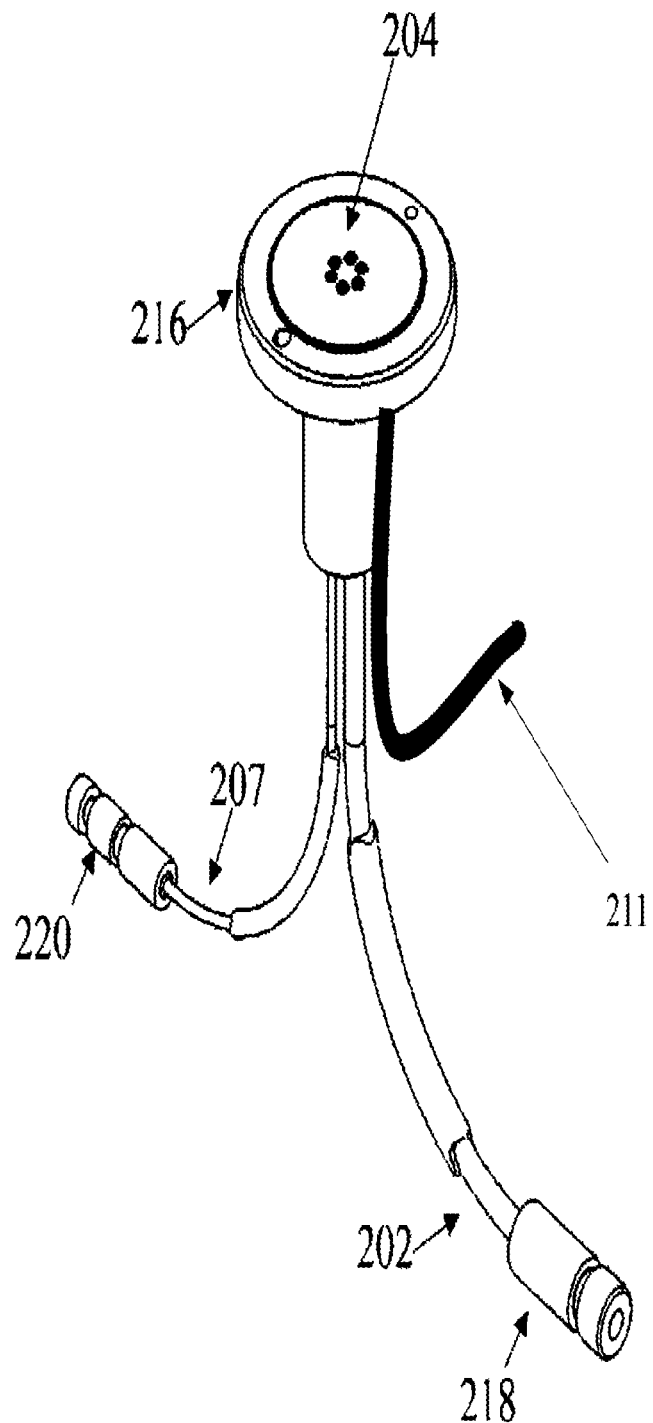
FIG. 12 is a perspective view of elements of a tissue sampling subsystem.

FIG. 1 indicates that the orientation of the tissue sampling subsystem 200 is between the illumination/modulation (100) and data acquisition (300) subsystems. Referring to FIG. 1, the tissue sampling subsystem 200 introduces radiation generated by the illumination/modulation subsystem 100 into the sample (e.g. tissue of the subject, collects a portion of the radiation that is not absorbed by the sample and sends that radiation to the optical detector in the data acquisition subsystem 300 for measurement. FIGS. 12 through 17 depict elements of an example tissue sampling subsystem 200. Referring to FIG. 12, the tissue sampling subsystem 200 has an optical input 202, a sampling surface 204 which forms a tissue interface 206 that interrogates the tissue and an optical output 207. The subsystem further includes an ergonomic apparatus 210, depicted in FIG. 13, which holds the sampling surface 204 and positions the tissue at the interface 206. An output 211 sends a signal to a processing circuit, which may be, for example, a microprocessor. In an exemplary subsystem, a device that thermostats the tissue interface is included and, in some embodiments. In other embodiments, an index matching fluid can be used to improve the optical interface between the tissue and sampling surface. The improved interface can reduce error and increase the efficiency, thereby improving the net attribute signal. See, e.g. U.S. Pat. Nos. 6,622,032, 6,152,876, 5,823,951, and 5,655,530, each of which is incorporated herein by reference.

Figure 14:
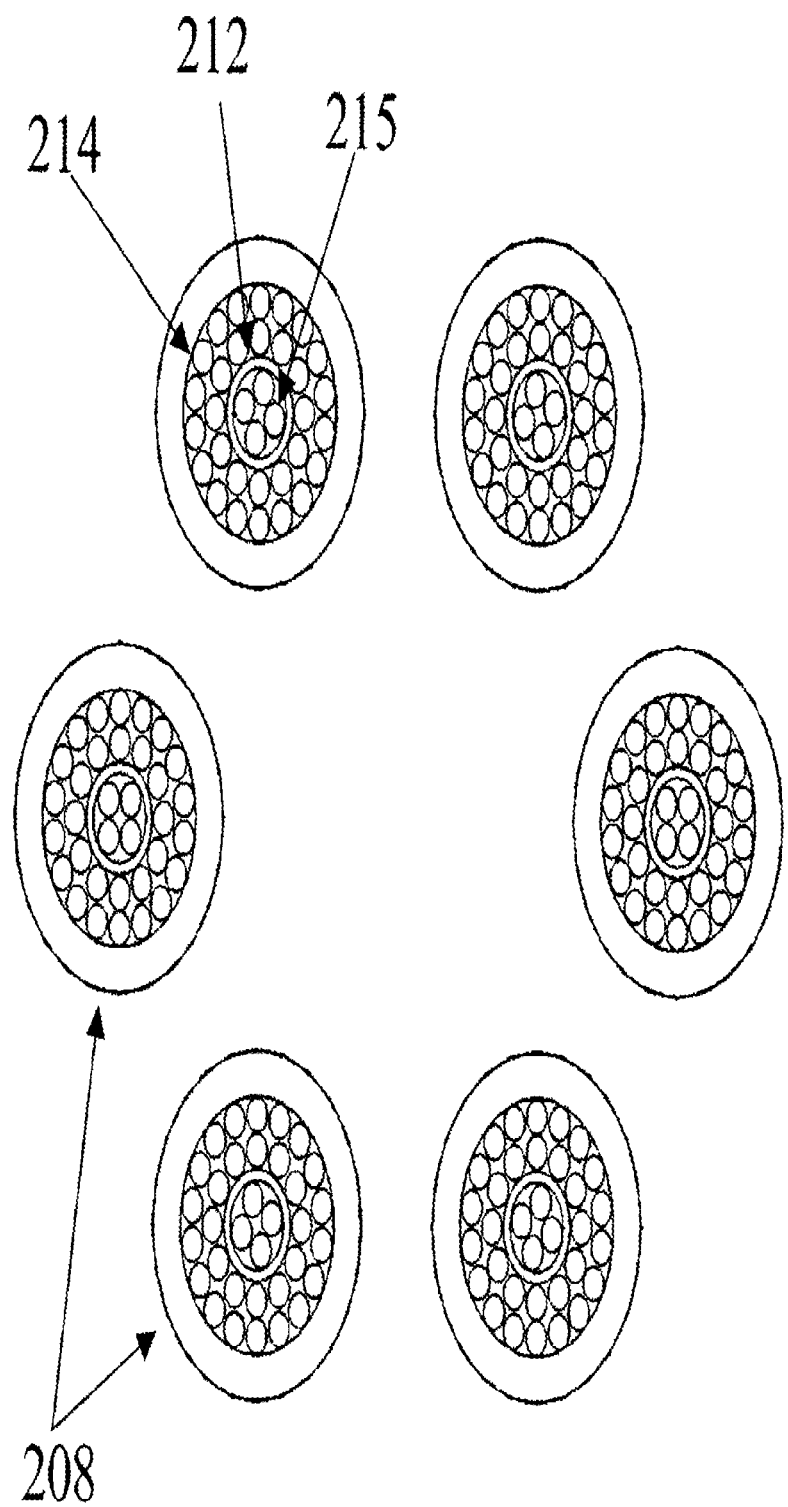
FIG. 14 is an alternative embodiment of the sampling surface of the tissue sampling subsystem.

The optical input 202 of the tissue sampling subsystem 200 receives radiation from the illumination/modulation subsystem 100 (e.g., light exiting a light pipe) and transfers that radiation to the tissue interface 206. As an example, the optical input can comprise a bundle of optical fibers that are arranged in a geometric pattern that collects an appropriate amount of light from the illumination/modulation subsystem. FIG. 14 depicts one example arrangement. The plan view depicts the ends of the input and output fibers in a geometry at the sampling surface including six clusters 208 arranged in a circular pattern. Each cluster includes four central output fibers 212 which collect diffusely reflected light from the tissue. Around each grouping of four central output fibers 212 is a cylinder of material 215 which ensures about a 100 µm gap between the edges of the central output fibers 212 and the inner ring of input fibers 214. The 100 µm gap can be important to measuring ethanol in the dermis. As shown in FIG. 14, two concentric rings of input fibers 214 are arranged around the cylinder of material 215. As shown in one example embodiment, 32 input fibers surround four output fibers.

Figure 15:
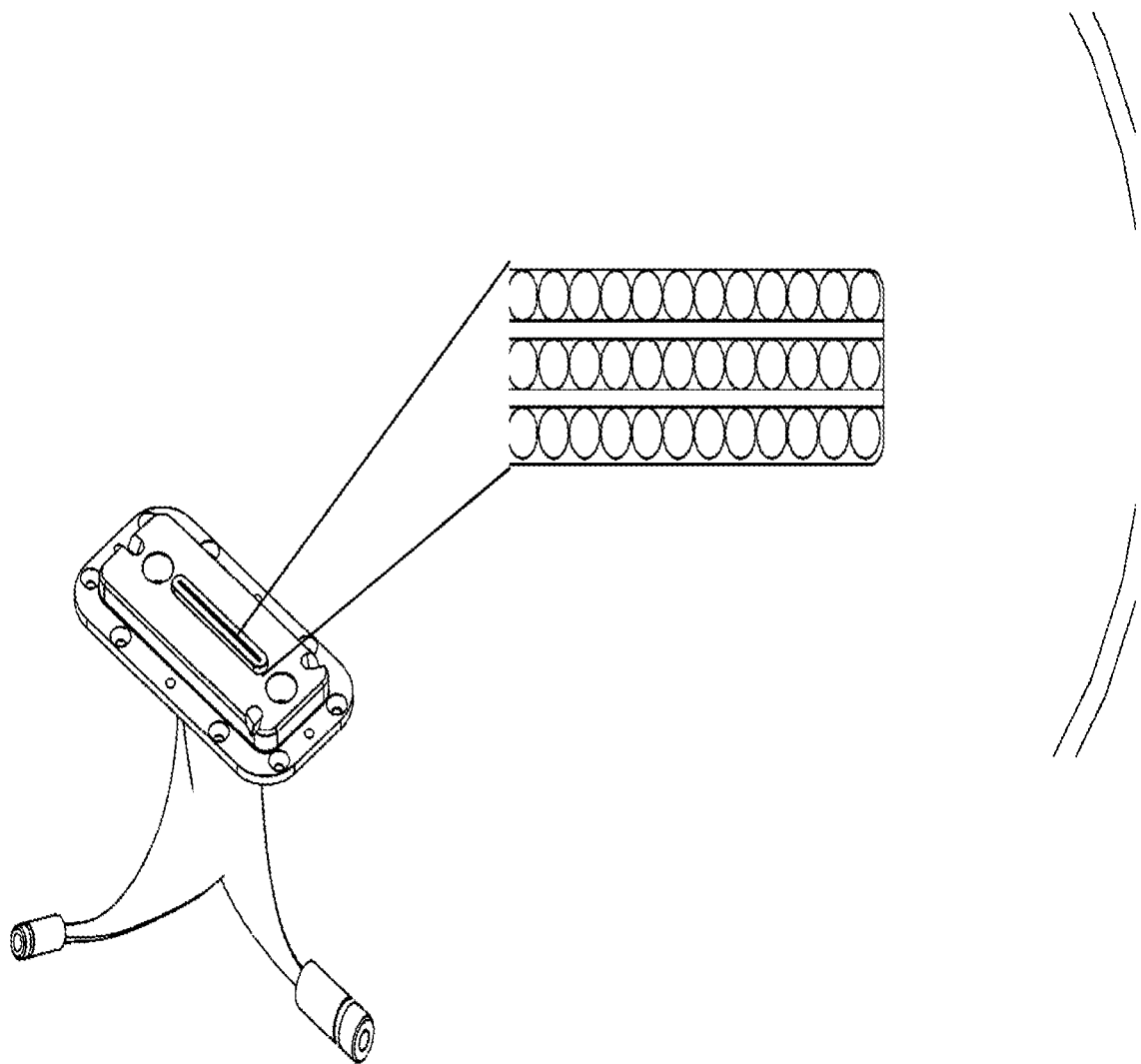
FIG. 15 is an alternative embodiment of the sampling surface of the tissue sampling subsystem.

FIG. 15 demonstrates an alternative to cluster geometries for the sampling subsystem. In this embodiment, the illumination and collection fiber optics are arranged in a linear geometry. Each row can be either for illumination or light collection and can be of any length suitable to achieve sufficient signal to noise. In addition, the number of rows can be 2 or more in order to alter the physical area covered by the sampling subsystem. The total number of potential illumination fibers is dependent on the physical size of emissive area of the solid-state light source subsystem (e.g. the area of the cross section of the fiber bundle or light homogenizer depending on the embodiment) and the area of each fiber. In some embodiments, multiple solid-state light source subsystems can be used to increase the number of illumination fibers. If the number of collection fibers results in an area larger than the photodetector of the Data Acquisition Subsystem (300), a light pipe or other homogenizer followed by an aperture can be used to reduce the size of the output area of the sampling subsystem. The purpose of the light pipe or other homogenizer is to ensure that each collection fiber contributes substantially equally to the light that passes through the aperture. In some embodiments, the light homogenizer can be omitted and the aperture used by itself. In other embodiments, the detector active area serves as the aperture (e.g. there is no distinct aperture). In this case, light that is not incident to the active area is effectively vignetted.

Figure 16:
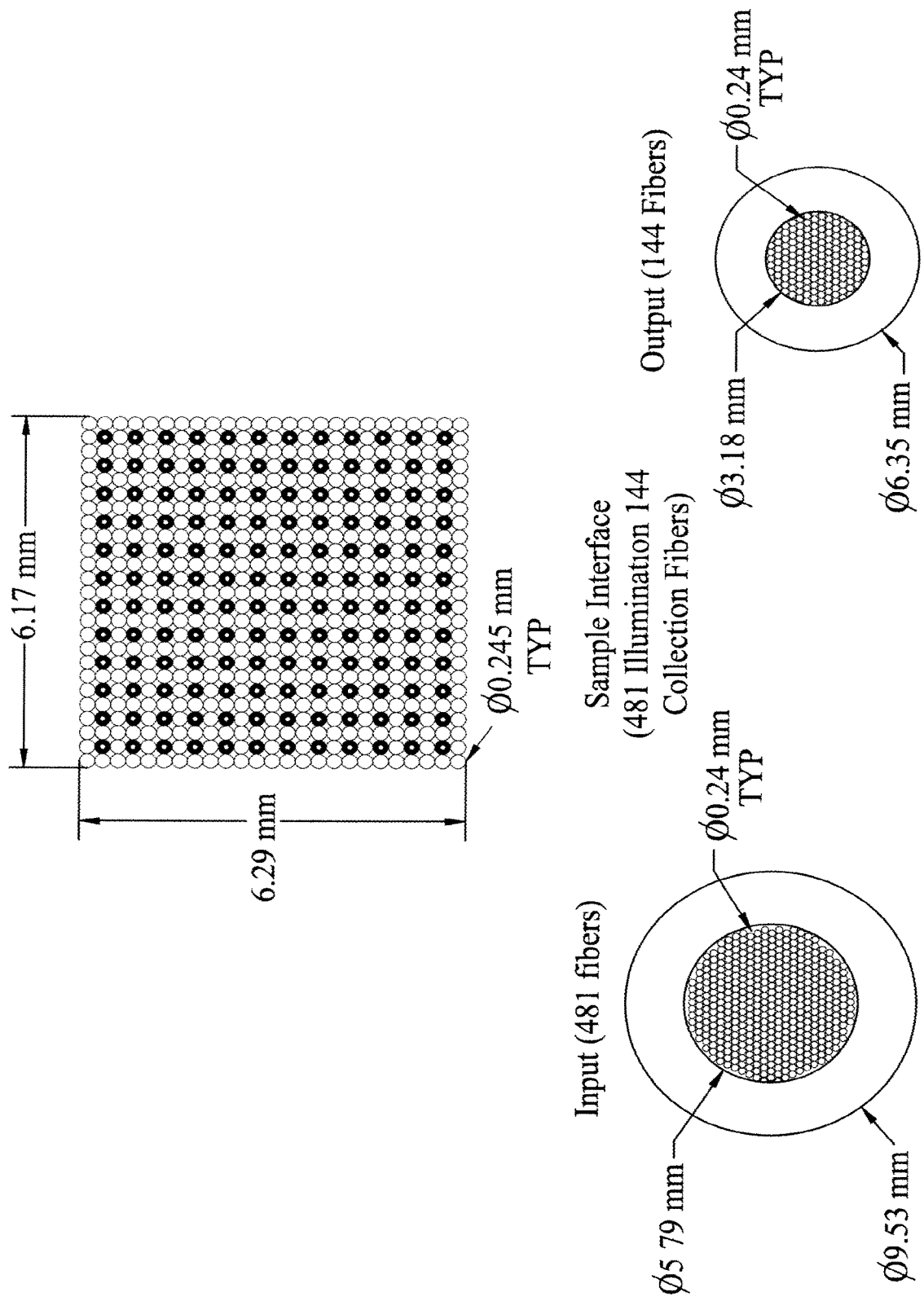
FIG. 16 is an alternative embodiment of the sampling surface of the tissue sampling subsystem that is optimized for the small emission area of some solid-state light source based Illumination/Modulation Subsystems.

In some embodiments of the Sampling Subsystem (200) of the present invention, the portion of the optical probe that interacts with the sample can be comprised of a stack of two or more linear ribbons of optical fibers. These arrangements allow the size and shape of the optical probe interface to be designed appropriately for the sample and measurement location (e.g. hand, finger) of interest. FIG. 16 shows an example embodiment of a sampling subsystem based on a linear stack off ribbons. Additional details regarding suitable embodiments for use in the present invention can be found in U.S. patent application Ser. Nos. 12/185,217 and 12/185,224, each of which is incorporated herein by reference.

In many embodiments of tissue analyte measurement devices, the photodetector is the limiting aperture of the system. In such systems, the throughput (and correspondingly the signal to noise ratio, SNR) of the system could be optimized by incorporating an optical probe design that illuminates a larger area of the sample (tissue) while collecting light from a smaller aperture that is consistent with the solid angle of acceptance of the photodetector. Referring to the optical probe design in FIG. 16, each collection fiber (black circles) is surrounded by 8 illumination fibers (white circles). For each collection fiber, this geometric difference in area allows each of the 8 illumination fibers to contribute to the light collected. The net effect of this approach is that it allows more light to be collected from the blackbody light source and delivered to the sample without being vignetted by the limiting aperture. This can be advantageous for light sources that inherently have large emissive areas (such as many blackbody emitters).

However, the photon flux of semiconductor light sources such as diode lasers can be much higher than that of blackbody light sources. As a result, a limited number of semiconductor light sources can deliver equivalent or superior photon flux with a smaller solid angle relative to their blackbody counter parts. This can result in the solid angle of the photon emission (the combined solid angles of all semiconductor light sources) being smaller than the solid angle of acceptance of the detector. In other words, the light source, rather than the photodetector, is the effective limiting aperture of the system. In such cases, optical probe designs such as those shown in FIG. 16 do not optimize the throughput and SNR of the systems. While such optical probes are suitable in some embodiments of the present invention, alternative designs can be preferable. In other embodiments, the number of illumination optical fibers may be less than or equal to the number of collection optical fibers. These optical probe designs have sampling surfaces that allow a small illumination area consistent with the smaller area of solid-state light source emission with a larger collection area consistent with the larger area of the photodetector. As a result, the overall efficiency of the system is improved.

Figure 17:
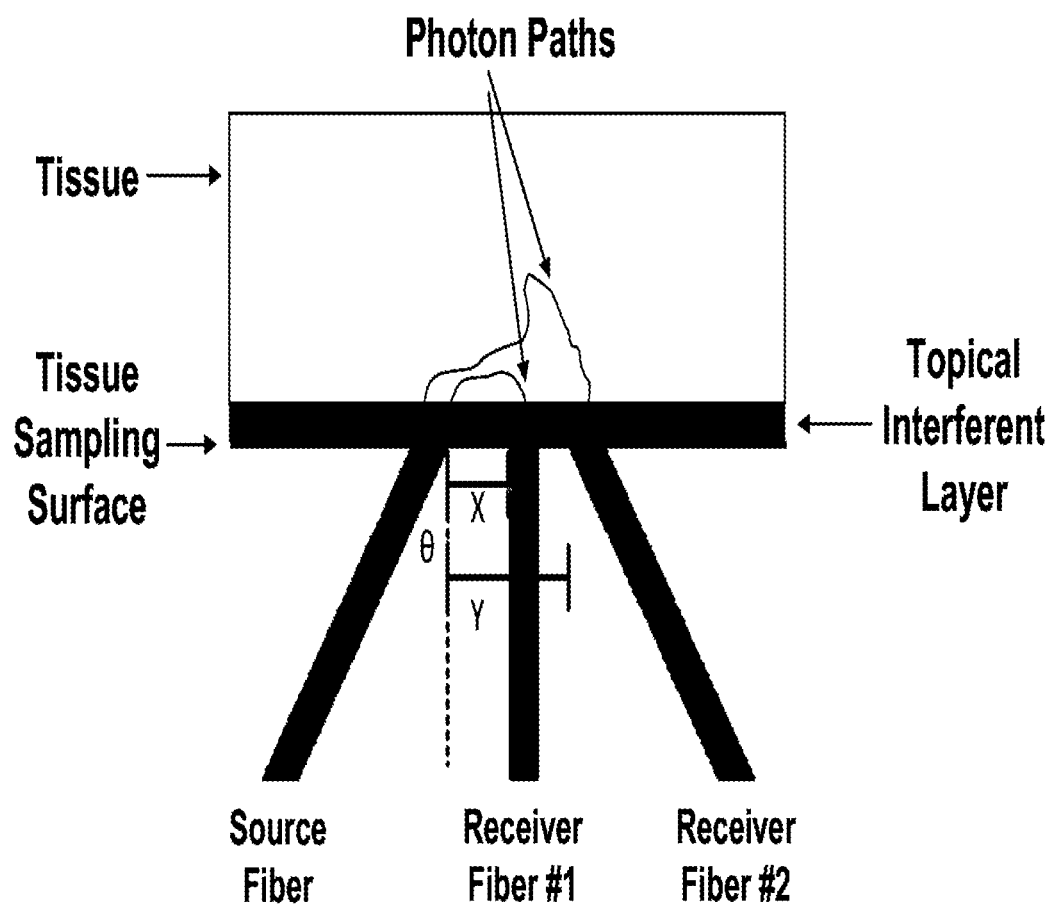
FIG. 17 is a diagramed view of the interface between the sampling surface and the tissue when topical interferents are present on the tissue.

The sampling subsystems can also use one or more channels, where a channel refers to a specific orientation of the illumination and collection fibers. An orientation is comprised of the angle of the illumination fiber or fibers, the angle of the collection fiber or fibers, the numerical aperture of the illumination fiber or fibers, the numerical aperture of the collection fiber or fibers, and the separation distance between the illumination and collection fiber or fibers. Multiple channels can be used in conjunction, either simultaneously or serially, to improve the accuracy of the noninvasive measurements. In on embodiment, a two channel sampling subsystem is utilized. In this example, the two channels are measuring the same tissue structure. Therefore each channel provides a measurement of the same tissue from a different perspective. The second perspective helps to provide additional spectroscopic information that helps to decouple the signals due to scattering and absorption. Referring to FIG. 17, the group of fibers (1 source, 1 receiver #1, and 1 receiver #2 in this example) can be replicated 1 to N times in order to increase the sampler area and improve optical efficiency. Each of the fibers can have a different numerical aperture and angle (θ). The distances between fibers, X and Y, determine the source-receiver separation. Furthermore, an additional source channel can be added that creates a 4-channel sampling subsystem. One skilled in the art recognizes the large number of possible variants on the number and relationship between channels.

In an experiment in which a multiple channel sampler was used for noninvasive glucose measurements, the results indicated that the combination of the two channels provides superior measurement accuracy when compared to either channel individually. While this example uses two channels, additional channels can provide additional information that can further improve the measurement.

Another aspect of a multiple channel sampling subsystem is the ability to improve detection and mitigation of topical interferents, such as sweat or lotion, present on the sample. FIG. 17 is a diagram of the multiple channel sampling subsystem in the presence of a topical interferent. FIG. 17 shows the sampling subsystem at the tissue interface, a layer of topical interferent, and the tissue. In this example the contribution to each channel's measurement due to the topical interferent is identical. This allows the potential to decouple the common topical interferent signal present in both channels from the tissue signal that will be different for the two channels.

Referring to FIG. 12, the clustered input and output fibers are mounted into a cluster ferrule that is mounted into a sampling head 216. The sampling head 216 includes the sampling surface 204 that is polished flat to allow formation of a good tissue interface. Likewise, the input fibers are clustered into a ferrule 218 connected at the input ends to interface with the illumination/modulation subsystem 100. The output ends of the output fibers are clustered into a ferrule 220 for interface with the data acquisition subsystem 300.

Alternatively, the optical input can use a combination of light pipes, refractive and/or reflective optics to transfer input light to the tissue interface. It is important that the input optics of the tissue sampling subsystem collect sufficient light from the illumination/modulation subsystem 100 in order to achieve an acceptable net attribute signal.

The tissue interface irradiates the tissue in a manner that targets the compartments of the tissue pertinent to the attribute of interest, and can discriminate against light that does not travel a significant distance through those compartments. As an example, a 100-µm gap between illumination and collection optical fibers can discriminate against light that contains little attribute information. In addition, the tissue interface can average over a certain area of the tissue to reduce errors due to the heterogeneous nature of the tissue. The tissue sampling interface can reject specular and short pathlength rays and it can collect the portion of the light that travels the desired pathlength through the tissue with high efficiency in order to maximize the net attribute signal of the system. The tissue sampling interface can employ optical fibers to channel the light from the input to the tissue in a predetermined geometry as discussed above. The optical fibers can be arranged in pattern that targets certain layers of the tissue that contain good attribute information.

The spacing, angle, numerical aperture, and placement of the input and output fibers can be arranged in a manner to achieve effective depth targeting. In addition to the use of optical fibers, the tissue sampling interface can use a non-fiber based arrangement that places a pattern of input and output areas on the surface of the tissue. Proper masking of the non-fiber based tissue sampling interface ensures that the input light travels a minimum distance in the tissue and contains valid attribute information. Finally, the tissue sampling interface can be thermostatted to control the temperature of the tissue in a predetermined fashion. The temperature of the tissue sampling interface can be set such that prediction errors due to temperature variation are reduced. Further, reference errors are reduced when building a calibration model. These methods are disclosed in U.S. patent application Ser. No. 09/343,800, entitled "Method and Apparatus for Non-Invasive Blood Analyte Measurement with Fluid Compartment Equilibration," which is incorporated herein by reference.

Figure 13:
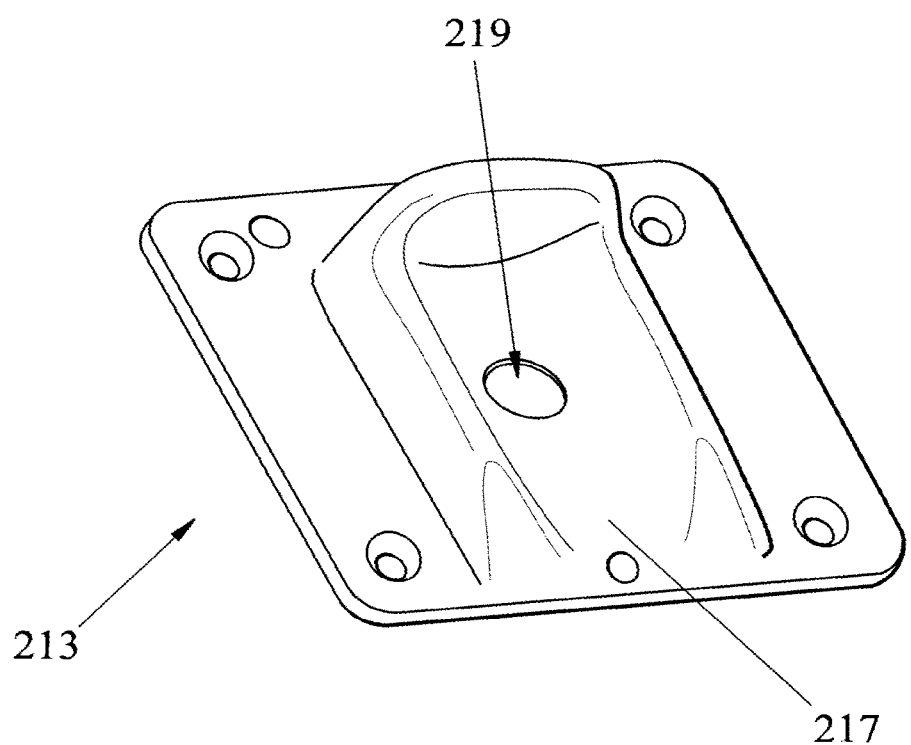
FIG. 13 is a plan view of the sampling surface of the tissue sampling subsystem, showing an arrangement of illumination and collection optical fibers.

The tissue sampling subsystem 200 can employ an ergonomic apparatus or guide 213 that positions the tissue over the sampling interface 204 in a reproducible manner. An example ergonomic apparatus 213 that guides the finger reproducibly to the sampling surface is depicted in FIG. 13. The ergonomic apparatus 213 includes a base 217 having an opening 219 there through. The opening 219 is sized for receiving the sample head 216 therein to position the sampling surface 204 generally coplanar with an upper surface of the base. Careful attention must be given to the ergonomics of the tissue sampling interface or significant sampling error can result. Alternate sites, for example the tops or palmar side of fingertips or the forearm can also be accommodated using variations of the systems described herein.

The output of the tissue sampling subsystem 200 transfers the portion of the light not absorbed by the tissue that has traveled an acceptable path through the tissue to the optical detector in the data acquisition subsystem 300. The output of the tissue sampling subsystem 200 can use any combination of refractive and/or reflective optics to focus the output light onto the optical detector. In some embodiments, the collected light is homogenized (see U.S. Pat. No. 6,684,099, Apparatus and Methods for Reducing Spectral Complexity in Optical Sampling, incorporated herein by reference) in order to mitigate for spatial and angular effects that might be sample dependent.

Data Acquisition Subsystem

Figure 18:
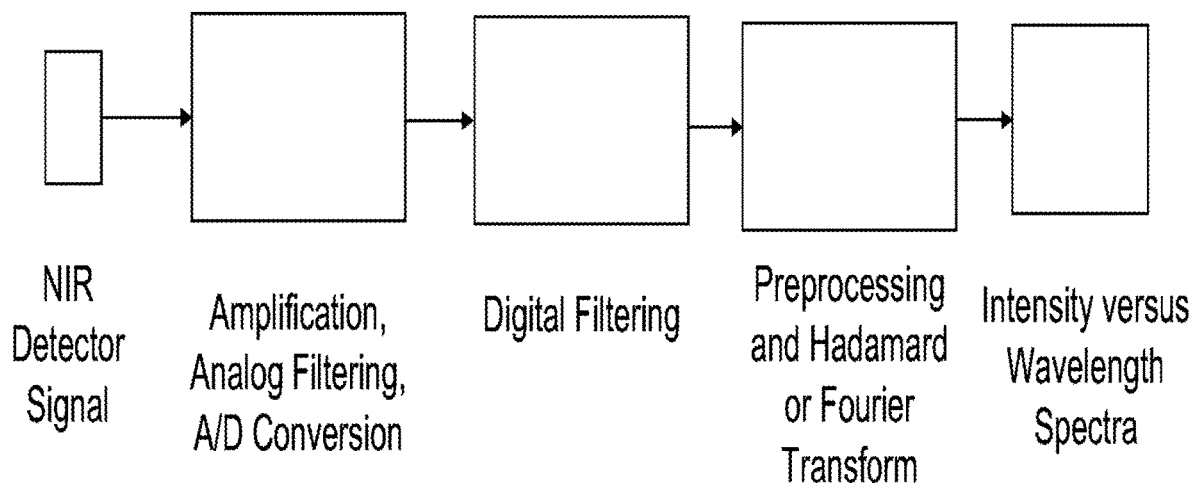
FIG. 18 is a schematic representation of the data acquisition subsystem.

The data acquisition subsystem 300 converts the optical signal from the sampling subsystem into a digital representation. FIG. 18 is a schematic representation of the data acquisition subsystem 300. An advantage of at least one embodiment of the present invention is that, similar to an interferometric spectrometer, only a single element detector is required to measure all desired wavelengths. Array detectors and their supporting electronics are a significant drawback due to their expensive nature.

The optical detector converts the incident light into an electrical signal as a function of time. Examples of detectors that are sensitive in the spectral range of 1.0 to 2.5 m include InGaAs, InAs, InSb, Ge, PbS, and PbSe. An example embodiment of the present invention can utilize a 1-mm, thermo-electrically cooled, extended range InGaAs detector that is sensitive to light in the 1.0 to 2.5 µm range. The 2.5 µm, extended range InGaAs detector has low Johnson noise and, as a result, allows Shot noise limited performance for the photon flux emanating from the tissue sampling subsystem. The extended InGaAs detector has peak sensitivity in the 2.0 to 2.5 µm spectral region where three very important alcohol absorption features are located. In comparison with the liquid nitrogen cooled InSb detector, the thermo-electrically cooled, extended range InGaAs can be more practical for a commercial product. Also, this detector exhibits over 120 dbc of linearity in the 1.0 to 2.5 µm spectral region. Alternative detectors can be suitable if the alcohol measurement system utilizes alternative wavelength regions. For example, a silicon detector can be suitable if the wavelength range of interest were within the 300-1100 nm range. Any photodetector can be used as long as the given photodetector satisfies basic sensitivity, noise and speed requirements.

The remainder of the data acquisition subsystem 300 amplifies and filters the electrical signal from the detector and then converts the resulting analog electrical signal to its digital representation with an analog to digital converter, digital filtering, and re-sampling of the digital signal from equal time spacing to equal position spacing. The analog electronics and ADC must support the high SNR and linearity inherent in the signal. To preserve the SNR and linearity of the signal, the data acquisition subsystem 300 can support at least 100 dbc of SNR plus distortion. The data acquisition subsystem 300 can produce a digitized representation of the signal. In some embodiments, a 24-bit delta-sigma ADC can be operated at 96 or 192 kHz. In a system that has only one channel of signal to digitize (instead of the two more common in delta-sigma ADC's), the signal can be passed into both inputs of the ADC and averaged following digitization. This operation can help to reduce any uncorrelated noise introduced by the ADC. If system performance requirements permit, alternate analog to digital converters can be used in which the sample acquisition is synchronized with the solid-state light source modulation rather than captured at equal time intervals. The digitized signal can be passed to a computing subsystem 400 for further processing, as discussed below.

The constant time sampling data acquisition subsystem 300 has several distinct advantages over other methods of digitizing signals. These advantages include greater dynamic range, lower noise, reduced spectral artifacts; detector noise limited operation and simpler and less expensive analog electronics. In addition, the constant time sampling technique allows digital compensation for frequency response distortions introduced by the analog electronics prior to the ADC. This includes non-linear phase error in amplification and filtering circuits as well as the non-ideal frequency response of the optical detector. The uniformly sampled digital signal allows for the application of one or more digital filters whose cumulative frequency response is the inverse of the analog electronics' transfer function (see, e.g., U.S. Pat. No. 7,446,878, incorporated herein by reference).

Computing Subsystem 400

The computing subsystem 400 performs multiple functions such converting the digitized data obtained from the data acquisition subsystem 300 to intensity versus wavelength spectra, performing spectral outlier checks on the spectra, spectral preprocessing in preparation for determination of the attribute of interest, determination of the attribute of interest, system status checks, display and processing requirements associated with the user interface, and data transfer and storage. In some embodiments, the computing subsystem is contained in a dedicated personal computer or laptop computer that is connected to the other subsystems of the invention. In other embodiments, the computing subsystem is a dedicated, embedded computer.

After converting the digitized data from the detector to intensity versus wavelength spectra, the computer system can check the spectra for outliers or bad scans. An outlier sample or bad scan is one that violates the hypothesized relationship between the measured signal and the properties of interest. Examples of outlier conditions include conditions where the calibrated instrument is operated outside of the specified operating ranges for ambient temperature, ambient humidity, vibration tolerance, component tolerance, power levels, etc. In addition, an outlier can occur if the composition or concentration of the sample is different than the composition or concentration range of the samples used to build the calibration model. The calibration model will be discussed later in this disclosure. Any outliers or bad scans can be deleted and the remaining good spectra can be averaged together to produce an average single beam spectrum for the measurement. The intensity spectra can be converted to absorbance by taking the negative base 10 logarithm (-log10) of the spectrum. The absorbance spectrum can be scaled to renormalize the noise.

A scaled absorbance spectrum can be used to determine the attribute of interest in conjunction with a calibration model that is obtained from the calibration subsystem 500. After determination of the attribute of interest, the computing subsystem 400 can report the result 830, e.g., to the subject, to an operator or administrator, to a recording system, or to a remote monitor. The computing subsystem 400 can also report the level of confidence in the goodness of the result. If the confidence level is low, the computing subsystem 400 can withhold the result and ask the subject to retest. If required, additional information can be conveyed that directs the user to perform a corrective action. See, e.g., US Application 20040204868, incorporated herein by reference. The results can be reported visually on a display, by audio and/or by printed means. Additionally, the results can be stored to form a historical record of the attribute. In other embodiments, the results can be stored and transferred to a remote monitoring or storage facility via the internet, phone line, or cell phone service.

The computing subsystem 400 includes a central processing unit (CPU), memory, storage, a display and preferably a communication link. An example of a CPU is the Intel Pentium microprocessor. The memory can be static random access memory (RAM) and/or dynamic random access memory. The storage can be accomplished with non-volatile RAM or a disk drive. A liquid crystal, LED, or other display can be suitable. The communication link can be, as examples, a high speed serial link, an Ethernet link, or a wireless communication link. The computer subsystem can, for example, produce attribute measurements from the received and processed interferograms, perform calibration maintenance, perform calibration transfer, run instrument diagnostics, store a history of measured alcohol concentrations and other pertinent information, and in some embodiments, communicate with remote hosts to send and receive data and new software updates.

The computing system 400 can also contain a communication link that allows transfer of a subject's alcohol measurement records and the corresponding spectra to an external database. In addition, the communication link can be used to download new software to the computer and update the multivariate calibration model. The computer system can be viewed as an information appliance. Examples of information appliances include personal digital assistants, web-enabled cellular phones and handheld computers.

Calibration Subsystem 500

A calibration model is used in connection with the spectral information in order to obtain alcohol measurements. In some embodiments, the calibration model is formed by acquiring blood reference measurements and contemporaneous spectroscopic data on multiple subjects in a wide variety of environmental conditions. In these embodiments, spectroscopic data can be acquired from each subject over a range of blood alcohol concentrations. In other embodiments, a hybrid calibration model can be to measure the alcohol concentrations of subject spectra. In this case, the term hybrid model denotes that a partial least squares (PLS) calibration model was developed using a combination of in vitro and in vivo spectral data. The in vitro portion of the data was a 0.1 mm pathlength transmission spectrum of 500 mg/dL alcohol in water measured using the non-invasive measurement system configured for transmission measurements. The transmission spectrum was ratioed to a 0.1 mm pathlength transmission spectrum of water, converted to absorbance, and normalized to unit pathlength and concentration.

Light propagation through tissue is a complex function of the diffuse reflectance optical tissue sampler design, physiological variables, and wavenumber. Consequently, the pathlength of light through tissue has a wavenumber dependence that is not encountered in scatter-free transmission measurements. In order to account for the wavenumber dependence, the interaction of the optical tissue sampler with the scattering properties of human tissue was modeled via Monte-Carlo simulation using a commercial optical ray-tracing software package (TracePro). Using the resulting model of the photon-tissue interactions, an estimate of the effective pathlength of light through the dermis and subcutaneous tissue layers as a function of wavenumber was generated. The effective pathlength ($l_{eff}$) is defined as $$l_{eff}(v) = \frac{\sum_{i=1}^{N} l_i \exp(-\mu_a(v) l_i)}{\sum_{i=1}^{N} l_i},$$

where v is wavenumber, $l_i$ is the pathlength traversed by the $i^{th}$ ray in the Monte Carlo simulation [mm], N is the total number of rays in the simulation, and a is the (wavenumber-dependent) absorption coefficient [$mm^{-1}$]. Due to its large absorption in vivo, water is the only analyte that has a significant effect on the effective pathlength. Therefore, for the purposes of the effective pathlength calculation, the absorption coefficients used were those of water at physiological concentrations. The alcohol absorbance spectrum (as measured in transmission) was then scaled by the computed path function to form a corrected alcohol spectrum representative of the wavenumber dependent pathlength measured by the diffuse reflectance optical sampler. This corrected spectrum formed the base spectrum for the mathematical addition of alcohol to the calibration spectra.

Figure 19:
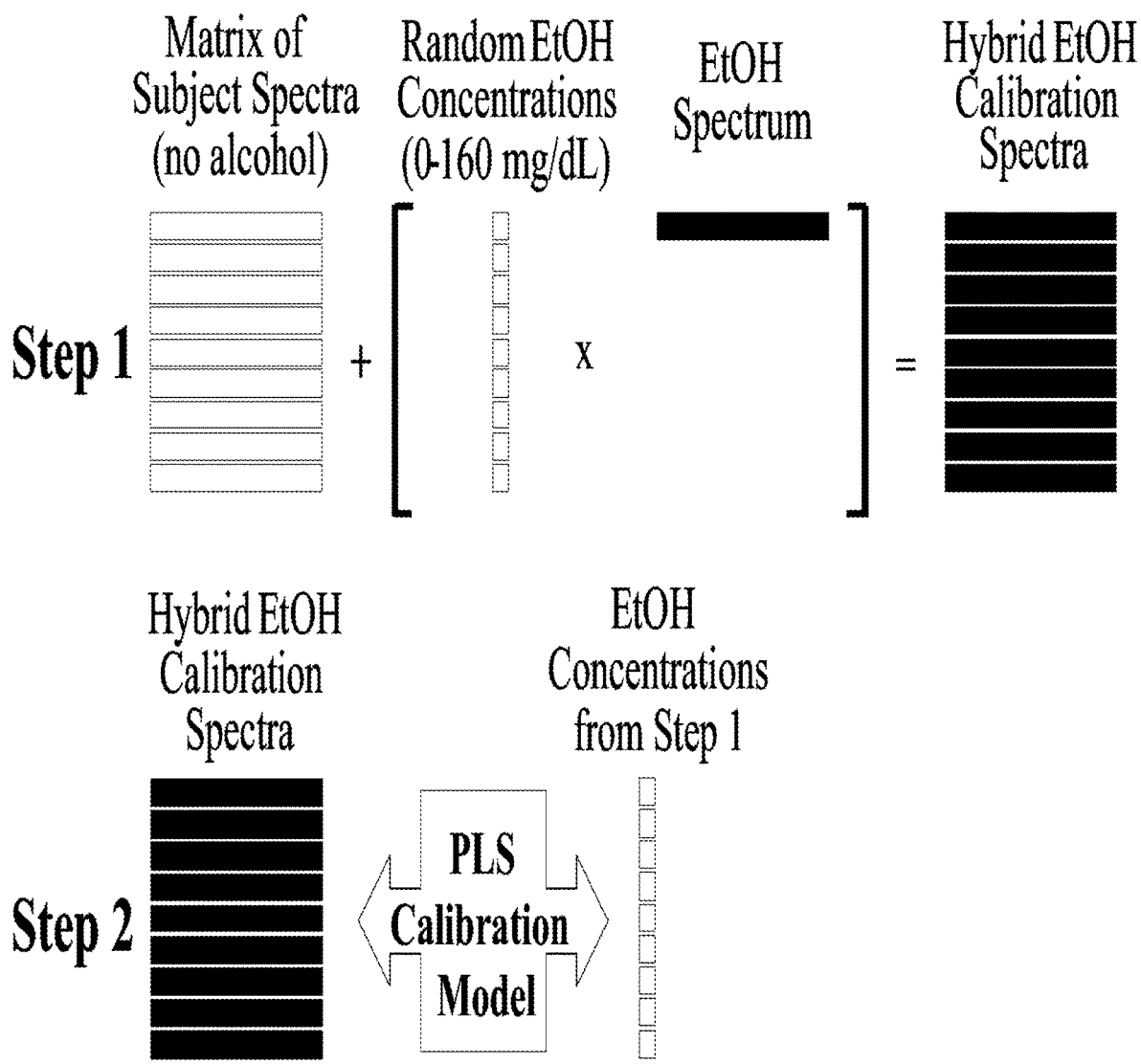
FIG. 19 is a diagram of the hybrid calibration formation process.

The in vivo data comprised noninvasive tissue spectra collected from persons who had not consumed alcohol. A hybrid model was formed by adding the alcohol pure component spectrum, weighted by various alcohol "concentrations" (ranging from 0 to 160 mg/dL), to the noninvasive tissue spectral data. The PLS calibration model was built by regressing the synthetic alcohol concentrations on the hybrid spectral data. FIG. 19 is a schematic representation of a hybrid calibration formation process. The hybrid calibration in this work used approximately 1500 non-invasive tissue spectra that were collected from 133 subjects over three months.

The use of hybrid calibration models, rather than calibration models built from spectra acquired from subjects who have consumed alcohol, can provide significant advantages. The hybrid modeling process makes it possible to generate calibration spectra that contain higher concentrations (up to 160 mg/dL in this work) of alcohol than would be considered safe for consumption in a human subject study (120 mg/dL is considered a safe upper limit). This can result in a stronger calibration with a wider range of analyte concentrations that is able to predict higher alcohol concentrations more accurately. This can be important because alcohol concentrations observed in the field can be more than double the maximum safe dosage in a clinical research setting. The hybrid calibration process also allows the prevention of correlations between alcohol and the spectral interferents in tissue. For example, the random addition of alcohol signal to the calibration spectra prevents alcohol concentration from being correlated with water concentration. Thus, the hybrid approach prevents the possibility that the measurement could spuriously track changes in tissue water content instead of alcohol concentration.

Once formed, it is desirable that a calibration remains stable and produces accurate attribute predictions over an extended period of time. This process is referred to as calibration maintenance and can be comprised of multiple methods that can be used individually or in conjunction. The first method is to create the calibration in a manner that inherently makes it robust. Several different types of instrumental and environmental variation can affect the prediction capability of a calibration model. It is possible and desirable to reduce the magnitude of the effect of instrumental and environmental variation by incorporating this variation into the calibration model.

It is difficult, however, to span the entire possible range of instrument states during the calibration period. System perturbations can result in the instrument being operated outside the space of the calibration model. Measurements made while the instrument is in an inadequately modeled state can exhibit prediction errors. In the case of in vivo optical measurements of medically significant attributes, these types of errors can result in erroneous measurements that degrade the utility of the system. Therefore it is often advantageous to use additional calibration maintenance techniques during the life of the instrument in order to continually verify and correct for the instrument's status.

Examples of problematic instrument and environmental variation include, but are not limited to: changes in the levels of environmental interferents such as water vapor or $CO_2$ gas, changes in the alignment of the instrument's optical components, fluctuations in the output power of the instrument's illumination system, and changes in the spatial and angular distribution of the light output by the instrument's illumination system.

Calibration maintenance techniques are discussed in U.S. Pat. No. 6,983,176, "Optically Similar Reference Samples and Related Methods for Multivariate Calibration Models Used in Optical Spectroscopy"; U.S. Pat. No. 7,092,832, "Adaptive Compensation for Measurement Distortions in Spectroscopy"; U.S. Pat. No. 7,098,037, "Accommodating Subject and Instrument Variations in Spectroscopic Determinations", and U.S. Pat. No. 7,202,091, "Optically Similar Reference Samples", each of which is incorporated herein by reference. In some of the disclosed methods, an environmentally inert non-tissue sample, such as an integrating sphere, that may or may not contain the attribute of interest is used in order to monitor the instrument over time. The sample can be incorporated into the optical path of the instrument or interface with the sampling subsystem in a manner similar to that of tissue measurements. The sample can be used in transmission or in reflectance and can contain stable spectral features or contribute no spectral features of its own. The material can be a solid, liquid, or gel material as long as its spectrum is stable or predicable over time. Any unexplained change in the spectra acquired from the sample over time indicate that the instrument has undergone a perturbation or drift due to environmental effects. The spectral change can then be used to correct subsequent tissue measurements in humans in order to ensure and accurate attribute measurement.

Another means for achieving successful calibration maintenance is to update the calibration using measurements acquired on the instrument over time. Usually, knowledge of the reference value of the analyte property of interest is required in order to perform such an update. However, in some applications, it is known that the reference value is usually, but not always, a specific value. In this case, this knowledge can be used to update the calibration even though the specific value of the analyte property is not known for each measurement. For example, in alcohol screening in residential treatment centers, the vast majority of measurements are performed on individuals that have complied with their alcohol consumption restrictions and therefore have an alcohol concentration of zero. In this case, the alcohol concentration measurement or the associated spectrum obtained from the device disclosed according to the various embodiments of the present invention can be used in conjunction with a presumed zero as a reference value. Thus, the calibration can be updated to include new information as it is acquired in the field. This approach can also be used to perform calibration transfer as measurements with presumed zeros can be used at the time of system manufacture or installation in order to remove any system-specific bias in the analyte property measurements of interest. The calibration maintenance update or calibration transfer implementation can be accomplished by a variety of means such as, but not limited to, orthogonal signal correction (OSV), orthogonal modeling techniques, neural networks, inverse regression methods (PLS, PCR, MLR), direct regression methods (CLS), classification schemes, simple median or moving windows, principal components analysis, or combinations thereof.

Once a calibration is formed, it is often desirable to transfer the calibration to all existing and future units. This process is commonly referred to as calibration transfer. While not required, calibration transfer prevents the need for a calibration to be determined on each system that is manufactured. This represents a significant time and cost savings that can affect the difference between success or failure of a commercial product. Calibration transfer arises from the fact that optical and electronic components vary from unit to unit which, in aggregate, can result in a significant difference in spectra obtained from multiple instruments. For example, two solid-state light sources can have different color temperatures thereby resulting in a different light distribution for the two sources. The responsivity of two detectors can also differ significantly, which can result in additional spectral differences.

Similar to calibration maintenance, multiple methods can be used in order to effectively achieve calibration transfer. The first method is to build the calibration with multiple instruments. The presence of multiple instruments allows the spectral variation associated with instrument differences to be determined and made orthogonal to the attribute signal during the calibration formation process. While this approach reduces the net attribute signal, it can be an effective means of calibration transfer.

Additional calibration transfer methods involve explicitly determining the difference in the spectral signature of a system relative to those used to build the calibration. In this case, the spectral difference can then be used to correct a spectral measurement prior to attribute prediction on a system or it can be used to correct the predicted attribute value directly. The spectral signature specific to an instrument can be determined from the relative difference in spectra of a stable sample acquired from the system of interest and those used to build the calibration. The samples described in the calibration maintenance section are also applicable to calibration transfer. See, e.g. U.S. Pat. No. 6,441,388, "Method and Apparatus for Spectroscopic Calibration Transfer", incorporated herein by reference.

Alcohol Measurement Modalities

Depending on the application of interest, the measurement of an analyte property can be considered in terms of two modalities. The first modality is "walk up" or "universal" and represents an analyte property determination wherein prior measurements of the sample (e.g. subject) are not used in determining the analyte property from the current measurement of interest. In the case of measuring in vivo alcohol, driving under the influence enforcement would fall into this modality as in most cases the person being tested will not have been previously measured on the alcohol measurement device. Thus, no prior knowledge of that person is available for use in the current determination of the analyte property.

The second modality is termed "enrolled" or "tailored" and represents situations where prior measurements from the sample or subject are available for use in determining the analyte property of the current measurement. An example of an environment where this modality can be applied is vehicle interlocks where a limited number of people are permitted to drive or operate a vehicle or machine. Additional information regarding embodiments of enrolled and tailored applications can be found in U.S. Pat. Nos. 6,157, 041 and 6,528,809, titled "Method and Apparatus for Tailoring Spectroscopic Calibration Models", each of which is incorporated herein by reference. In enrolled applications, the combination of the analyte property measurement with a biometric measurement can be particularly advantageous as the same spectroscopic measurement can assess if a prospective operator is authorized to use the equipment or vehicle via the biometric while the analyte property can access their fitness level (e.g. sobriety).

Methods for Determining Biometric Verification or Identification from Spectroscopic Signals Biometric identification describes the process of using one or more physical or behavioral features to identify a person or other biological entity. There are two common biometric modes: identification and verification. Biometric identification attempts to answer the question of, "do I know you?" The biometric measurement device collects a set of biometric data from a target individual. From this information alone it assesses whether the person was previously enrolled in the biometric system. Systems that perform the biometric identification task, such as the FBI's Automatic Fingerprint Identification System (AFIS), are generally very expensive (several million dollars or more) and require many minutes to detect a match between an unknown sample and a large database containing hundreds of thousands or millions of entries. In biometric verification the relevant question is, "are you who you say you are?" This mode is used in cases where an individual makes a claim of identity using a code, magnetic card, or other means, and the device uses the biometric data to confirm the identity of the person by comparing the target biometric data with the enrolled data that corresponds with the purported identity. The present apparatus and methods for monitoring the presence or concentration of alcohol or substances of abuse in controlled environments can use either biometric mode.

There also exists at least one variant between these two modes that is also suitable for use in various embodiments of the present invention. This variant occurs in the case where a small number of individuals are contained in the enrolled database and the biometric application requires the determination of only whether a target individual is among the enrolled set. In this case, the exact identity of the individual is not required and thus the task is somewhat different (and often easier) than the identification task described above. This variant might be useful in applications where the biometric system is used in methods where the tested individual must be both part of the authorized group and sober but their specific identity is not required. The term "identity characteristic" includes all of the above modes, variants, and combinations or variations thereof.

There are three major data elements associated with a biometric measurement: calibration, enrollment, and target spectral data. The calibration data are used to establish spectral features that are important for biometric determinations. This set of data consists of series of spectroscopic tissue measurements that are collected from an individual or individuals of known identity. Preferably, these data are collected over a period of time and a set of conditions such that multiple spectra are collected on each individual while they span nearly the full range of physiological states that a person is expected to go through. In addition, the instrument or instruments used for spectral collection generally should also span the full range of instrumental and environmental effects that it or sister instruments are likely to see in actual use. These calibration data are then analyzed in such a way as to establish spectral wavelengths or "factors" (i.e. linear combinations of wavelengths or spectral shapes) that are sensitive to between-person spectral differences while minimizing sensitivity to within-person, instrumental (both within- and between-instruments), and environmental effects. These wavelengths or factors are then used subsequently to perform the biometric determination tasks.

The second major set of spectral data used for biometric determinations is the enrollment spectral data. The purpose of the enrollment spectra for a given subject or individual is to generate a "representation" of that subject's unique spectroscopic characteristics. Enrollment spectra are collected from individuals who are authorized or otherwise required to be recognized by the biometric system. Each enrollment spectrum can be collected over a period of seconds or minutes. Two or more enrollment measurements can be collected from the individual to ensure similarity between the measurements and rule out one or more measurements if artifacts are detected. If one or more measurements are discarded, additional enrollment spectra can be collected. The enrollment measurements for a given subject can be averaged together, otherwise combined, or stored separately. In any case, the data are stored in an enrollment database. In some cases, each set of enrollment data are linked with an identifier (e.g. a password or key code) for the persons on whom the spectra were measured. In the case of an identification task, the identifier can be used for record keeping purposes of who accessed the biometric system at which times. For a verification task, the identifier is used to extract the proper set of enrollment data against which verification is performed.

The third and final major set of data used for the biometric system is the spectral data collected when a person attempts to use the biometric system for identification or verification. These data are referred to as target spectra. They are compared to the measurements stored in the enrollment database (or subset of the database in the case of identity verification) using the classification wavelengths or factors obtained from the calibration set. In the case of biometric identification, the system compares the target spectrum to all of the enrollment spectra and reports a match if one or more of the enrolled individual's data is sufficiently similar to the target spectrum. If more than one enrolled individual matches the target, then either all of the matching individuals can be reported, or the best match can be reported as the identified person. In the case of biometric verification, the target spectrum is accompanied by an asserted identity that is collected using a magnetic card, a typed user name or identifier, a transponder, a signal from another biometric system, or other means. The asserted identity is then used to retrieve the corresponding set of spectral data from the enrollment database, against which the biometric similarity determination is made and the identity verified or denied. If the similarity is inadequate, then the biometric determination is cancelled and a new target measurement may be attempted.

In one method of verification, principle component analysis is applied to the calibration data to generate spectral factors. These factors are then applied to the spectral difference taken between a target spectrum and an enrollment spectrum to generate Mahalanobis distance and spectral residual magnitude values as similarity metrics. Identify is verified only if the aforementioned distance and magnitude are less than a predetermined threshold set for each. Similarly, in an example method for biometric identification, the Mahalanobis distance and spectral residual magnitude are calculated for the target spectrum relative each of the database spectra. The identity of the person providing the test spectrum is established as the person or persons associated with the database measurement that gave the smallest Mahalanobis distance and spectral residual magnitude that is less than a predetermined threshold set for each.

In an example method, the identification or verification task is implemented when a person seeks to perform an operation for which there are a limited number of people authorized (e.g., perform a spectroscopic measurement, enter a controlled facility, pass through an immigration checkpoint, etc.). The person's spectral data is used for identification or verification of the person's identity. In this method, the person initially enrolls in the system by collecting one or more representative tissue spectra. If two or more spectra are collected during the enrollment, then these spectra can be checked for consistency and recorded only if they are sufficiently similar, limiting the possibility of a sample artifact corrupting the enrollment data. For a verification implementation, an identifier such as a PIN code, magnetic card number, username, badge, voice pattern, other biometric, or some other identifier can also be collected and associated with the confirmed enrollment spectrum or spectra.

In subsequent use, biometric identification can take place by collecting a spectrum from a person attempting to gain authorization. This spectrum can then be compared to the spectra in the enrolled authorization database and an identification made if the match to an authorized database entry was better than a predetermined threshold. The verification task is similar, but can require that the person present the identifier in addition to a collected spectrum. The identifier can then be used to select a particular enrollment database spectrum and authorization can be granted if the current spectrum is sufficiently similar to the selected enrollment spectrum. If the biometric task is associated with an operation for which only a single person is authorized, then the verification task and identification task are the same and both simplify to an assurance that the sole authorized individual is attempting the operation without the need for a separate identifier.

The biometric measurement, regardless of mode, can be performed in a variety of ways including linear discriminant analysis, quadratic discriminant analysis, K-nearest neighbors, neural networks, and other multivariate analysis techniques or classification techniques. Some of these methods rely upon establishing the underlying spectral shapes (factors, loading vectors, eigenvectors, latent variables, etc.) in the intra-person calibration database, and then using standard outlier methodologies (spectral F ratios, Mahalanobis distances, Euclidean distances, etc.) to determine the consistency of an incoming measurement with the enrollment database. The underlying spectral shapes can be generated by multiple means as disclosed herein.

First, the underlying spectral shapes can be generated based upon simple spectral decompositions (eigen analysis, Fourier analysis, etc.) of the calibration data. The second method of generating underlying spectral shapes relates to the development of a generic model as described in U.S. Pat. No. 6,157,041, entitled "Methods and Apparatus for Tailoring Spectroscopic Calibration Models," which is incorporated by reference. In this application, the underlying spectral shapes are generated through a calibration procedure performed on intra-person spectral features. The underlying spectral shapes can be generated by the development of a calibration based upon simulated constituent variation. The simulated constituent variation can model the variation introduced by real physiological or environmental or instrumental variation or can be simply be an artificial spectroscopic variation. It is recognized that other means of determining underlying shapes would be applicable to the identification and verification methods of the disclosed embodiments of the present invention. These methods can be used either in conjunction with, or in lieu of the aforementioned techniques.

Calibration Check Samples

In addition to disposables to ensure subject safety, disposable calibration check samples can be used to verify that the instrument is in proper working condition. In many commercial applications of alcohol measurements, the status of the instrument must be verified to ensure that subsequent measurements will provide accurate alcohol concentrations or attribute estimates. The instrument status is often checked immediately prior to a subject measurement. In some embodiments, the calibration check sample can include alcohol. In other embodiments, the check sample can be an environmentally stable and spectrally inert sample, such as an integrating sphere. The check sample can be a gas or liquid that is injected or flowed through a spectroscopic sampling chamber. The check sample can also be a solid, such as a gel, that may contain alcohol. The check sample can be constructed to interface with the sampling subsystem or it can be incorporated into another area of the optical path of the system. These examples are meant to be illustrative and are not limiting to the various possible calibration check samples.

Direction of Change (DOC) and Rate of Change (ROC)

Methods for measurement of the direction and magnitude of concentration changes of tissue constituents, such as alcohol, using spectroscopy are considered to be within the scope of the present invention. The non-invasive measurement obtained from the current invention is inherently semi-time resolved. This allows attributes, such as alcohol concentration, to be determined as a function of time. The time resolved alcohol concentrations can then be used to determine the rate and direction of change of the alcohol concentration. In addition, the direction of change information can be used to partially compensate for any difference in blood and non-invasive alcohol concentration that is caused by physiological kinetics. See U.S. Pat. No. 7,016,713, "Determination of Direction and Rate of Change of an Analyte", and US Application 20060167349, "Apparatus for Noninvasive Determination of Rate of Change of an Analyte", each of which is incorporated herein by reference. A variety of techniques for enhancing the rate and direction signal have been uncovered. Some of these techniques include heating elements, rubrifractants, and index-matching media. The present invention is not limited to a particular form of enhancement or equilibration. These enhancements are not a required in the present invention, but are included for illustrative purposes only.

Subject Safety

Another aspect of non-invasive alcohol measurements is the safety of the subjects during the measurements. In order to prevent measurement contamination or transfer of pathogens between subjects it is desirable, but not necessary, to use disposable cleaning agents and/or protective surfaces in order to protect each subject and prevent fluid or pathogen transfer between subjects. For example, in some embodiments an isopropyl wipe can be used to clean each subject's sampling site and/or the sampling subsystem surface prior to measurement. In other embodiments, a disposable thin film of material such as ACLAR could be placed between the sampling subsystem and the subject prior to each measurement in order to prevent physical contact between the subject and the instrument. In other embodiments, both cleaning and a film could be used simultaneously. As mentioned in the sampling subsystem portion of this disclosure, the film can also be attached to a positioning device and then applied to the subject's sampling site. In this embodiment, the positioning device can interface with the sampling subsystem and prevent the subject from moving during the measurement while the film serves its protective role.

Topical Interferents

In subject measurements the presence of topical interferents on the sampling site is a significant concern. Many topical interferents have spectral signatures in the near infrared region and can therefore contribute significant measurement error when present. Certain embodiments of the present invention deal with the potential for topical interferents in three ways that can be used individually or in conjunction. First, a disposable cleaning agent similar to that described in the subject safety section can be used. The use of the cleaning agent can either be at the discretion of the system operator or a mandatory step in the measurement process. Multiple cleaning agents can also be used that individually target different types of topical interferents. For example, one cleaning agent can be used to remove grease and oils, while another could be used to remove consumer goods such as cologne or perfume. The purpose of the cleaning agents is to remove topical interferents prior to the attribute measurement in order to prevent them from influencing the accuracy of the system.

Figure 20:
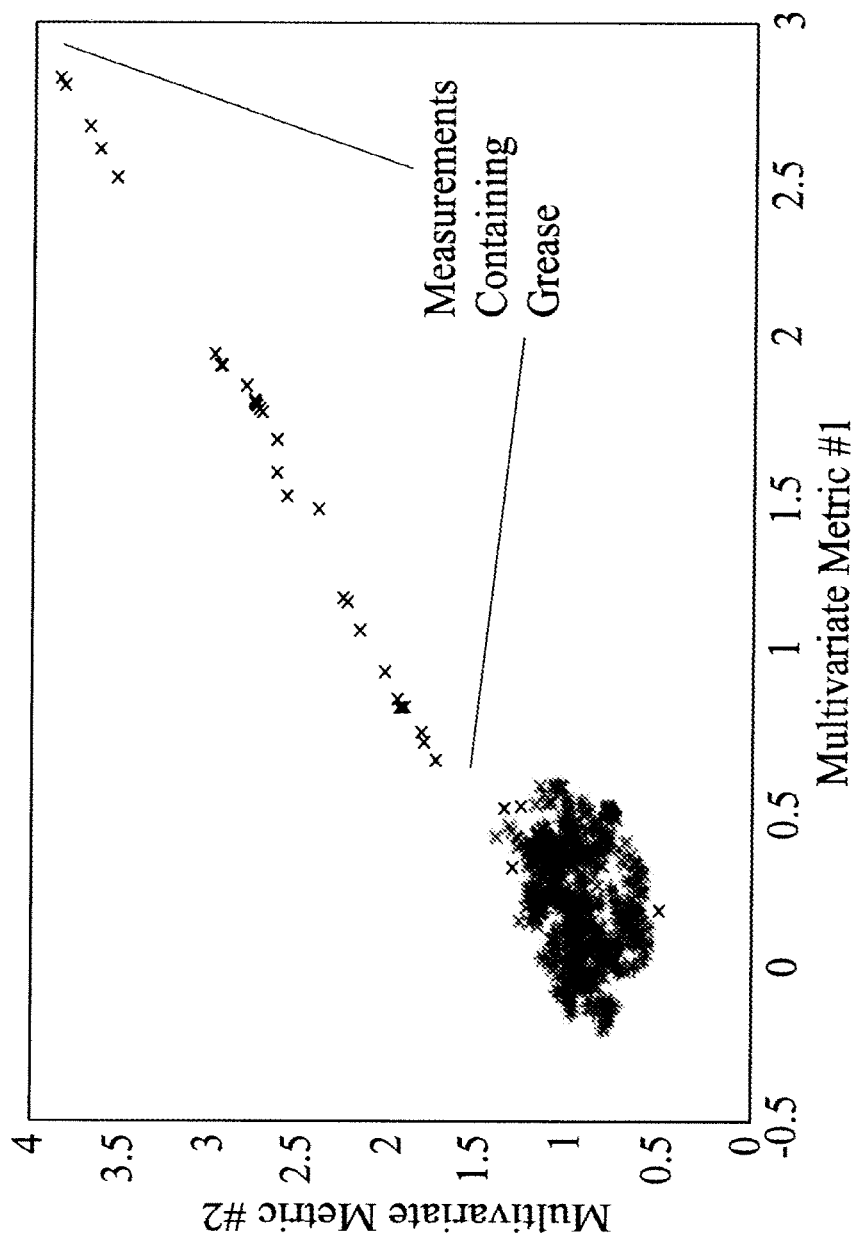
FIG. 20 demonstrates the effectiveness of multivariate calibration outlier metrics for detecting the presence of topical interferents.

The second method for mitigating the presence of topical interferents is to determine if one or more interferents are present on the sampling site. The multivariate calibration models used in the calibration subsystem offer inherent outlier metrics that yield important information regarding the presence of un-modeled interferents (topical or otherwise). As a result, they provide insight into the trustworthiness of the attribute measurement. FIG. 20 shows example outlier metric values from noninvasive measurements acquired during the clinical studies. All of the large metric values (clearly separated from the majority of the points) correspond to measurements where grease had been intentionally applied to the subject's sampling site. These metrics do not specifically identify the cause of the outlier, but they do indicate that the associated attribute measurement is suspect. An inflated outlier metric value (a value beyond a fixed threshold, for example) can be used to trigger a fixed response such as a repeat of the measurement, application of an alternative calibration model, or a sampling site cleaning procedure. This is represented in FIG. 20 as the "Spectral Check OK" decision point.

The final topical interferent mitigation method involves adapting the calibration model to include the spectral signature of the topical interferent. The adapted calibration model can either be created on demand or selected from an existing library of calibration models. Each calibration in the library would be targeted at mitigating a different interferent or class of interferents such as oils. In some embodiments, the appropriate calibration model can be chosen based on the portion of an acquired spectrum that is unexplained by the original calibration model. This portion of the spectrum is referred to as the calibration model residual. Because each topical interferent or class of interferents has a unique near infrared spectrum, the calibration model residual can be used to identify the topical interferent.

The model residual or the pure spectrum (obtained from a stored library) of the interferents can then be incorporated into the spectra used to form the calibration. The multivariate calibration is then reformed with the new spectra such that the portion of the attribute signal that is orthogonal to the interferent can be determined. The new calibration model is then used to measure the attribute of interest and thereby reduce the effects of the topical interferent on attribute measurement accuracy. The resulting model will reduce the effect of the interferent on the alcohol measurement at the expense of measurement precision when no interferents are present. This process is referred to as calibration immunization. The immunization process is similar to the hybrid calibration formation process shown in FIG. 19, but includes the additional step of the mathematical addition of the interferent's spectral variation. It should be noted that, due to the impact of the immunization process on measurement precision, it can be desirable to identify possible interferents for each measurement and immunize specifically against them rather than attempt to develop a calibration that is immunized against all possible interferents. Additional details can be found in US 20070142720, "Apparatus and methods for mitigating the effects of foreign interferents on analyte measurements in spectroscopy", incorporated herein by reference.

Advantages of Semiconductor Light Source Alternatives

Figure 21:
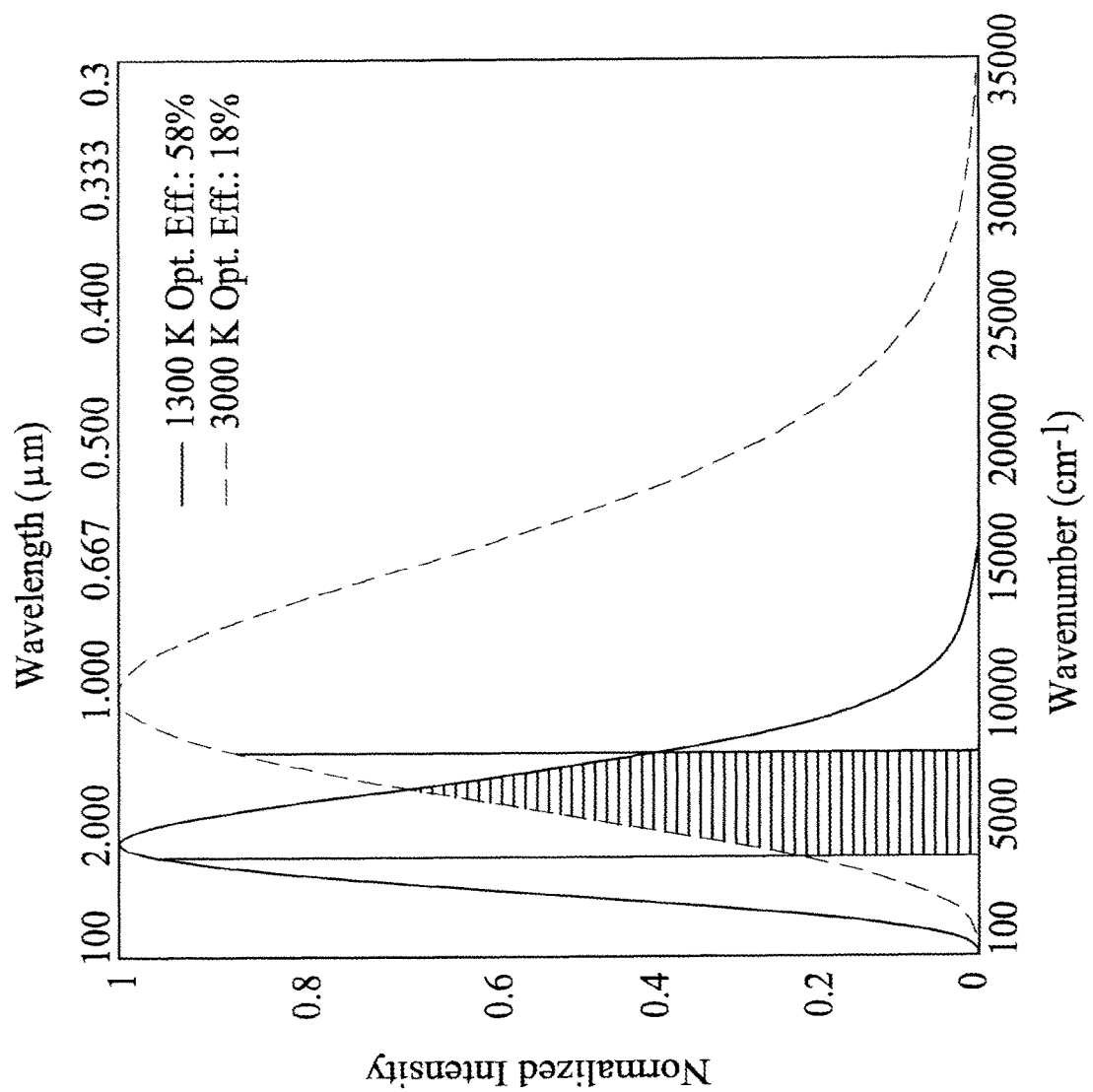
FIG. 21 shows normalized NIR spectra of 1300 and 3000 K blackbody radiators over the 100-33000 $cm^{-1}$ (100-0.3 μm) range.

Most light sources used in NIR and IR spectroscopy are blackbody radiators. The light emitted by a blackbody radiator is governed by Plank's law which indicates that the intensity of the light emitted is a function of wavelength and the temperature of the blackbody. FIG. 21 shows normalized NIR spectra of 1300 and 3000 K blackbody radiators over the 100-33000 $cm^{-1}$ (100-0.3 µm) range with the 4000-8000 $cm^{-1}$ (2.5-1.25 µm) range used by the alcohol measurement device shaded. 1300 K is a reasonable temperature for the ceramic-based blackbody light source and 3000 K is a reasonable temperature for Quartz Tungsten Halogen (QTH) lamps which are often employed in spectroscopic applications. FIG. 21 indicates that the optical efficiency of both blackbody light sources is not ideal in that a significant amount of light is emitted at wavelengths outside the region of interest for measuring alcohol with the optical efficiency of the ceramic light source being 58% and the QTH only 18%.

In addition to optical efficiency, blackbody light sources can have poor electrical efficiency. Practical blackbody light sources require a significant amount of electrical power, not all of which is converted to emitted light. Electrical and optical power measurements on hundreds of ceramic blackbody light sources that show an average of 1.1 W of optical power at an average of 24 W of electrical power (4.4% electrical efficiency). When combined with the optical efficiency of 58%, the overall efficiency of the ceramic blackbody is approximately 2.5%. In other words, at 24 W of electrical power, approximately 0.6 W of optical power is emitted in the 4000 to 8000 $cm^{-1}$ region of interest. Further losses are incurred as not all light emitted by the source is collected by the remainder of the optical system.

As indicated by the low electrical efficiency, most of the applied electrical power is converted to heat which has a detrimental beyond the higher than desired power requirement. The heat generated by the blackbody light source can have an impact on the thermal state and stability of the spectroscopic measurement device. Consequently, in some situations the device must be powered on and allowed to reach thermal equilibrium prior to performing measurements. The equilibration time associated with the blackbody light source can range from minutes to hours which can be disadvantageous in some situations.

Blackbody light sources exhibit an aging effect as the material resistance changes. From an optical perspective, there are to significant implications associated with the light source aging. First, as the resistance increases the amount of optical power emitted decreases. In one experiment, the measured intensity over time observed for a demonstrative ceramic blackbody light source exhibited a 50% reduction in power over 3500 hours. The intensity degradation over time tends to be exponential in nature and can necessitate replacement of the light source at regular intervals which can be disadvantageous in some deployment environments. Second, the temperature of the light source changes which alters the distribution of the light as a function of wavelength. Depending on the severity of the color temperature change, the stability of the spectroscopic device over time can be impacted. Solid-state light sources do not critically fail in any manner similar to filament lamps and have typical lifetimes ranging from 50,000 to 100,000 hours. As a result, solid-state light sources offer the potential for a 10× improvement in light source life and a corresponding reduction in the need for routine maintenance relative to blackbody light sources.

Semiconductor light sources such as diode lasers can have small emissive areas when compared to their blackbody counterparts that are driven by the size of the semiconductor die itself. The photon emission cannot occur outside of the area of the die as it is generated within the semiconductor structure. The small size (a common emissive area is a 0.3 mm×0.3 mm square or 0.09 $mm^2$) can be advantageous in that any heterogeneity within that area will be insignificant relative to size of the output of the illumination system (which can be several $mm^2$ or larger depending on the application). Thus, as long as the die (or dies if multiple semiconductors are employed) do not physically move, the spatial output will be very stable. The objective of subsequent spatial homogenizers is then to uniformly distribute the light emitted by the die across the entire area of the illumination system output.

Another advantage of semiconductor light sources such as diode lasers, VCSEL's, and LED's is the ability to incorporate more than one dye into the same physical package. For example, additional solid-state light sources of the same type can be included in order to increase the optical power at the corresponding wavelengths. Such approaches allow an unprecedented level of control over both the specific wavelengths and relative intensities emitted by an illumination system. This could be used to accentuate wavelengths important to a given analyte of interest such as alcohol, while reducing the output at less-important wavelengths. Whether the set of solid-state light sources is all of the same type or a mixture, up to several hundred could be incorporated into the same package while retaining an integrated optical area consistent with use in noninvasive analyte measurements such as alcohol.

Another advantage of semiconductor light sources is the ability to select which light sources are on at a given time as well as tune their output via voltage or current and temperature. Consequently, a single illumination system could be optimized for measurements of multiple analytes. For example, when measuring alcohol in tissue a given set of solid-state light sources could be activated. Likewise, a different set could be activated when measuring a different analyte such as cholesterol or glucose.

Methods for Spatial and Angular Homogenization

Light homogenizers such as optical diffusers, light pipes, and other scramblers can be incorporated into some embodiments of the illumination/modulation subsystem 100 in order to provide reproducible and, preferably, uniform radiance at the input of the tissue sampling subsystem 200. Uniform radiance can ensure good photometric accuracy and even illumination of the tissue. Uniform radiance can also reduce errors associated with manufacturing differences between solid-state light sources. Uniform radiance can be utilized for achieving accurate and precise measurements. See, e.g., U.S. Pat. No. 6,684,099, which is incorporated herein by reference.

A ground glass plate is an example of an optical diffuser. The ground surface of the plate effectively scrambles the angle of the radiation emanating from the solid-state light source and its transfer optics. A light pipe can be used to homogenize the intensity of the radiation such that it is spatially uniform at the output of the light pipe. In addition, light pipes with a double bend will scramble the angles of the radiation. For creation of uniform spatial intensity and angular distribution, the cross section of the light pipe should not be circular. Square, hexagonal and octagonal cross sections are effective scrambling geometries. The output of the light pipe can directly couple to the input of the tissue sampler or can be used in conjunction with additional transfer optics before the light is sent to the tissue sampler. See, e.g., U.S. patent application Ser. No. 09/832,586, "Illumination Device and Method for Spectroscopic Analysis," which is incorporated herein by reference.

In an exemplary embodiment, the radiation homogenizer is a light pipe. A light pipe is generally fabricated from a metallic, glass (amorphous), crystalline, polymeric, or other similar material, or any combination thereof. Physically, the light pipe comprises a proximal end, a distal end, and a length there between. The length of a light pipe, for this application, is measured by drawing a straight line from the proximal end to the distal end of the light pipe. Thus, the same segment of light pipe 91 may have varying lengths depending upon the shape the segment forms. The length of the segment readily varies with the light pipe's intended application.

In an exemplary embodiment, the segment forms an S-shaped light pipe. The S-shaped bend in the light pipe provides angular homogenization of the light as it passes through the light pipe. It is, however, recognized that angular homogenization can be achieved in other ways. A plurality of bends or a non-S-shaped bend could be used. Further, a straight light pipe could be used provided the interior surface of the light pipe included a diffusely reflective coating over at least a portion of the length. The coating provides angular homogenization as the light travels through the pipe. Alternatively, the interior surface of the light pipe can be modified to include dimples or "microstructures" such as micro-optical diffusers or lenses to accomplish angular homogenization. Finally, a ground glass diffuser could be used to provide some angular homogenization.

The cross-section of the light pipe may also form various shapes. In particular, the cross-section of the light pipe is preferably polygonal in shape to provide spatial homogenization. Polygonal cross-sections include all polygonal forms having three to many sides. Certain polygonal cross-sections are proven to improve spatial homogenization of channeled radiation. For example, a light pipe possessing a hexagonal cross-section the entire length thereof provided improved spatial homogenization when compared to a light pipe with a cylindrical cross-section of the same length.

Additionally, cross-sections throughout the length of the light pipe may vary. As such, the shape and diameter of any cross-section at one point along the length of the light pipe may vary with a second cross-section taken at a second point along the same segment of pipe. In certain embodiments, the light pipe is of a hollow construction between the two ends. In these embodiments, at least one lumen or conduit may run the length of the light pipe. The lumens of hollow light pipes generally possess a reflective characteristic. This reflective characteristic aids in channeling radiation through the length of the light pipe so that the radiation may be emitted at the pipe's distal end. The inner diameter of the lumen may further possess either a smooth, diffuse or a textured surface. The surface characteristics of the reflective lumen or conduit aid in spatially and angularly homogenizing radiation as it passes through the length of the light pipe.

In additional embodiments, the light pipe is of solid construction. The solid core could be cover plated, coated, or clad. Again, a solid construction light pipe generally provides for internal reflection. This internal reflection allows radiation entering the proximal end of the solid light pipe to be channeled through the length of the pipe. The channeled radiation may then be emitted out of the distal end of the pipe without significant loss of radiation intensity.

The faceted elliptical reflector is an example of an embodiment of the present invention which produces only part of the desired characteristics in the output radiation. In the case of the faceted reflector, spatial homogenization is achieved but not angular homogenization. In other cases, such as passing the output of the standard system through ground glass, angular homogenization is achieved but not spatial homogenization. In embodiments such as these, where only angular or spatial homogenization is produced (but not both) some improvement in the performance of the spectroscopic system may be expected. However, the degree of improvement would not be expected to be as great as for systems where spatial and angular homogenization of the radiation are simultaneously achieved.

Another method for creating both angular and spatial homogenization is to use an integrating sphere in the illumination system. Although common to use an integrating sphere for detection of light, especially from samples that scatter light, integrating spheres have not been used as part of the illumination system when seeking to measure analytes noninvasively. In practice, radiation output from the emitter could be coupled into the integrating sphere with subsequent illumination of the tissue through an exit port. The emitter could also be located in the integrating sphere. An integrating sphere will result in exceptional angular and spatial homogenization but the efficiency of this system is significantly less than other embodiments previously specified.

It is also recognized that other modifications can be made to the present disclosed system to accomplish desired homogenization of light. For example, the solid-state light source could be placed inside the light pipe in a sealed arrangement which would eliminate the need for the reflector. Further, the light pipe could be replaced by an integrator, wherein the source is placed within the integrator. Further, the present system could be used in non-infrared applications to achieve similar results in different wavelength regions depending upon the type of analysis to be conducted.

Description of Example Embodiments

In an example embodiment of the present invention (schematically depicted in FIG. 22), a noninvasive alcohol measurement system is comprised of 13 diode lasers that are used to measure 22 discrete wavelengths. Table 1 shows a list of each diode lasers and the associated target peak wavelengths that will be interrogated during the course of the measurement.

TABLE 1

| Light Source # | Wavelengths Measured (cm$^{-1}$) |
| --- | --- |
| 1 | 4196.35, 4227.2 |
| 2 | 4288.91, 4304.34 |
| 3 | 4319.77, 4335.20 |
| 4 | 4350.62 |
| 5 | 4381.48, 4412.34 |
| 6 | 4443.19, 4474.05 |
| 7 | 4535.76, 4566.61 |
| 8 | 4597.47, 4612.90 |
| 9 | 4643.75 |
| 10 | 4674.61, 4690.04 |
| 11 | 4767.17 |
| 12 | 4828.88 |
| 13 | 4875.17, 4906.02 |

In this embodiment, each diode lasers is stabilized to a constant temperature. The peak wavelength of each diode lasers is controlled based on the circuit shown in FIG. 5 (each diode lasers having its own circuit), which also enables the diode lasers to be turned On and Off. The specific state (On/Off) of each diode lasers at a given time during a measurement is determined by a predetermined Hadamard or similar encoding matrix. In example embodiments incorporating solid-state light sources, the Hadamard matrix is a pattern of On/Off states versus time for each diode lasers that is stored in software and implemented in electronics rather than a physical mask or chopper that would mechanically modulate the solid-state light sources. This allows the On/Off states stored in software to be conveyed to the electronic control circuits of each diode lasers during the measurement.

As several of the diode lasers in Table 1 are responsible for 2 wavelength locations, a Hadamard scheme that incorporates all wavelengths can be difficult to achieve. In this case, a combination of scanning and Hadamard encoding can allow all target wavelengths to be measured. In the present embodiment, all diode lasers are tuned to their 1$^{st}$ target wavelength (for those with more than 1 target wavelength) and a Hadamard encoding scheme used to achieve the associated multiplex benefit. The diode lasers can then be tuned to their second target wavelength and a 2$^{nd}$ Hadamard encoding scheme used. Diode lasers with only 1 target wavelength can be measured in either or both groups or divided among the groups.

Furthermore, the groups can be interleaved in time. For example, for a 2 second measurement, the first group can be measured for the 1$^{st}$ second and the 2$^{nd}$ group for the 2$^{nd}$ second. Alternatively, the measurement can alternate at 0.5 second intervals for 2 seconds. The measurement times do not need to be symmetric across the groups. For example, it can be desirable to optimize signal to noise ratio by weighting the measurement time towards one or the other group. One skilled in the art recognizes that many permutations of measurement time, balancing the number of groups, balancing the ratio of scanning to Hadamard, and interleaving are possible and contemplated in the embodiments of the present invention.

In the example embodiment, the output of each diode lasers is combined and homogenized using a hexagonal cross-sectioned light pipe. In some embodiments, the light pipe can contain one or more bends in order to provide angular homogenization in addition to spatial homogenization. Regardless, at the output of the light pipe, the emission of all diode lasers is preferably spatially and angularly homogenized such that all wavelengths have substantially equivalent spatial and angular content upon introduction to the input of the sampling subsystem 200.

The homogenized light is introduced to the input of an optical probe. In the example embodiment, the input is comprised of 225, 0.37NA silica-silica optical fibers (referred to as illumination fibers) arranged in a geometry consistent with the cross section of the light homogenizer. The light is then transferred to the sample interface. The light exits the optical probe and enters the sample, a portion of that light interacts with the sample and is collected by 64 collection fibers. In an exemplary embodiment, the collection fibers are 0.37 NA silica-silica fibers.

The optical probe output arranges the collection fibers into a geometry consistent with the introduction to a homogenizer. For the example embodiment, the homogenizer is a hexagonal light pipe. The homogenizer ensures that the content of each collection fiber contributes substantially equally to the measured optical signal. This can be important for samples, such as human tissue, that can be heterogeneous in nature. The output of the homogenizer is then focused onto an optical detector. In an exemplary embodiment, the optical detector is an extended InGaAs diode whose output current varies based upon the amount of incident light.

The processing subsystem then filters and processes the current and then converts it to a digital signal using a 2 channel delta-sigma ADC. In the example embodiment, the processed analog detector signal is divided and introduced to both ADC channels. As the example embodiment involves VCSEL's with 2 measurement groups (e.g. 2 target wavelengths), a Hadamard transform is applied to the spectroscopic signal obtained from each group and the subsequent transforms combined to form an intensity spectrum. The intensity spectrum is then base 10 log transformed prior to subsequent alcohol concentration determination.

The example embodiment is suitable for either "enrolled" or "walk-up/universal" modalities as well as applications combining alcohol with other analyte properties such as substances of abuse. Furthermore, any of the discussed modalities or combinations can be considered independently or combined with the measurement of a biometric property.

Figure 23:
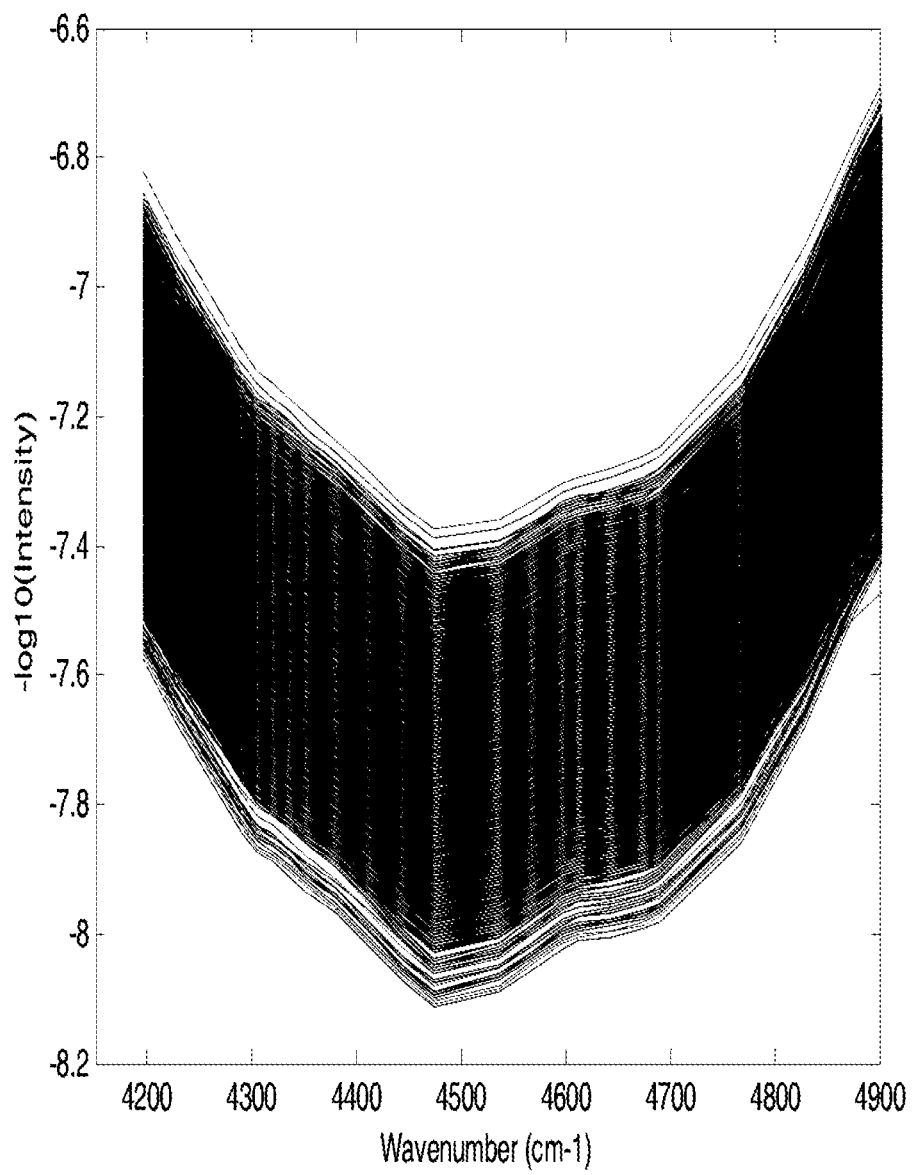
FIG. 23 depicts noninvasive tissue spectra acquired using 22 wavelengths.
Figure 24:
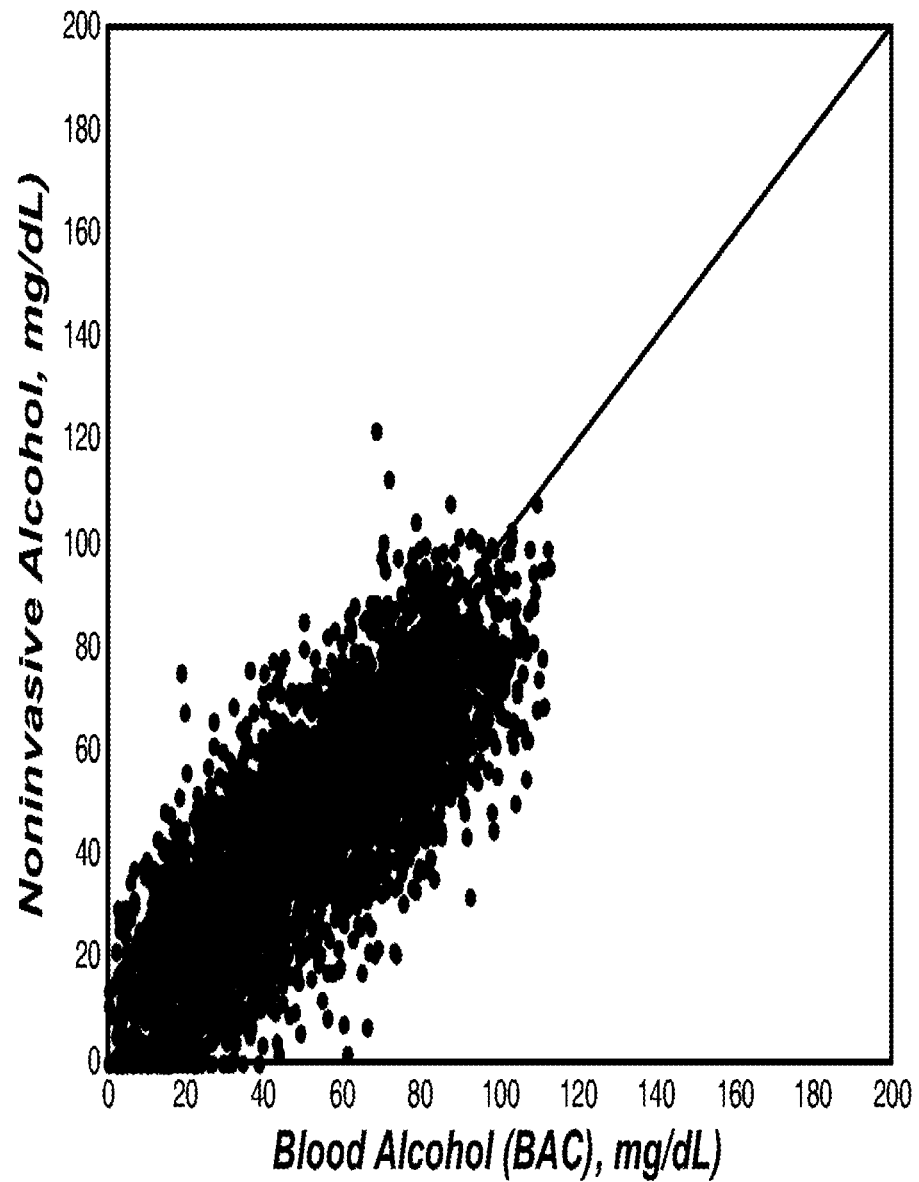
FIG. 24 compares noninvasive tissue alcohol concentrations obtained from the spectra in FIG. 23 to contemporaneous capillary blood alcohol concentration.

3,245 alcohol measurements were obtained from 89 people on 5 noninvasive alcohol systems that measured spectra incorporating 22 wavelengths in the "walk-up" modality. The measurements spanned a wide range of demographic and environmental. FIG. 23 shows the near-infrared spectroscopic measurements obtained from the study. FIG. 24 compares noninvasive alcohol concentrations obtained from the spectroscopic measurements shown in FIG. 23 to contemporaneous capillary blood alcohol concentration (BAC) alcohol.

Another example embodiment is shown in FIG. 39 and uses 39 wavelengths measured using 39 diode lasers. Table 2 shows the diode lasers and their target wavelengths.

TABLE 2

Target Wavelengths for Laser Diodes

| |
| --- |
| 4242.63 |
| 4258.06 |
| 4273.49 |
| 4288.91 |
| 4304.34 |
| 4319.77 |
| 4335.20 |
| 4350.62 |
| 4381.48 |
| 4396.91 |
| 4412.34 |
| 4443.19 |
| 4474.05 |
| 4504.90 |
| 4520.33 |
| 4566.61 |
| 4582.04 |
| 4628.32 |
| 4659.18 |
| 4674.61 |
| 4705.46 |
| 5708.27 |
| 5739.12 |
| 5816.26 |
| 5831.69 |
| 5862.54 |
| 5877.97 |
| 5908.83 |
| 5924.25 |
| 5955.11 |
| 5970.54 |
| 6016.82 |
| 6047.68 |
| 6078.53 |
| 6124.82 |
| 6155.67 |
| 6186.53 |
| 6263.67 |
| 6356.23 |
| 6402.52 |

Figure 25:
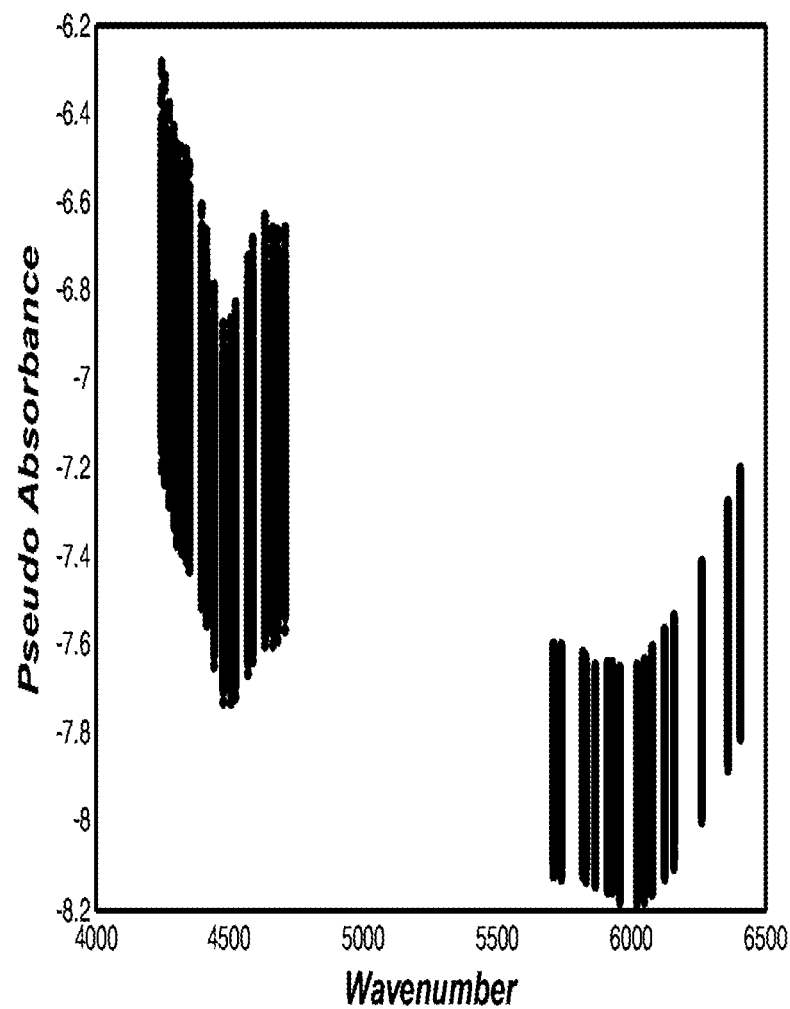
FIG. 25 depicts noninvasive tissue spectra acquired using 39 wavelengths.
Figure 26:
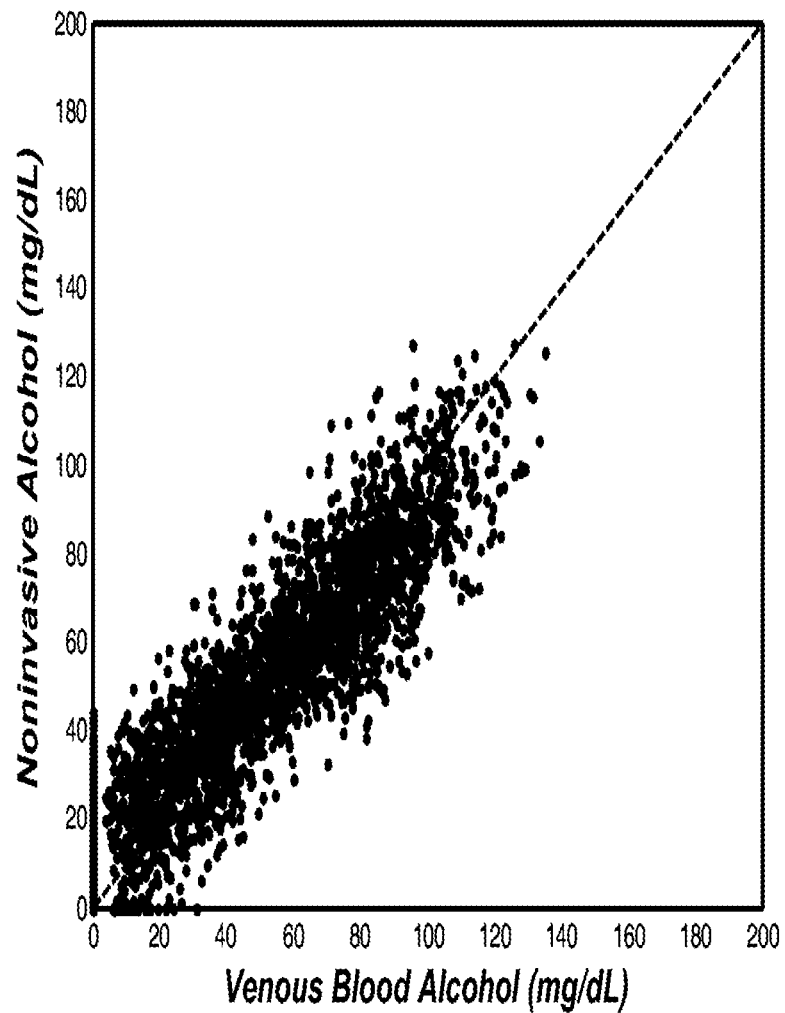
FIG. 26 compares noninvasive tissue alcohol concentrations obtained from the spectra in FIG. 25 to contemporaneous capillary blood alcohol concentration.

The remainder of the system parameters including the sampling subsystem, light homogenizers, detector, and processing is identical to the earlier described embodiment. FIG. 25 shows the 8,999 spectroscopic measurements obtained from 134 people on 6 noninvasive measurement devices. FIG. 26 shows the resulting noninvasive alcohol measurements relative to venous blood alcohol.

In some example embodiments, calibration transfer can be performed using a small number of measurements on samples with known analyte properties. In the case of noninvasive alcohol measurements, each instrument can have a small number of measurements performed on individuals with no alcohol present. Any non-zero alcohol result on the instrument translates into a measurement error that can be used to correct subsequent measurements on that instrument. The number of measurements used to estimate the correction can vary and generally depends on the required accuracy of the correction. In general, this process is analogous to an instrument specific calibration consistent with alcohol devices, such as breath testers, that are calibrated individually.

A similar approach can be applied to calibration maintenance. In many applications of alcohol testing, the majority of measurements are performed on individuals where alcohol is unlikely to be present. For example in workplace safety where employees are routinely tested for alcohol, it is much more likely that an employee will be alcohol free than intoxicated (e.g. most people enter the workplace alcohol-free). In this case, the true alcohol concentration can be assumed to be zero and a median or other means for excluding the infrequent, true alcohol events could be used to estimate an instruments correction. This can implemented as a running median filter, a moving window, or more sophisticated multivariate algorithm for determining the appropriate correction at a given time.

Those skilled in the art will recognize that the present invention can be manifested in a variety of forms other than the specific embodiments described and contemplated herein. Accordingly, departures in form and detail can be made without departing from the scope and spirit of the present invention.

On Going System Calibration

In order to maintain maximum accuracy and precision across operating conditions and time, it is desirable to have information about the state of the alcohol measurement devices (e.g. the optical and electrical components that contribute to the measurement) just prior to tissue measurement. This is referred to as a "calibration measurement". While controls related to current and temperature are employed for certain sensitive components of the system, there are a significant number of mechanical and optical error contributors that may change with time and temperature. In addition, even with controls in place, there can be error associated with the operation of the electrical components as well as factors related to the surface treatment, and possible light contamination, of the probe that also need to be considered. Therefore, it is desirable to measure the complete optical and electrical status of the device against a known standard sample just prior to measuring the tissue sample of interest. The measurement of the standard sample then allows subsequent (or preceding) tissue measurements to be corrected for the current status of the alcohol measurement device.

To obtain a calibration measurement, light from the light source/modulation subsystem (100) is delivered to the standard sample by the sampling subsystem (200) where it interacts with the standard sample. A portion of the light is collected by the sampling subsystem (200) and coupled to the photodetector in the data acquisition subsystem (300). One way to achieve this is with optical fibers distinct from those of the sampling surface (e.g. the surface where skin tissue is measured). In this case, the light delivered to the standard sample would travel a different optical path than the light that interrogates skin. This difference in optical path can be acceptable in some embodiments. Furthermore, in other embodiments, the optical fibers themselves can serve as the standard sample (e.g. the optical fibers collect light from the light source/modulation subsystem (100) and deliver it directly to the photodetector in the data acquisition subsystem (300). In some embodiments of these approaches a gating mechanism can be applied that selects which optical path (the path to the skin sampling surface or the path to the calibration sample) is being measured by the photodetector at a given time. While these approaches are acceptable in some embodiments, they are not optimal in the sense that a different path from the actual probe is measured.

Therefore, in order to maintain substantially the same optical paths for light interrogating skin tissue and the calibration standard a method is required to place a movable calibration standard with known characteristics at the tissue interface of the sampling subsystem (200). The calibration sample can be measured shortly prior to tissue measurement and then removed for actual measurement. While the calibration sample can be manually inserted into the path, an automatic method for insertion and removal is preferred in some embodiments.

One such method for automatic insertion of the calibration sample is to build it into the probe head cover or a button that the user interacts with. The main elements of such a method would be:
1) A movable door in close proximity to the tissue interface onto which a reflective standard surface is added to the back
2) A method for moving the door out of the way to present a tissue measurement surface directly to the probe
3) A method to return the reflective surface to a rest position It should be noted that one skilled in the art may design any number of electromechanical or mechanical mechanisms to accomplish this purpose.

In the first embodiment, movable door, is coated on the underside with suitable reflecting material and slides, allowing sensing head to rotate up to a finger surface. The spring provides a return force necessary to return to the rest/calibration position.

In the second embodiment, a sliding button acts as a guide for semi flexible tape which is fixed at the bottom end. The back of the flexible tape is coated with a suitable reflective surface. Movement of the sliding button allows the tape to slide below the window opening on the face of the button allowing sensor to come in contact with the finger. The spring provides return force necessary to return to the rest/calibration condition. It should be noted that alternative embodiments can be designed such that the sensing head is stationary while the door/button and/or calibration sample are the only moving parts.

It should be further noted that the embodiments can be enhanced with styling features and finger guides to help facilitate placement without changing the basic concept, and that the mechanism and additional styling features would work equally well whether the dorsal side of the finger, palmer side of the finger, or other skin surface is presented.

Figure 28:
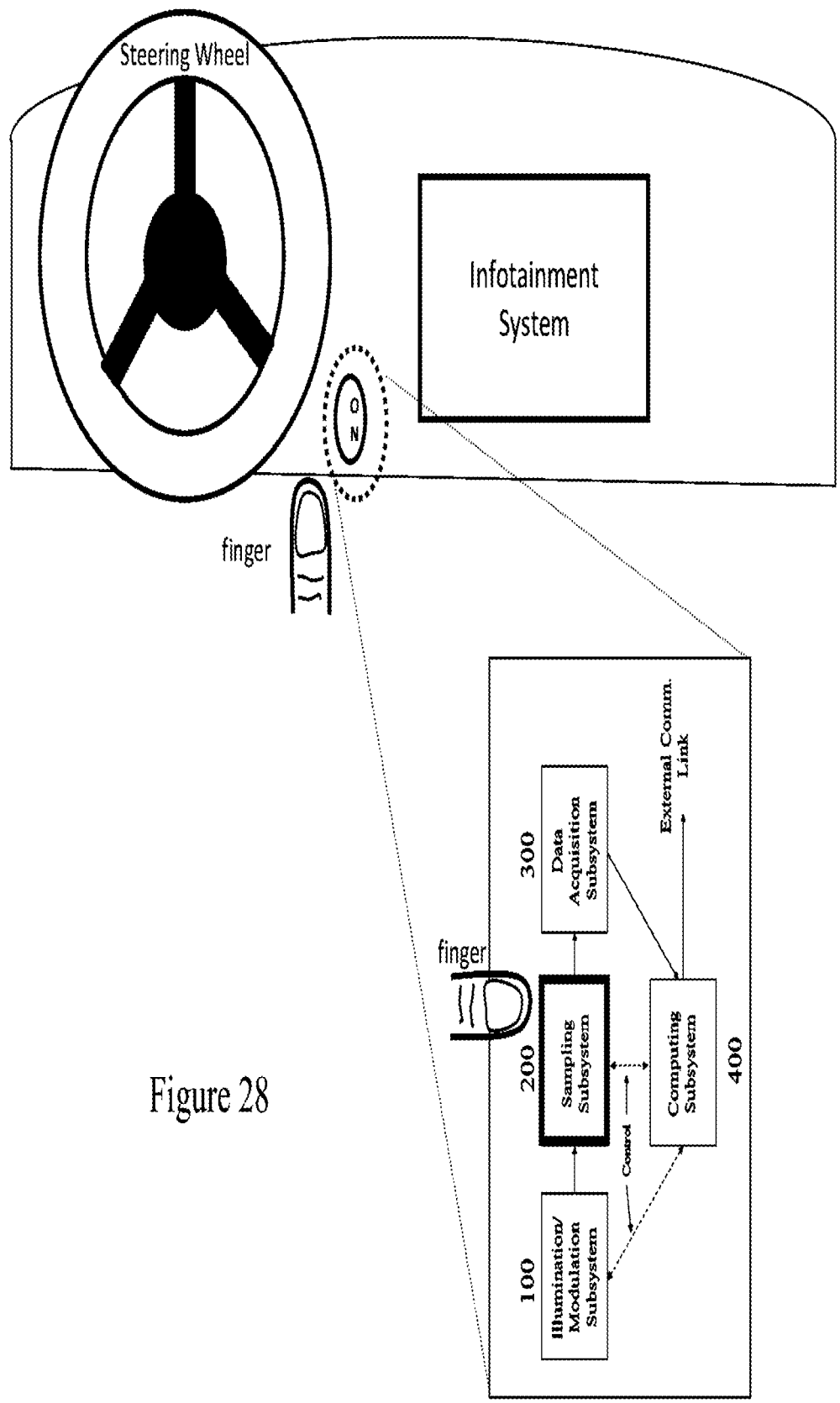
FIG. 28 depicts a non-invasive monitoring system incorporated as a vehicle starter button in a vehicle instrument panel.

Referring to FIG. 28, the system depicted in FIG. 1 can be incorporated into the starting system of any transport vehicle (including all forms of ground, water and air travel). For example, the system can be incorporated as an electromechanical component of an ignition system including a starter button, key turn or other typically used form of a driver initiating power to prepare the transport vehicle for travel.

Figure 27:
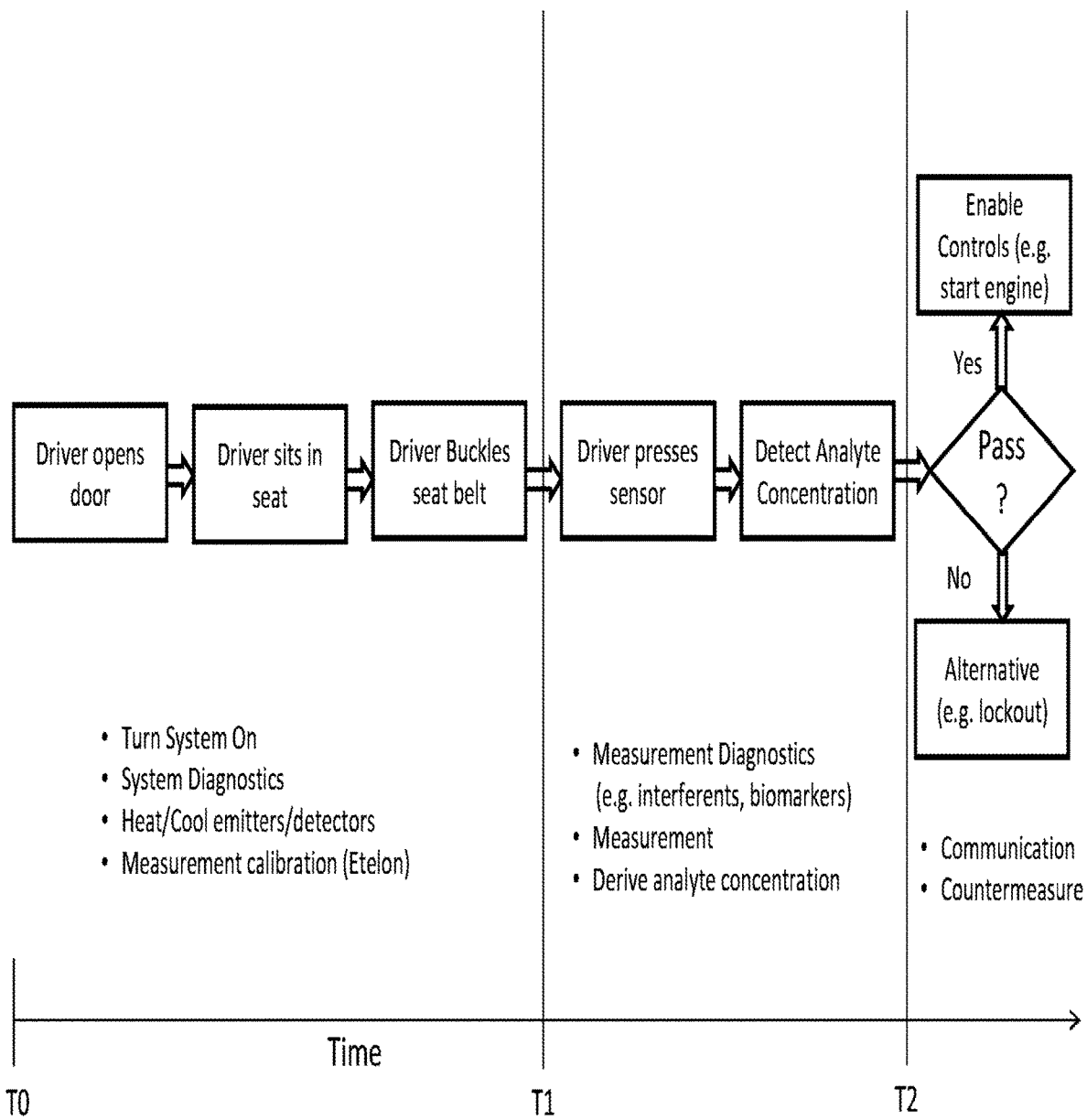
FIG. 27 depicts one of many possible embodiment of a measurement timeline including system calibration, measurement, and counter measures time zones.

Such a system can be utilized to measure the presence or concentration of an analyte or biometric identifier in a person attempting to start the transport vehicle where the measured information is used to alter the subsequent electromechanical response of the vehicle. For example, a biometric identification may be used to identify a specific driver (from a pool of possible drivers) and modify the position or orientation of the driver and/or control settings such as infotainment settings or vehicle actuator settings. In another example, as illustrated in FIG. 27, the system can be used to measure the concentration of an analyte to either enable/or disable the ability to start the transport vehicle and/or initiate an alternative action. For example, measurement of alcohol in a vehicle driver above the legal threshold may restrict the ability to start the transport vehicle, but also trigger a telematics system to provide an automated call to alternative forms of travel including designated drivers and/or taxis.

In another embodiment, the system can be integrated in a transport vehicle control system which is continuously or nearly continuously in contact with the operator such as a steering wheel, handle bars or yoke. As such, the system can continuously or periodically; or triggered by other control logic make analyte and/or biometric measurements which are used to affect the subsequent transport vehicle operation or trigger an alternative action.

In another embodiment, the system can be integrated into a transport vehicle or facility access system (e.g. entry door, trunk, . . . ) and thus make analyte and/or biometric measurement which are used to affect the access into and/or subsequent levels of control upon entry.

In another embodiment, the system can be incorporated into other transport vehicle sub-systems where direct contact between the operator skin and the sampling sub-system 200 is temporarily, periodically or constantly is maintained. A slightly modified embodiment where semi-passive contact is maintained and an embodiment where contact is made through an operator initiated action are also possible. In such cases, continuous or periodic analyte and/or biometric measurements can be made which effect the subsequent transport vehicle operation or trigger an alternative action.

In the case of the system described in FIG. 28, the human machine interaction between the operator and the sampling sub-system 200 can be configured to inform the intended operator of the existence of the system and intended body part and/or location which must be coupled with the sampling sub-system to trigger a measurement. For example, the use of audible sounds and/or speech and/or lighting and or haptic feedback can be used to educate the operator, provide positive/negative feedback on the proper measurement process and/or the results of the measurement.

Figure 22:
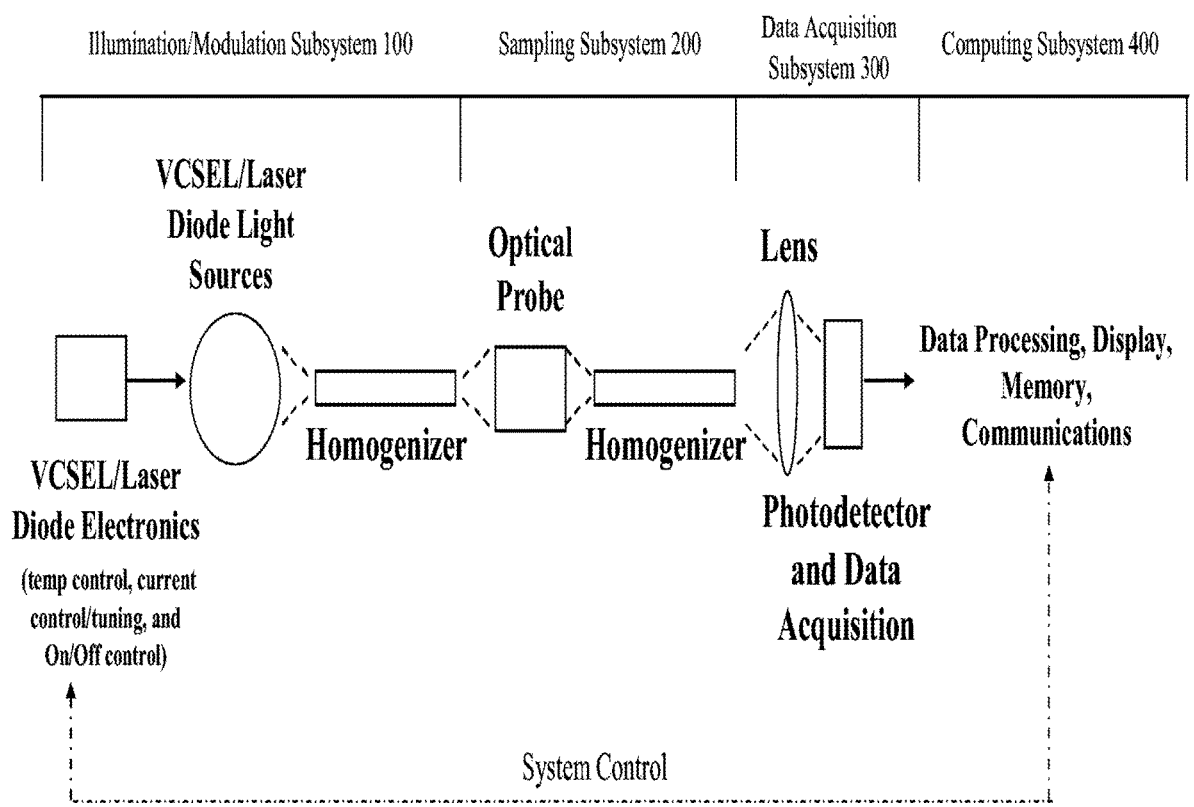
FIG. 22 shows a schematic of the components of an exemplary embodiment of the present invention.
Figure 29A:
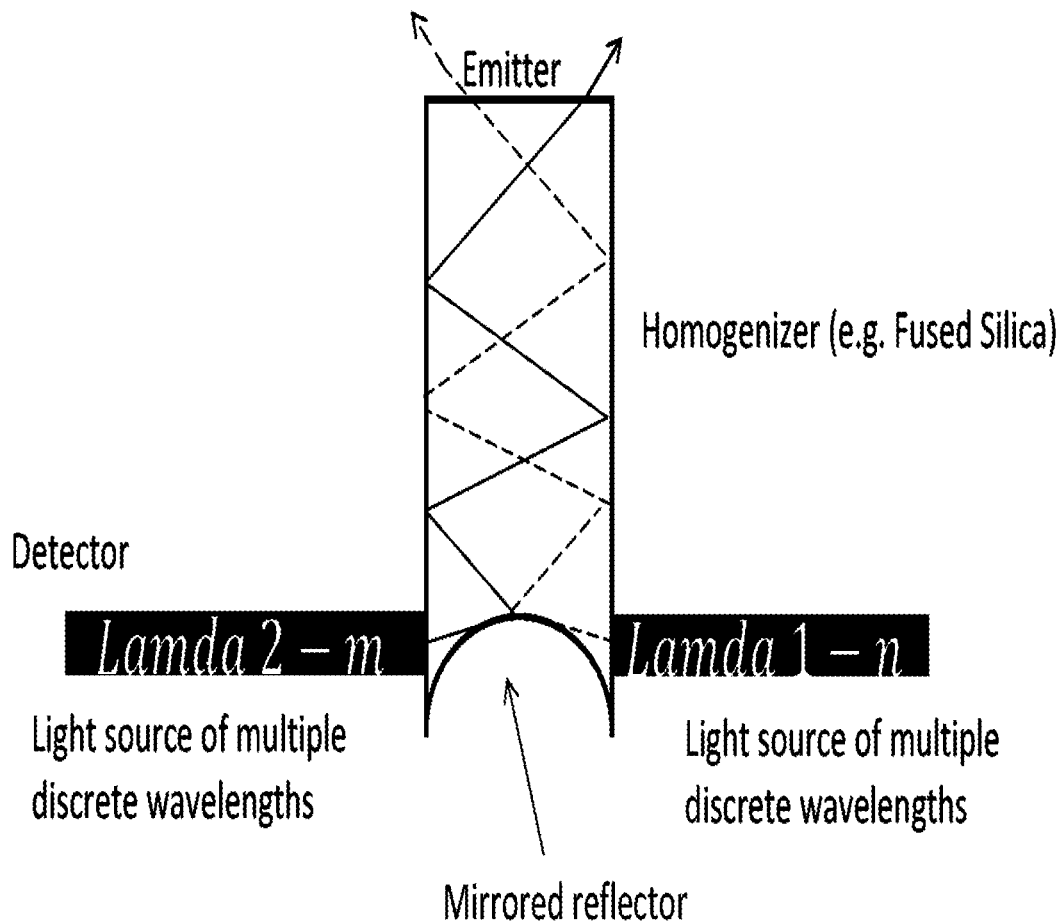
FIG. 29a depicts a side view of a non-invasive measurement portal interface where the emitter is a wavelength homogenizer directly connected to wavelength light sources.
Figure 29B:
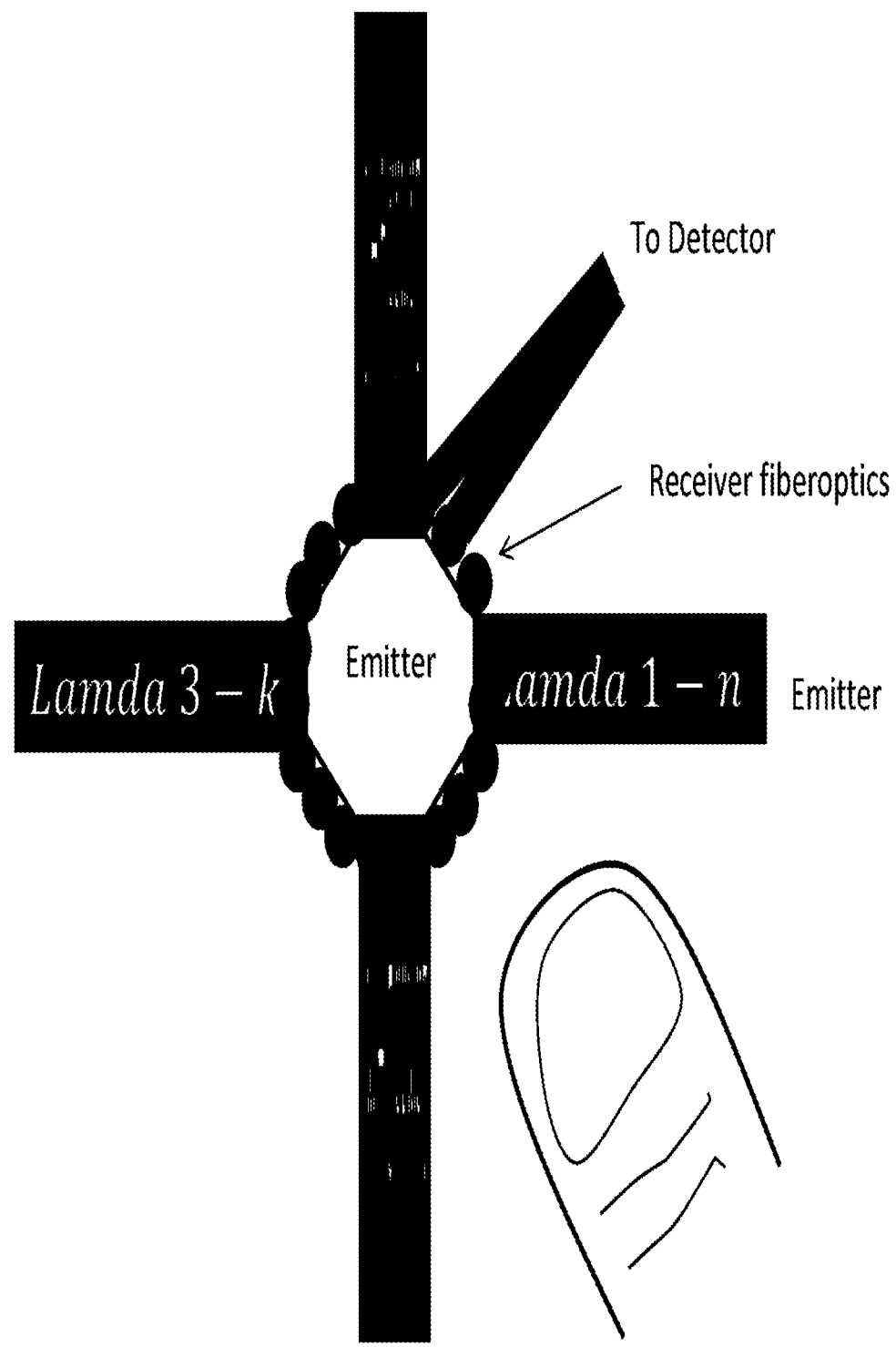
FIG. 29b depicts a top view of the non-invasive measurement portal interface of FIG. 29a where the emitter is a wavelength homogenizer directly connected to wavelength light sources.

In an example embodiment of the present invention (schematically depicted in FIG. 29*a*-*b*), differs from the system depicted in FIG. 22, by directly coupling discrete solid-state light sources of varying wavelength into a homogenizer consisting of a material which minimizes the losses across all supported wavelengths thus reducing the need for a coupling mechanism between the solid-state light source and the homogenizer and the sensing sub-system. In this embodiment, the homogenizer material, size, shape, coating can be controlled to optimize light transmission and minimize losses while directly providing the sensor sub-system 200 emitter.

Figure 30:
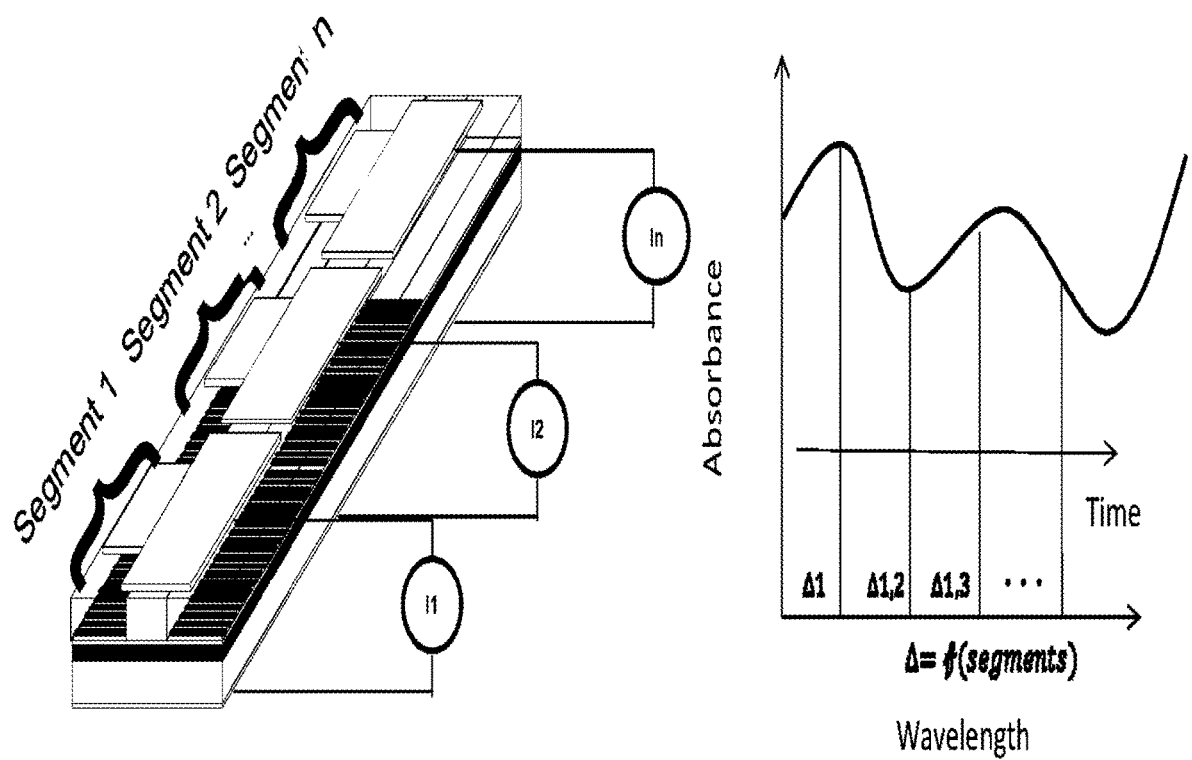
FIG. 30 depicts the components of a non-invasive monitoring system which utilizes a broadly tunable laser emitter to provide a means for spectrally separated absorption measurements.

FIG. 7 depicts a system where multiple distinct emitters are used; in an alternative embodiment depicted in FIG. 30, a single emitter can be created with several grating zones with distinct current paths which when driven with current in combinations product distinct wavelengths. By time varying which grating combinations are driven, distinct wavelengths can be achieved in a time domain signal. In such a way, a multitude of wavelengths can be sampled in time in a pre-determined pattern. Knowledge of the sampling sequence in the detector and processor can be used to obtain the spectroscopy measurements described in subsequent embodiments.

In another embodiment, the system further includes one or more atmospheric, temperature and relative humidity sensors where the measurements derived from these sensors are available to the sub-system 400 to correct for and/or improve on the analyte and/or biometric measurements to correct for human variation due to these environmental effects and/or individual sub-system variations due to an extended system (for example, where the measurement sub-system 200 is spatially or thermally distinct from sub-system 100; or where the system emitters and detectors are temperature compensated to a fixed value (independent of ambient conditions), but the fiberoptics, homogenizer and couplers require temperature compensation based on ambient conditions.

Figure 31:
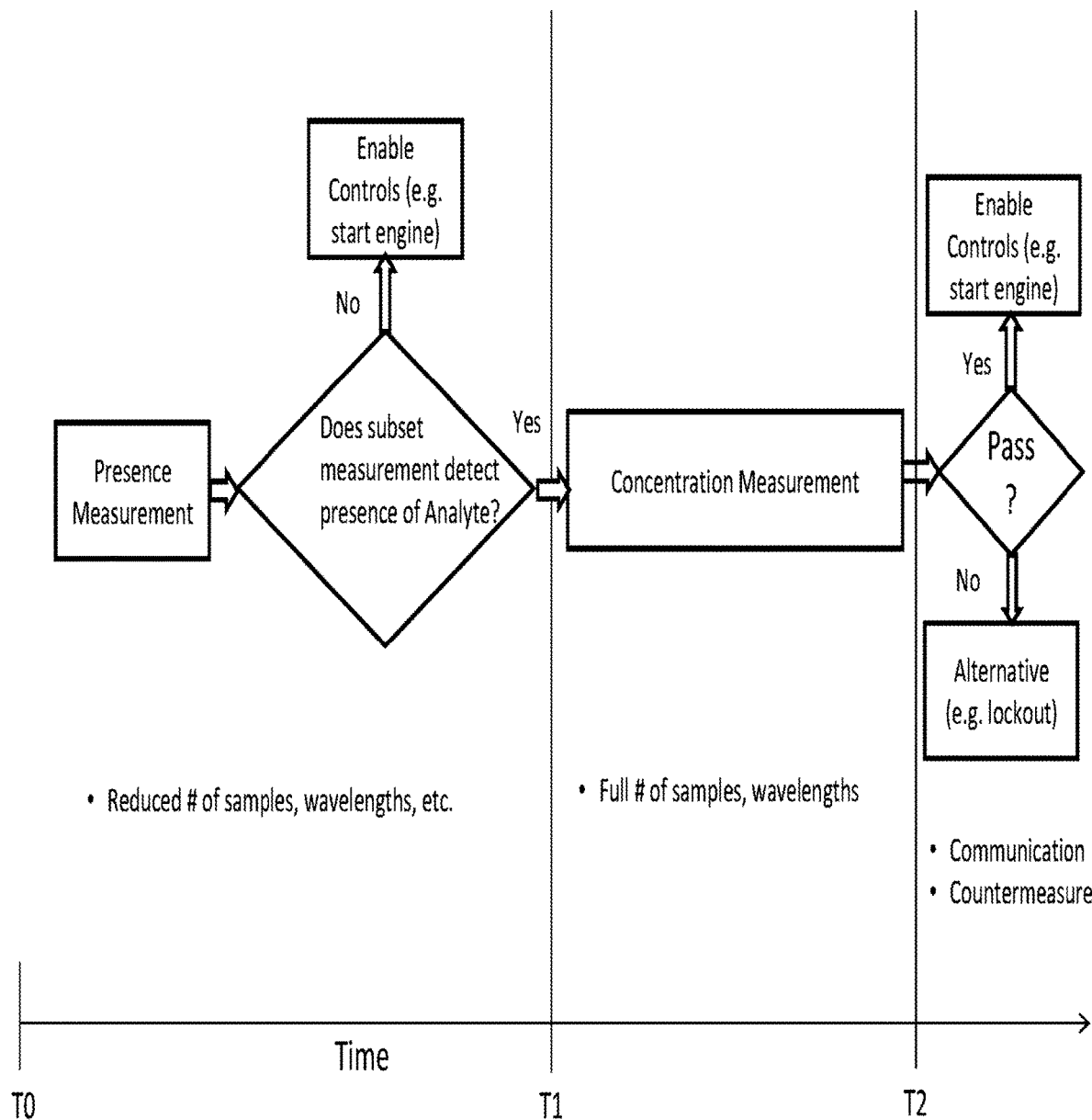
FIG. 31 depicts one of many possible embodiment of a measurement timeline to improve the average required measurement time where the initial measurement detects the existence of an analyte, and a subsequent measurement is made to determine the actual concentration of the analyte.

In the case of making some analyte measurements where the probability of the presence of the analyte in the pool of potential operators is low, it may be favorable to make a faster and simpler measurement to first determine if any analyte is apparent, and only if detected, then make a subsequent measurement for the concentration of the analyte. This is depicted in FIG. 31. For example, in the case of alcohol as an analyte, the majority of prospective vehicle operators will not have the presence of alcohol in their system when attempting to start the vehicle. A presence measurement can be used to decrease the average measurement time.

Figure 32:
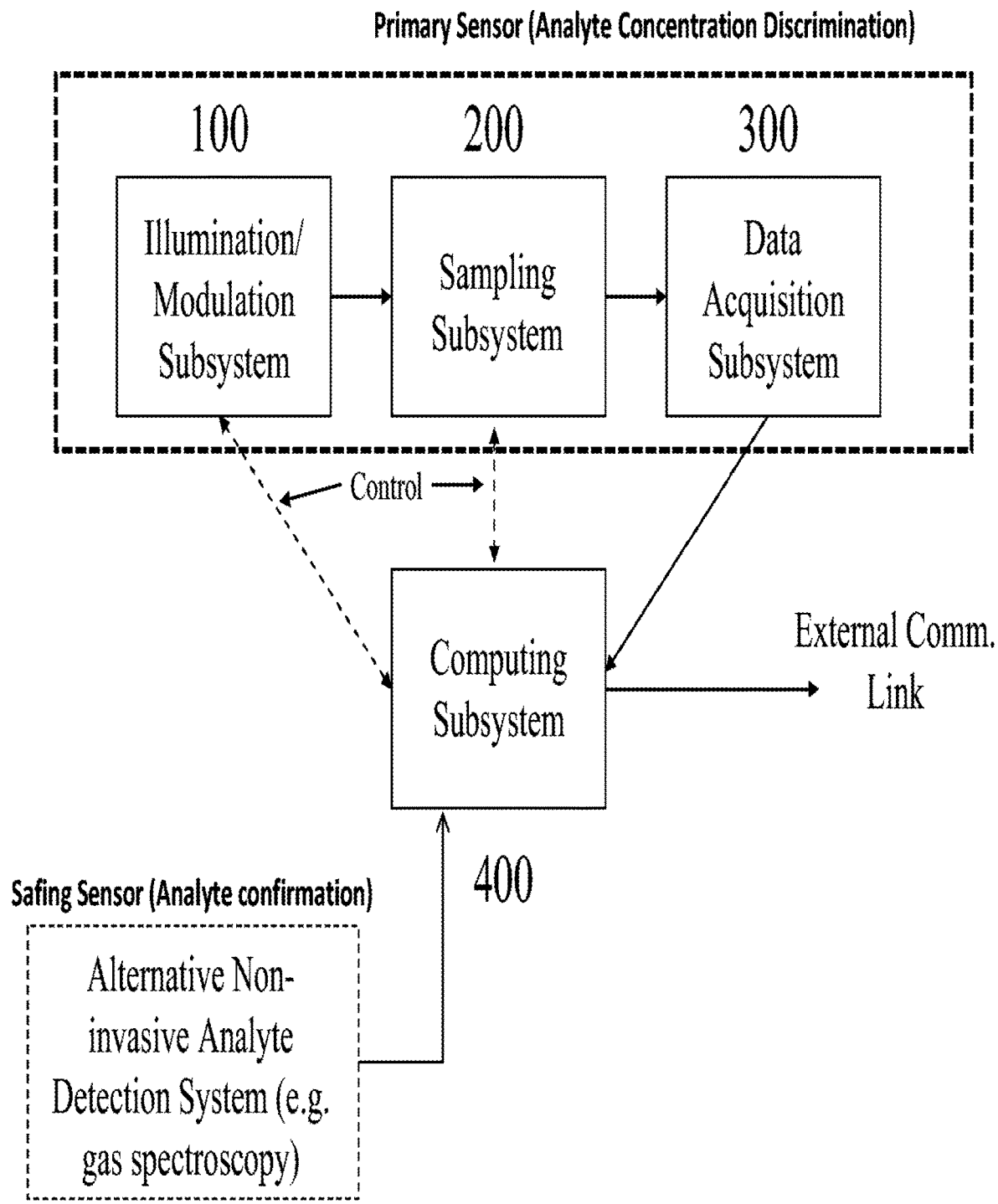
FIG. 32 depicts a non-invasive monitoring system where the primary analyte measurement is made through a touch system and a secondary measurement is made through an alternative analyte detection system.

In many safety applications, at least two disparate technology sensors must detect a signal to make a decision to actuate a countermeasure. This vastly reduces the propensity for false positives due to undetected single sensor failure or errors. In a similar context, the system described in FIG. 32 can be coupled to include one or more independent sensors to indicate the presence or concentration of an analyte and/or confirm a biometric measurement.

Figure 33:
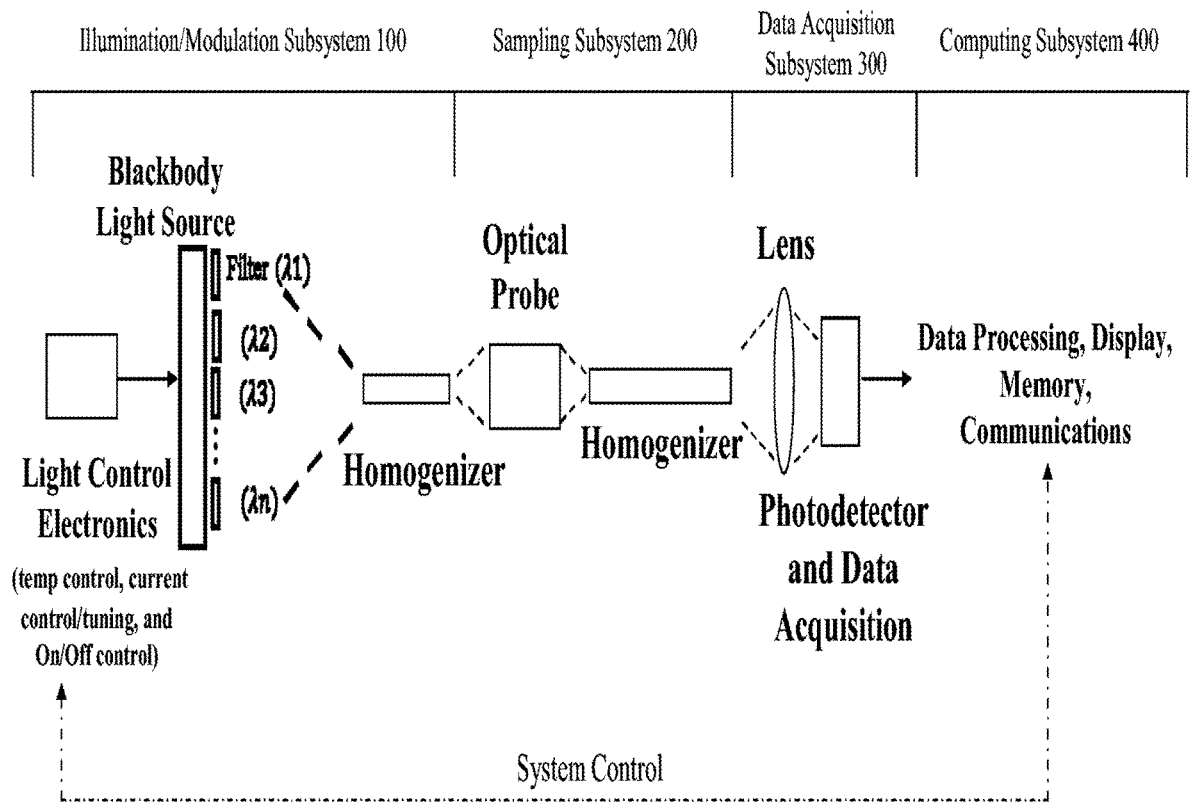
FIG. 33 depicts the components of a non-invasive monitoring system which utilizes a blackbody light source with filter elements to provide the selection of discrete wavelengths to compose the emitted light source.

The system in FIG. 22 describes a system utilizing discrete wavelength solid-state light sources; an alternative embodiment depicted in FIG. 33 depicts a system which utilizes a single wide spectrum black body source coupled to discrete wavelength filters which only pass the intended wavelengths. The subsequent processing steps remain the same as those indicated previously; however, undesirable system noise can be avoided in the detection and discrimination process.

Figure 34:
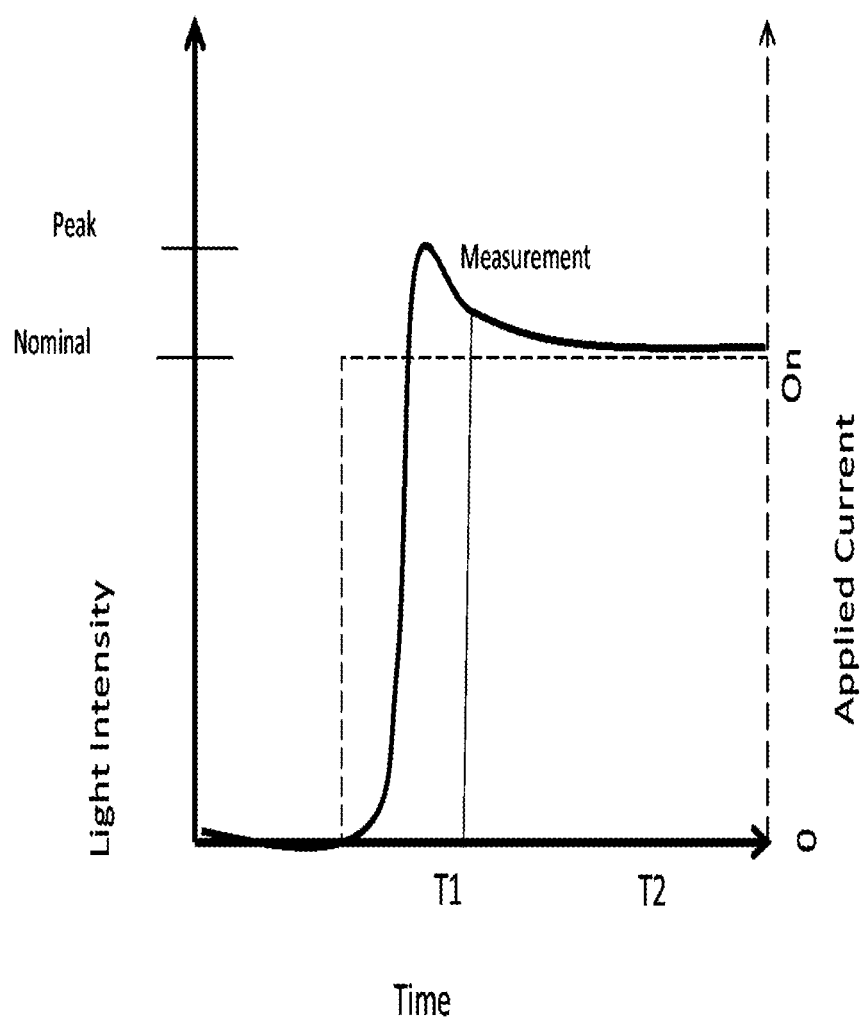
FIG. 34 depicts the intensity of a light source during transition from an off state to an on state time of measurement is made prior to intensity settling.

For system embodiments described previously which utilize diode lasers, the rise and fall characteristics of those devices can very in a deterministic fashion based on the driver and compensation circuits and also the ambient temperature and electromechanical properties of the device itself (for example, the laser grating structures, materials, size, shape and heating/cooling components). As illustrated in FIG. 34, waiting until the solid-state light source intensity has settled to a desirable level (T2), may reduce the modulation time. In order to improve the modulation rates available for multi-plexing lights of varying wavelength, the a-priori rise/fall properties can be compensated for in the detector logic thus reducing the settling time (T1).

It is to be understood that both the foregoing general description and detailed description are exemplary and explanatory only, and are not restrictive of the invention.

For purposes of this disclosure, the term "coupled" means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components or the two components and any additional member being attached to one another. Such joining may be permanent in nature or alternatively may be removable or releasable in nature.

The construction and arrangement of the diffuser as shown in the preferred and other exemplary embodiments is illustrative only. Although only a few embodiments of the present airbag assembly have been described in detail in this disclosure, those skilled in the art who review this disclosure will readily appreciate that many modifications are possible (e.g. variations in sizes, dimensions, structures, shapes and proportions of the various elements, values of parameters, mounting arrangements, use of materials, orientations, etc.) without materially departing from the novel teachings and advantages of the subject matter recited in this disclosure. Accordingly, all such modifications attainable by one versed in the art from the present disclosure within the scope and spirit of the present invention are to be included as further embodiments of the present invention. The order or sequence of any process or method steps may be varied or re-sequenced according to alternative embodiments. Other substitutions, modifications, changes and omissions may be made in the design, operating conditions and arrangement of the preferred and other exemplary embodiments without departing from the spirit of the present application.

What is claimed is:

1. A system for non-invasively measuring an analyte in a vehicle driver and controlling a vehicle based on a measurement of the analyte, the system comprising:
    a laser bar comprising:
        a first plurality of solid-state light sources, wherein each of the solid-state light sources of the first plurality of solid-state light sources emit light at a first wavelength;
        a second plurality of solid-state light sources, wherein each of the solid-state light sources of the second plurality of solid-state light sources emit light at a second, different wavelength;
    a first light-transmissive fiber for receiving and combining the light emitted by the first plurality of solid-state light sources so as to provide a first combined beam of light;
    a second light-transmissive fiber for receiving and combining the light emitted by the second plurality of solid-state light sources so as to provide a second combined beam of light;
    an optical cable for receiving and combining the first combined beam of light and the second combined beam of light so as to provide a third combined beam of light;
    a sample device configured to introduce the third combined beam of light emitted by the optical cable into tissue of the vehicle driver;
    one or more optical detectors configured to detect a portion of the third combined beam of light that is not absorbed by the tissue of the vehicle driver; and
    a controller configured to calculate a measurement of the analyte in the tissue of the vehicle driver based on the light detected by the one or more optical detectors, determine whether the measurement of the analyte in the tissue of the vehicle driver exceeds a pre-determined value, and provide a signal to a device configured to control the vehicle.

2. The system of claim 1, further comprising a biometric device configured to identify or verify an identity of the vehicle driver.

3. The system of claim 2, wherein the biometric device collects a set of biometric data from the vehicle driver and compares the set of biometric data with a set of enrollment data corresponding to authorized vehicle drivers stored in the biometric device to identify which, if any, of the authorized vehicle drivers provided the set of biometric data.

4. The system of claim 2, wherein the prospective vehicle driver provides a purported identity to the vehicle, the biometric device is configured to collect a set of biometric data from the prospective vehicle driver, and the biometric device is configured to verify whether an actual identity of the prospective vehicle driver is the purported identity of the prospective vehicle driver by comparing the set of biometric data of the prospective vehicle driver with the set of enrollment data corresponding to the purported identity of the prospective vehicle driver.

5. The system of claim 1, wherein an intensity of each solid-state light source of the first plurality of solid-state light sources and the second plurality of solid-state light sources is configured to be independently modulated.

6. The system of claim 1, wherein the light emitted by at least one solid-state light source of the first plurality of solid-state light sources and the second plurality of solid-state light sources and the light detected by the one or more optical detectors has a wavelength between 1,000 nm and 2,500 nm.

7. The system of claim 1, further comprising a microcontroller configured to turn the first plurality of solid-state light sources and the second plurality of solid-state light sources on and off according to a set of states defined by a pre-determined modulation scheme.

8. The system of claim 1, wherein each solid-state light source of the first plurality of solid-state light sources and the second plurality of solid-state light sources is configured to be tuned to multiple peak wavelength locations such that the system is capable of measuring more wavelength locations than a number of solid-state light sources provided in the system.

9. The system of claim 1, further comprising a light homogenizer configured to provide uniform radiance of the third combined beam of light introduced, by the sample device, into the tissue of the vehicle driver.

10. The system of claim 1, wherein the measurement of the analyte comprises a presence, a concentration, a rate of change of the concentration, a direction of change of the concentration or a combination thereof of the analyte.

11. The system of claim 1, wherein the measurement of the analyte is obtained using multivariate analysis.

12. The system of claim 1, wherein the first plurality of solid-state light sources and the second plurality of solid-state light sources are arranged in a planar array.

13. The system of claim 1, wherein the first plurality of solid-state light sources and the second plurality of solid-state light sources are divided into one or more groups and each solid-state light source within the one or more groups is mounted onto a common carrier for each group with a predefined spacing between other solid-state light sources mounted on a same common carrier.

14. The system of claim 1, wherein the first plurality of solid-state light sources and the second plurality of solid-state light sources are located within a single semiconductor to form the laser bar.

15. The system of claim 1, wherein the system is configured to measure more than one analyte.

16. A method for non-invasively measuring an analyte in a vehicle driver and controlling a vehicle based on a measurement of the analyte, the method comprising:
providing a system for non-invasively measuring an analyte in a vehicle driver and controlling a vehicle based on a measurement of the analyte, the system comprising:
a laser bar comprising:
a first plurality of solid-state light sources, wherein each of the solid-state light sources of the first plurality of solid-state light sources emit light at a first wavelength;
a second plurality of solid-state light sources, wherein each of the solid-state light sources of the second plurality of solid-state light sources emit light at a second, different wavelength;
a first light-transmissive fiber for receiving and combining the light emitted by the first plurality of solid-state light sources so as to provide a first combined beam of light;
a second light-transmissive fiber for receiving and combining the light emitted by the second plurality of solid-state light sources so as to provide a second combined beam of light;
an optical cable for receiving and combining the first combined beam of light and the second combined beam of light so as to provide a third combined beam of light;
a sample device configured to introduce the third combined beam of light emitted by the optical cable into tissue of the vehicle driver;
one or more optical detectors configured to detect a portion of the third combined beam of light that is not absorbed by the tissue of the vehicle driver; and
a controller configured to calculate a measurement of the analyte in the tissue of the vehicle driver based on the light detected by the one or more optical detectors, determine whether the measurement of the analyte in the tissue of the vehicle driver exceeds a pre-determined value, and provide a signal to a device configured to control the vehicle;
introducing the light beam into tissue of the vehicle driver;
detecting, by the one or more optical detectors, a portion of the light that is not absorbed by the tissue of the vehicle driver;
calculating, by the controller, a measurement of the analyte in the tissue of the vehicle driver based on the light detected by the one or more optical detectors;
determining, by the controller, whether the measurement of the analyte in the tissue of the vehicle driver exceeds a pre-determined value; and
controlling the vehicle based on the measurement of the analyte in the tissue of the vehicle driver.

17. The method of claim 16, further comprising: collecting, by a biometric device, a set of biometric data to identify the vehicle driver; comparing, by the biometric device, the set of biometric data with a set of enrollment data corresponding to authorized vehicle drivers previously stored in the biometric device; and identifying which, if any, of the authorized vehicle drivers provided the set of biometric data.

18. The method of claim 16, further comprising: providing, by a prospective vehicle driver, a purported identity to the vehicle; collecting, by the biometric device, a set of biometric data from the prospective vehicle driver; comparing, by the biometric device, the set of biometric data to the set of enrollment data corresponding to the purported identity of the prospective vehicle driver; and verifying, by the biometric device, whether an actual identity of the prospective vehicle driver is the purported identity of the prospective vehicle driver based on the comparison.

19. The method of claim 16, wherein an intensity of each solid-state light source of the first plurality of solid-state light sources and the second plurality of solid-state light sources is independently modulated.

20. The method of claim 16, further comprising turning at least one solid-state light source of the first plurality of solid-state light sources and the second plurality of solid-state light sources on and off, by a microcontroller, according to a set of states defined by a pre-determined modulation scheme.

21. The method of claim 16, wherein the measurement of the analyte comprises a presence, a concentration, a rate of change of the concentration, a direction of change of the concentration, or a combination thereof of the analyte.

22. The method of claim 16, wherein the measurement of the analyte is obtained using multivariate analysis.

23. The method of claim 16, further comprising measuring more than one analyte.

24. The method of claim 16, wherein the system further comprises a light homogenizer configured to provide uniform radiance of the third combined beam of light introduced, by the sample device, into the tissue of the vehicle driver.

* * * * *